(12) United States Patent
Tajima

(10) Patent No.: US 9,128,368 B2
(45) Date of Patent: Sep. 8, 2015

(54) RADIATION IMAGE CAPTURING APPARATUS AND RADIATION IMAGE CAPTURING SYSTEM

(75) Inventor: Hideaki Tajima, Hachioji (JP)

(73) Assignee: KONICA MINOLTA, INC. (JP)

( * ) Notice: Subject to any disclaimer, the term of this patent is extended or adjusted under 35 U.S.C. 154(b) by 161 days.

(21) Appl. No.: 13/822,142

(22) PCT Filed: Mar. 2, 2011

(86) PCT No.: PCT/JP2011/054699
§ 371 (c)(1),
(2), (4) Date: Mar. 11, 2013

(87) PCT Pub. No.: WO2012/032801
PCT Pub. Date: Mar. 15, 2012

(65) Prior Publication Data
US 2013/0161526 A1 Jun. 27, 2013

(30) Foreign Application Priority Data
Sep. 9, 2010 (JP) ................................. 2010-201502

(51) Int. Cl.
G01T 1/20 (2006.01)
G03B 42/02 (2006.01)
H01L 27/146 (2006.01)
(Continued)

(52) U.S. Cl.
CPC .............. *G03B 42/02* (2013.01); *A61B 6/4208* (2013.01); *A61B 6/5258* (2013.01); *H01L 27/14609* (2013.01); *H04N 5/32* (2013.01);
(Continued)

(58) Field of Classification Search
CPC ..................................................... H04N 5/3597
See application file for complete search history.

(56) References Cited

U.S. PATENT DOCUMENTS

| 7,211,803 B1 | 5/2007 | Dhurjaty et al. |
| 2003/0086523 A1 | 5/2003 | Tashiro |

(Continued)

FOREIGN PATENT DOCUMENTS

| JP | 6-342099 A | 12/1994 |
| JP | 7-72252 A | 3/1995 |

(Continued)

OTHER PUBLICATIONS

Extended European Search Report for Application No./Patent No. 11823280.0-1902/2614772, dated Jan. 20, 2014.

(Continued)

*Primary Examiner* — Constantine Hannaher
(74) *Attorney, Agent, or Firm* — Cantor Colburn LLP

(57) ABSTRACT

If a control unit of a radiation image capturing apparatus acquires dark image data before photographing and at the same time detects initiation of irradiation of radiation based on image data read out by carrying out a readout process of the image data, the control unit applies off-voltage to all the scanning lines and shifts to an electric charge accumulation mode, and after the irradiation is over, sequentially applies on-voltage to each of the scanning lines, causes the scanning lines to carry out readout process of main image data from each of radiation detection elements, and subsequently acquires offset data in a condition where radiation is not irradiated to correct the main image data read out by the photographing or main image data read out by a photographing carried out after the former photographing based on offset lag part calculated from the offset data and the dark image data.

11 Claims, 39 Drawing Sheets

(51) Int. Cl.
*A61B 6/00* (2006.01)
*H04N 5/32* (2006.01)
*H04N 5/361* (2011.01)
*H04N 5/378* (2011.01)

(52) U.S. Cl.
CPC .............. *H04N 5/361* (2013.01); *H04N 5/378* (2013.01); *A61B 6/4233* (2013.01); *A61B 6/4283* (2013.01)

(56) References Cited

U.S. PATENT DOCUMENTS

| | | | |
|---|---|---|---|
| 2006/0239407 A1* | 10/2006 | Nascetti et al. ............... | 378/98.8 |
| 2007/0040099 A1 | 2/2007 | Yokoyama | |

FOREIGN PATENT DOCUMENTS

| | | |
|---|---|---|
| JP | 7-506993 A | 8/1995 |
| JP | 9-73144 A | 3/1997 |
| JP | 9-107503 A | 4/1997 |
| JP | 9-140691 A | 6/1997 |
| JP | 9-197051 A | 7/1997 |
| JP | 11-500949 A | 1/1999 |
| JP | 11-155847 A | 6/1999 |
| JP | 2003-126072 A | 5/2003 |
| JP | 2004-344249 A | 12/2004 |
| JP | 2006-58124 A | 3/2006 |
| JP | 2006526925 A | 11/2006 |
| JP | 2007075598 A | 3/2007 |
| JP | 2007-151761 A | 6/2007 |
| JP | 2008-595 A | 1/2008 |
| JP | 2008-132216 A | 6/2008 |
| JP | 2009-153984 A | 7/2009 |
| JP | 2009-201587 A | 9/2009 |
| JP | 2009-219538 A | 10/2009 |
| JP | 2010-12082 A | 1/2010 |
| JP | 2010-152279 A | 7/2010 |
| WO | 93/25059 A1 | 12/1993 |
| WO | 2004/110056 A1 | 12/2004 |
| WO | 2009/005119 A1 | 1/2009 |

OTHER PUBLICATIONS

International Preliminary Report on Patentability for International Application No. PCT/JP2011/054699, issued Apr. 9, 2013, with English translation.

International Search Report for International application No. PCT/JP2011/054699, mailed May 24, 2011, with English translation.

Notification of Reasons for Refusal for Japanese Patent Application No. 2012-532876; Date of Mailing: Aug. 26, 2014, with English translation.

Chinese Office Action and Search Report regarding Application No. 201180043530.9; Date of Mailing: Aug. 12, 2014, with English translation.

Japanese Notification of Reasons for Refusal corresponding to Application No. 2012-532876; Date of Mailing: Feb. 10, 2015, with English translation.

* cited by examiner

FIG.9
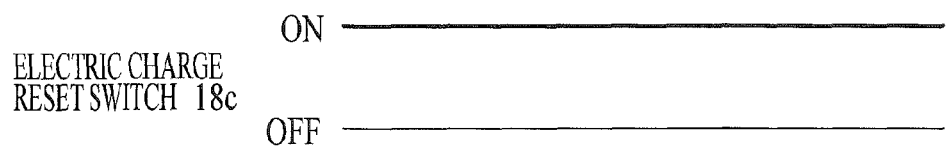
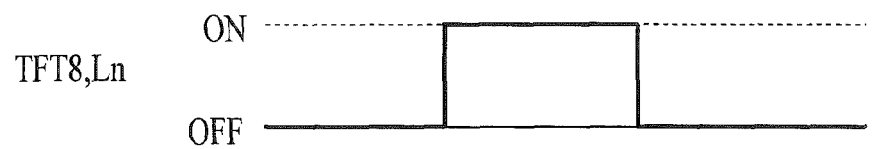
FIG.10
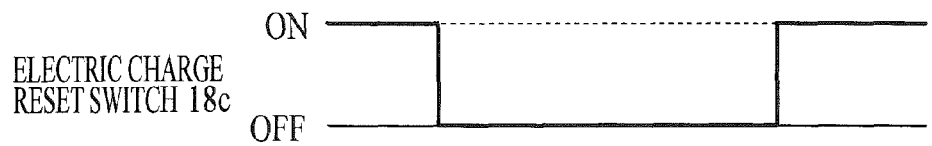
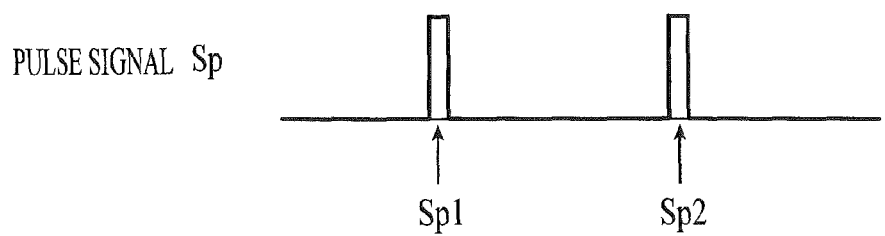
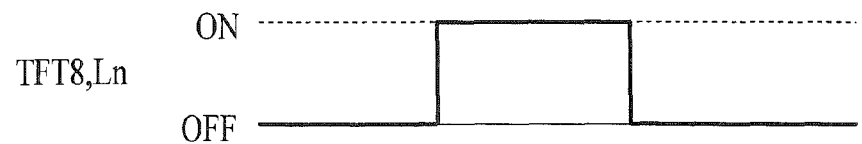

FIG.14
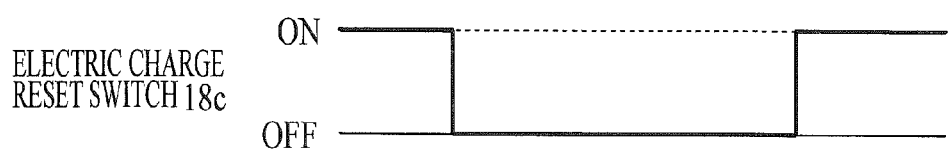
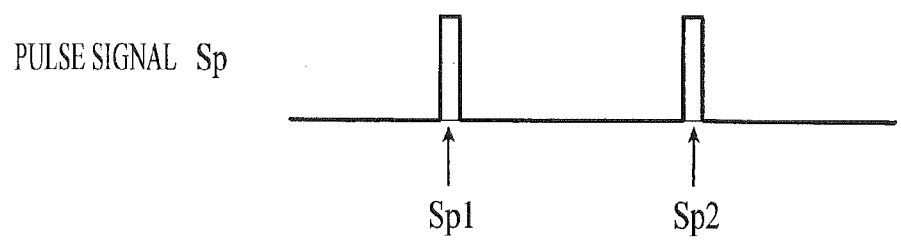
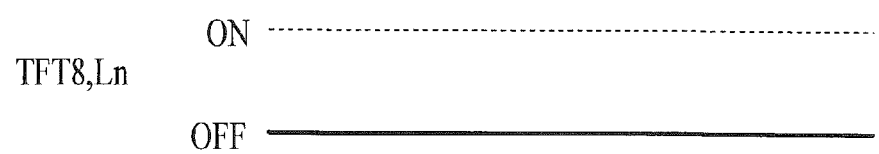

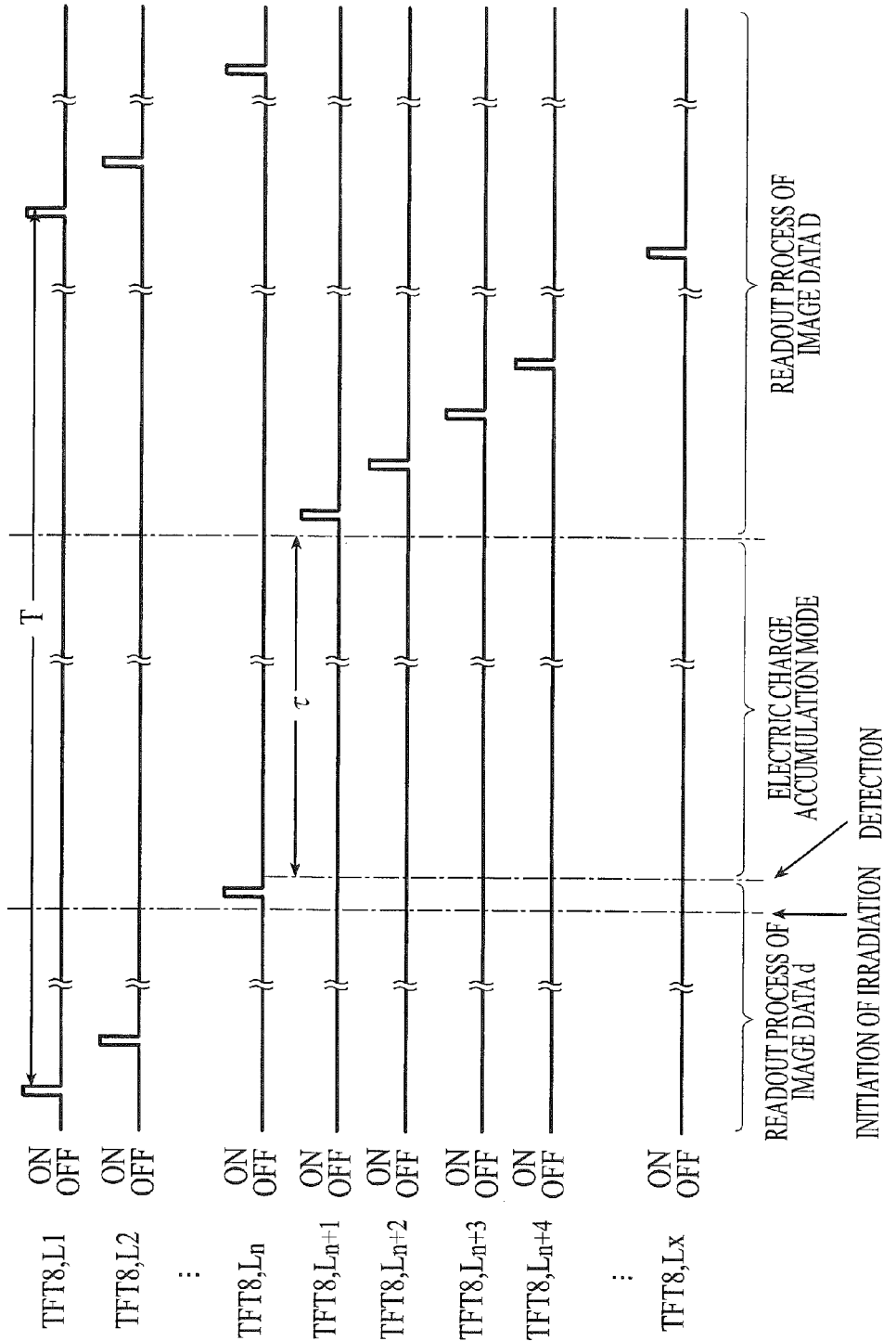

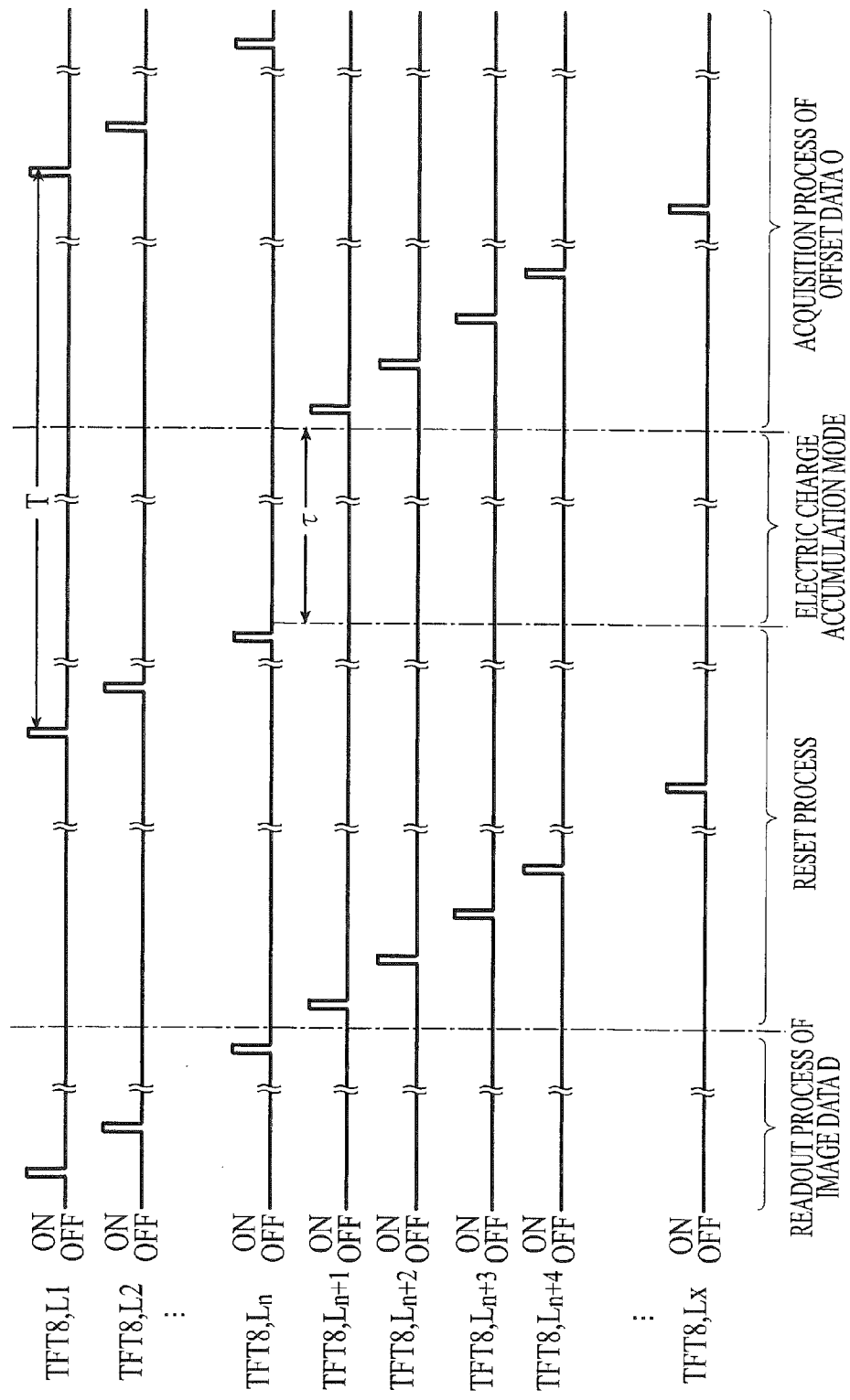

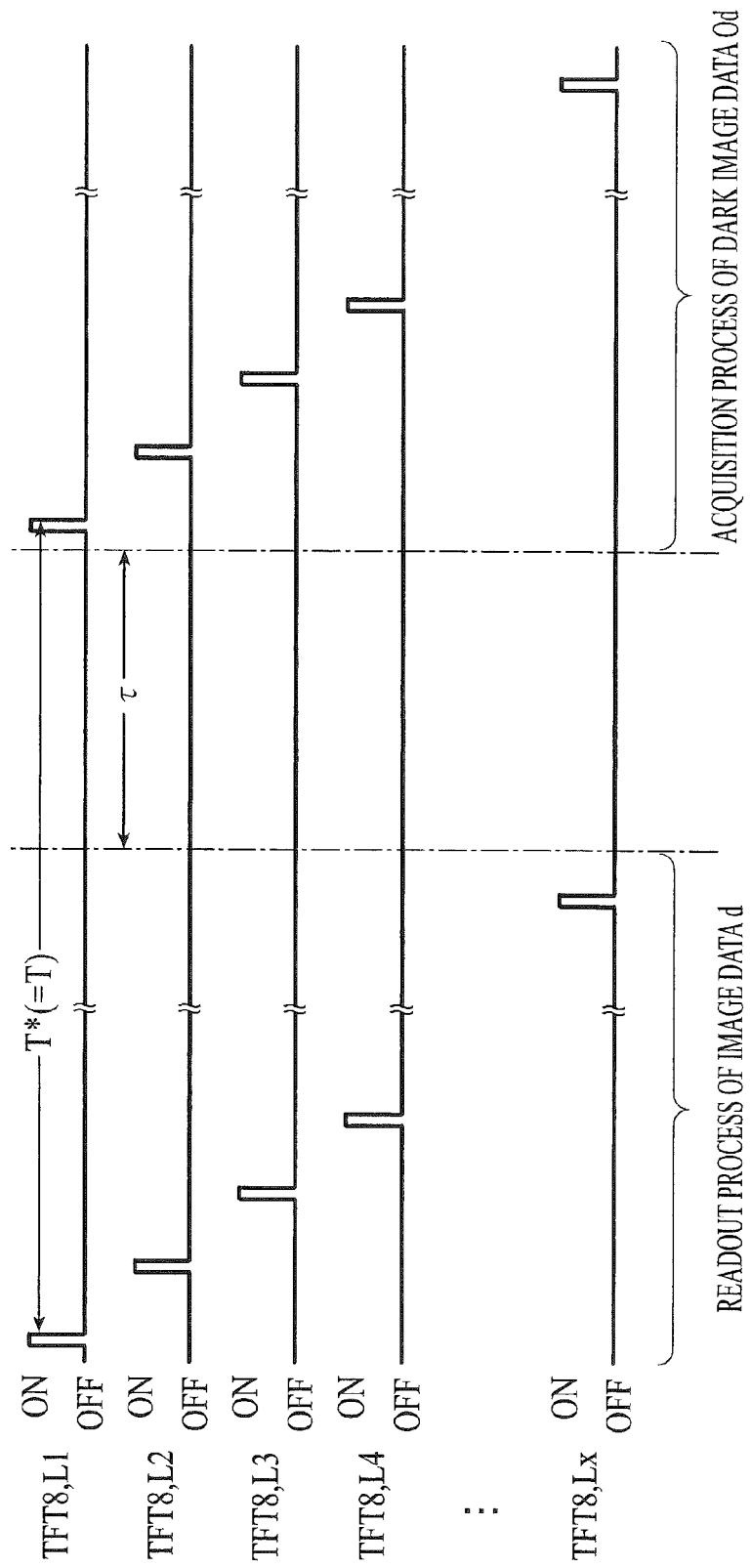

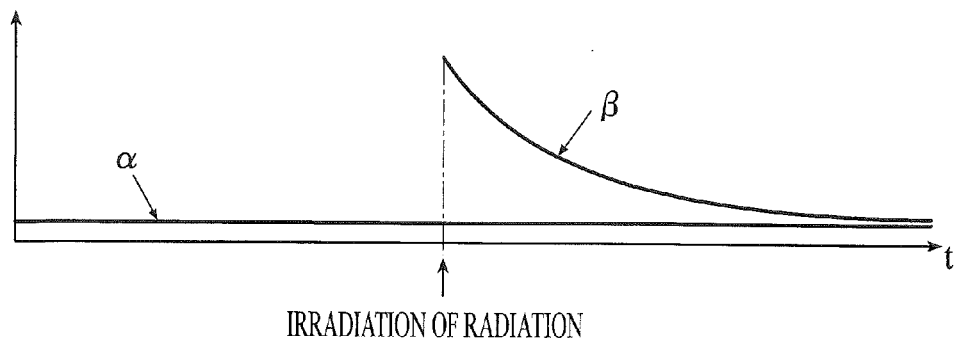
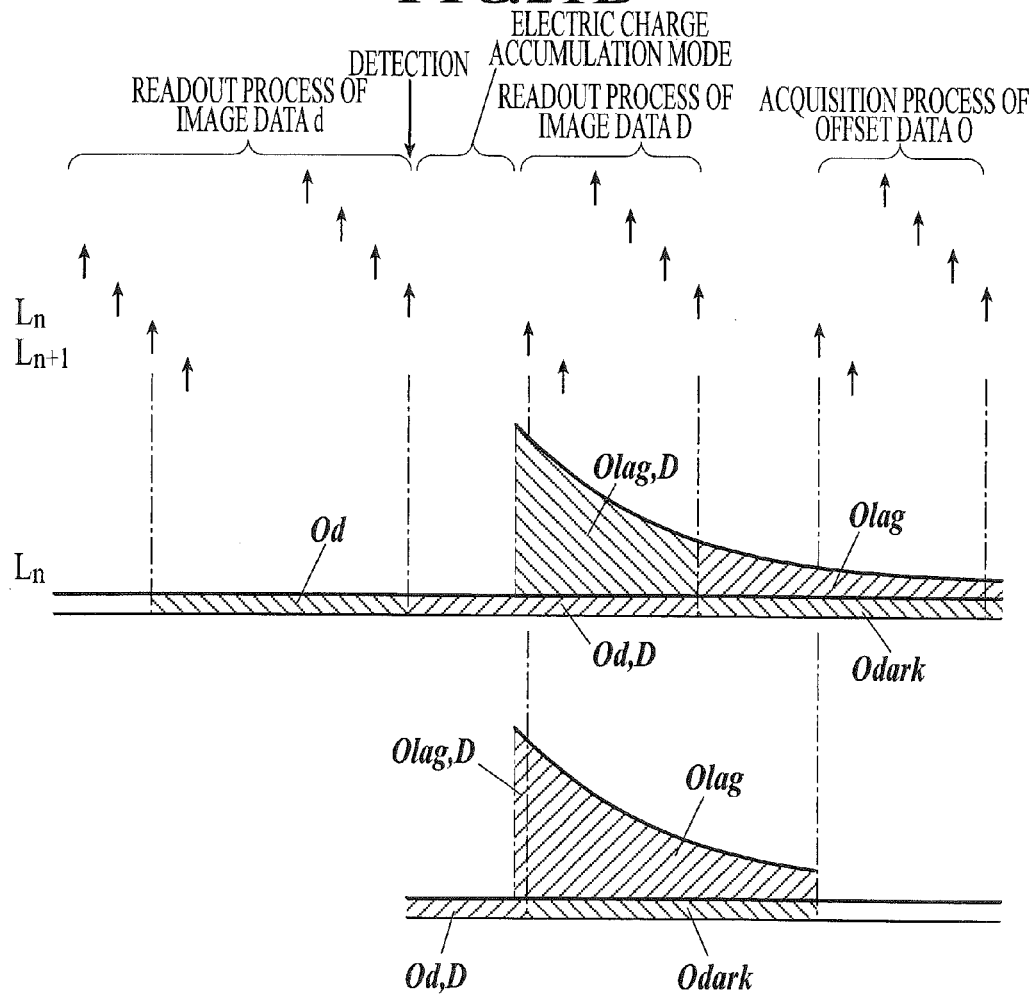

FORMER PHOTOGRAPHING    LATTER PHOTOGRAPHING

ELAPSED TIME t

ELAPSED TIME t

| IMAGE READOUT NUMBER | 1 | 2 | 3 | 4 | 5 | 6 | ... |
|---|---|---|---|---|---|---|---|
| y | y1 | y2 | y3 | y4 | y5 | y6 | ... |
| z | z1 | z2 | z3 | z4 | z5 | z6 | ... |

RADIATION IMAGE CAPTURING APPARATUS AND RADIATION IMAGE CAPTURING SYSTEM

CROSS REFERENCE TO RELATED APPLICATIONS

This is a U.S. National Stage of Application No. PCT/JP2011/054699, filed on 2 Mar. 2011. Priority under 35 U.S.C. §119(a) and 35 U.S.C. §365(b) is claimed from Japanese Application No. 2010-201502, filed 9 Sep. 2010, the disclosure of which is also incorporated herein by reference.

TECHNICAL FIELD

The present invention relates to a radiation image capturing apparatus and a radiation image capturing system and especially to a radiation image capturing apparatus and a radiation image capturing system for obtaining an image data without a lag.

BACKGROUND ART

A variety of kinds of radiation image capturing apparatus such as a so-called direct-type radiation image capturing apparatus which generates an electric charge according to the dose of the emitted radiation such as X-ray and converts the electric charge thus generated into an electric signal and a so-called indirect-type radiation image capturing apparatus which converts emitted radiation into an electromagnetic wave having other wavelength such as a visible light by way of a scintillator or the like and then generate an electric charge by a photoelectric conversion element such as a photodiode according to the energy of the converted and emitted electromagnetic wave to convert the electric charge into an electric signal has been developed. Note that in the present invention, a detecting element of the direct-type radiation image capturing apparatus and a photoelectric conversion element of the indirect-type radiation image capturing apparatus will be collectively called as a radiation detection element.

This type of radiation image capturing apparatus has been known as a flat panel detector (FPD) and has been conventionally formed in an integrated manner with a supporting board (or a Bucky device) (for example, refer to the Patent Document 1). However, in recent years, a portable-type radiation image capturing apparatus including a housing in which the radiation detection element and the like are stored has been developed and practically used (for example, refer to the Patent Documents 2 and 3).

In such a radiation image capturing apparatus, as shown in later-described FIG. 3 or FIG. 7, for example, radiation detection elements are aligned two-dimensionally (in a matrix manner) on a detecting part P and a switching element having a thin film transistor (hereinafter referred to as TFT) 8 is provided to each of the radiation detection elements 7. Then, in many cases, before capturing a radiation image, that is, before the radiation image capturing apparatus is irradiated with radiation emitted from a radiation generating device, on/off of the TFT 8 is appropriately controlled while reset process to release unnecessary electric charges left in each radiation detection element 7 is carried out.

Then, after the reset process of each radiation detection element 7 is completed, an off-state voltage is applied to the TFT 8 from a gate driver 15b of a scanning drive unit 15 via each scanning line 6 to cause all the TFTs 8 to be in an off-state. Then, when the radiation image capturing apparatus is irradiated with radiation emitted from the radiation generating device, electric charges according to the dose of the radiation are generated in each of the radiation detection elements 7 and accumulated in each of the radiation detection elements 7.

Then, in many cases, the radiation image capturing apparatus is configured so that after the irradiation of the radiation to the radiation image capturing apparatus (that is, after the radiation image capturing is carried out), as shown in FIG. 40, while each of the lines $L_1$ to $L_x$ of scanning lines 5 for applying an on-state voltage from the gate driver 15b of the scanning drive unit 15 for readout of signals are sequentially switched, the electric charges accumulated in each of the radiation detection elements 7 are read out and charge/voltage converted or the like by a readout circuit 17 so that the electric charges are read out as image data.

However, in such a configuration, it is necessary that an interface is precisely constructed between the radiation image capturing apparatus and the radiation generating device for irradiating the radiation image capturing apparatus with the radiation and when the irradiation is performed, the radiation image capturing apparatus must be in a condition where the radiation image capturing apparatus can accumulate the electric charges in the radiation detection elements 7. However, it is not necessarily easy to construct the interface between the devices. Moreover, if the irradiation is performed while the radiation image capturing apparatus is carrying out reset process of each of the radiation detection elements 7, the electric charges generated by the irradiation of the radiation are flown out from each of the radiation detection elements 7, thus causing such problems that the conversion ratio of the emitted radiation to the electric charges, that is, conversion ratio of the emitted radiation into the image data is lowered.

Therefore, various techniques for detecting irradiation with radiation by the radiation image capturing apparatus itself have been developed in recent years. As a part of such techniques, detection of irradiation with radiation by the radiation image capturing apparatus itself has been considered by use of, for example, techniques described in the Patent Document 4 or 5.

According to the Patent Documents 4 and 5, descriptions are made in which a radiation image capturing apparatus or a method for reading out image data by repeatedly carrying out the readout process of the image data from the radiation detection elements 7 while sequentially switching each of the lines $L_1$ to $L_x$ of the scanning drive line 5 for applying the on-state voltage from the gate driver 15b of the scanning drive unit 15 while the radiation image capturing apparatus is irradiated with radiation.

In this case, as shown in FIG. 41, if a period during which the on-state voltage is sequentially applied to each of the lines $L_1$ to $L_X$ of the scanning drive line 5 and each image data is read out from each of the radiation detection elements 7 which are targets for reading out the image data among all the radiation detection elements 7 aligned on the detecting part P is set to be 1 frame, the electric charges generated in the radiation detection elements 7 by the irradiation with the radiation is read out in a divided manner in each frame.

Therefore, image data read out for each frame from a frame in which irradiation with the radiation is started to a frame following a frame in which irradiation with the radiation has completed are added for each of the radiation detection elements 7 and thus the image data for each of the radiation detection elements 7 are reconstructed.

However, according to a study conducted by the inventors of the present invention, it became clear that following problems would arise if readout process of image data is continuously carried out for each frame after detecting irradiation with radiation, as in the invention described in the Patent Documents 4 and 5.

That is, in this case, as shown in FIG. 42, in a case where readout process of image data is carried out for each frame while on-state voltage is sequentially applied from the top scanning line 5 of the figure to each of the scanning lines 5 by the gate driver 15b, and, for example, irradiation is performed onto the shaded portion of FIG. 43, which is denoted by ΔT, while the on-state voltage is applied to the scanning line 5 in the shaded portion and the irradiation is completed. Here, FIG. 43 does not indicate that the irradiation is performed only to the shaded portion ΔT but also onto the entire area of the detecting part P.

Then, if the readout process of the image data is continued after subsequently to the above to carry out the readout process of the image data, and, as mentioned above, image data of each frame including this frame for two or three times are added to reconstruct image data for each radiation detection element 7, there appears unevenness in thickness of shade in the radiation image generated on the basis of thus reconstructed image data, as shown in FIGS. 44A and 44B.

That is, for example, in a radiation image generated based on each image data d which was reconstructed by irradiating the entire area of the detecting part P of the radiation image capturing apparatus uniformly with the same dose of radiation, when each of the reconstructed image data d is seen along a stretching direction of the signal line 6 (direction indicated by a vertical arrow in FIG. 44A), as shown in FIG. 44B, the image data d in an image area 5T corresponding to the scanning line 5 on which the on-state voltage was sequentially applied while radiation was irradiated (that is, the shaded portion ΔT of FIG. 43) has a larger value than the image data d of an image area A above the image area δT or an image area B below the image area δT.

Therefore, the portion of the image area δT of the radiation image becomes slightly thicker (that is, darker) compared to the image area A or image area B. Thus, it is known that there occurs a problem that despite uniform irradiation with radiation to the radiation image capturing apparatus, there appears unevenness in thickness.

This is not limited to a case where the entire area of the detecting part P of the radiation image capturing apparatus is uniformly irradiated with the same dose of radiation, but even in a case where irradiation is performed to the radiation image capturing apparatus through a subject, unevenness in thickness appears in the generated radiation image in a similar manner.

The reason why the image data d of image area δT becomes larger than the image data d in the image areas A and B is assumed as follows.

That is, as shown in FIG. 45, in a case where an image data di is read out from a radiation detection element $7_i$ when the on-state voltage is applied to a line Li of the scanning line 5, a small amount of electric charge q gradually leaks out from the radiation detection element 7, which is connected to another line L of the scanning line 5 to which an off-state voltage is applied simultaneously, via a TFT 8. Therefore, the image data di read out as the image data of the radiation detection element $7_i$ is actually an image data corresponding to a sum of the electric charge Q read out from the radiation detection element $7_i$ and the electric charge q leaked out from the other radiation detection element 7 via the TFT 8.

Moreover, in a case where readout process is carried out while irradiation is performed to the radiation image capturing apparatus 1, each of the TFT 8 is irradiated with the same radiation as the radiation image capturing apparatus 1, or the radiation thus emitted is converted into an electromagnetic wave by a scintillator and the electromagnetic wave is incident onto each of the TFT 8 to increase the amount of the electric charge q leaked out from the radiation detection element 7 via each of the TFT 8.

Therefore, in this case, the image data di readout as the image data of the radiation detection element $7_i$ becomes larger for the amount of each electric charge q leaked out from the other radiation detection element 7 connected to the same signal line 6. It is therefore assumed that the image data d of the image area δT becomes larger than the image data d in the image areas A and B.

However, if unevenness in thickness appears in the radiation image generated as above, it becomes difficult to see the radiation image. Moreover, for example, in a case where the radiation image is used for medical diagnosis, if the uneven portion and lesion location overlap on the radiation image, there is a possibility that the lesion location is missed or mistaken. In addition, it is not necessarily easy to correct the image data d of the image area δT which became larger than the image data d in the image areas A and B as shown in FIG. 44B.

Therefore, it is conceivable to configure a device which carries out readout process before start of the irradiation with radiation to the radiation image capturing apparatus by applying the invention described in the Patent Documents 4 and 5 and, instead of continuously carrying out the readout process while the radiation image capturing apparatus is irradiated with radiation as in the invention of the Patent Documents 4 and 5, stops carrying out the readout process of the image data d at the moment when irradiation with radiation is initiated.

If the device is configured as above, the image data d is read out from each of the radiation detection elements 7 connected to the scanning line 5 to which the on-state voltage is applied from the gate driver 15b of the scanning drive unit 15, the image data d having a significantly larger value than the image data d read out from each of the radiation detection elements 7 connected to the scanning line 5 to which the on-state voltage has been previously applied.

Therefore, it becomes possible to configure a device by use of this phenomenon that, for example, carries out the readout process of the image data d before irradiation with radiation to the radiation image capturing apparatus is started and in a case where the image data d thus read out suddenly increases and exceeds a threshold value, detects that irradiation with radiation started. Then, if initiation of irradiation with radiation is detected, the readout process of the image data d is stopped and the electric charges generated in each of the radiation detection elements 7 by the irradiation with radiation are caused to be accumulated in each of the radiation detection elements 7.

Moreover, though not shown, if an electric current detection unit is provided to a bias line 9 connecting each of the radiation detection elements 7 or to a wire connection 10 which bands them together (refer to later described FIG. 7 and the like) (for example, refer to the Patent Document 6), or if an electric current detection unit is provided to each of the scanning lines 5 or a wire 15c connecting the scanning drive unit 15 and the gate driver 15b, current value detected by the electric current detection unit suddenly increases when the radiation image capturing apparatus is irradiated with radiation.

Therefore, by use of the above, it becomes possible to configure a device which monitors the value of the electric current detected by the electric current detection unit and if the current value suddenly increases and, for example, exceeds a previously set threshold value, detects that the radiation image capturing apparatus has been irradiated with the radiation at that moment. Then, in this case also, when initiation of irradiation with radiation is detected, the readout process of the image data d (or in this case, reset process of each of the radiation detection elements 7 for causing each radiation detection element 7 to release the electric charges remaining in each of the radiation detection elements 7 may be applicable) it stopped and the electric charges generated in each of the radiation detection elements 7 by the irradiation with radiation are caused to be accumulated in each of the radiation detection elements 7.

Then, by configuring as mentioned above, it becomes possible to detect irradiation with radiation by the radiation image capturing apparatus itself in a case where it is impossible to construct an interface between the radiation image capturing apparatus and the radiation generating device.

Meanwhile, an image data readout after irradiation with radiation by the radiation image capturing apparatus as described above (for the purpose of distinction between the image data read out before photographing by the radiation image capturing apparatus described above, this data shall be referred to as the "image data D" hereinafter) includes the image data D attributable to the electric charge generated in each of the radiation detection elements 7 by the irradiation with radiation to the radiation image capturing apparatus as described above (hereinafter, this image data D shall be referred to as "true image data D*", meaning that this image data is attributable to the true electric charge generated by the irradiation with radiation).

However, other than the above, due to the thermal excitation or the like of each of the radiation detection elements 7 itself, a so-called dark electric charge is always generated in each of the radiation detection elements 7 and when the image data D is read out from each of the radiation detection elements 7, in addition to the true image data D*, an off-set data O which is an off-setting portion attributable to the dark electric charge is also read out. In other words, the image data D is expressed as a sum of the true image data D* and the off-set data O attributable to the dark electric charge, as in the following equation (1):

$$D = D^* + O \quad (1)$$

Then, because the data which should be acquired as image data is the true image data D* attributable to the true electric charge generated by the irradiation with radiation, the radiation image capturing apparatus is configured to obtain the off-set data O attributable to the dark electric charge under the same condition as photographing a radiation image but the radiation image capturing apparatus is not irradiated with radiation before or after photographing of the radiation image to calculate the true image data D* according to the following equation (2) obtained by modifying the above mentioned equation (1):

$$D^* = D - O \quad (2)$$

CITATION LIST

Patent Document 1: JP-A-09-73144
Patent Document 2: JP-A-2006-058124
Patent Document 3: JP-A-06-342099
Patent Document 4: JP-A-09-140691
Patent Document 5: JP-A-07-72252
Patent Document 6: JP-A-2009-219538

SUMMARY OF INVENTION

Technical Problem

However, according to a study by the inventors of the present invention, it was found out that if a radiation image capturing apparatus is irradiated with radiation, a so-called lag is generated due to the electric charge generated by irradiation with the radiation inside each of the radiation detection elements 7 and the lag is especially prone to be generated in a case where the radiation image capturing apparatus is irradiated with intense radiation.

Then, although the above-mentioned dark electric charge is removed from each of the radiation detection elements 7 by repeatedly carrying out the reset process of each of the radiation detection elements, even if the dark electric charges remain inside each of the radiation detection elements 7 without being read out at the time of the readout process of the image data D as the true image, the lag does not easily disappear even if the reset process is repeatedly carried out.

The reason why the lag does not easily disappear is assumed that part of electrons or holes generated inside the radiation detection element 7 due to the irradiation with radiation transits to a metastable energy level (metastable state) and a condition where mobility is lost inside the radiation detection element is kept for a relatively long period of time.

Then, the electrons or holes in this metastable energy state do not remain in this metastable energy level, but gradually transit to a conduction band assumed to have a higher energy level than the metastable energy with a certain probability so that mobility resurrects. However, the ratio of such transition is not necessarily high, and therefore it is assumed as the reason why the lags do not disappear easily. However, mechanism of generation and presence still remain unclear.

As mentioned above, if the lags are generated in each of the radiation detection elements 7 due to the irradiation with radiation, the off-set data O acquired by an acquisition process carried out after a radiation image is taken includes not only the offset data attributable to the dark electric charge (hereinafter, the offset data attributable to the dark electric charge shall be referred to as "offset data Odark") but Olag, a portion offset by lags. That is, the offset data O acquired after a radiation image is taken is a sum of the offset data Odark and the Olag, a portion offset by the lags, as shown in the following equation (3)

$$O = O\text{dark} + O\text{lag} \quad (3)$$

Moreover, the Olag, a portion offset by the lags, remain inside each of the radiation detection elements 7 even at the time of photographing of a radiation image to be carried out subsequently and is superimposed as a residual image on the image data D as the true image to be read out after the subsequently carried out photographing of the radiation image.

Moreover, according to the study by the inventors of the present invention, in a case where an interface is not constructed between the radiation image capturing apparatus and the radiation generating device and the radiation image capturing apparatus itself detects irradiation with radiation in a so-called unconnected condition between the radiation image capturing apparatus and the radiation generating device as described above, influence of the Olag, a portion offset by the lags, remains, and therefore even if the offset data O is subtracted from the image data D as the read out true data according to the above-mentioned equation (2), there are cases where appropriate true image data D* cannot be obtained. Note that, the causes and the like of this will be specifically explained later.

It is therefore desired that a radiation image capturing apparatus or a console which carries out image process based on the image data D transmitted from a radiation image capturing apparatus can appropriately remove the influence of the Olag, a portion offset by the lags, to acquire a true image data D* when carrying out image process of the image data D as the main image, and that the radiation image capturing apparatus can acquire various data necessary for acquisition of such appropriate true image data D*.

The present invention has been made in consideration of the above problems and is aimed at providing a radiation image capturing apparatus and a radiation image capturing system which can appropriately remove a portion offset by lags from an image data as a main image.

Means for Solving the Problems

In order to solve the above mentioned problems, a radiation image capturing apparatus according to an embodiment of the present invention comprises:
- a detection section that includes:
  - a plurality of scanning lines and a plurality of signal lines provided so as to cross with each other, and
  - a plurality of radiation detection elements aligned two-dimensionally in respective areas that are partitioned by the plurality of scanning lines and the plurality of signal lines;
- switching elements that discharge electric charges accumulated in the radiation detection elements to the signal lines when an on-state voltage is applied;
- a scanning drive unit that sequentially applies the on-state voltage to each of the scanning lines at a time of readout process for reading out image data from each of the radiation detection elements and sequentially applies the on-state voltage to each of the switching elements connected to each of the scanning lines;
- a readout circuit that converts the electric charges discharged from the radiation detection elements to the signal lines into the image data and reads out the image data at the time of readout process of the image data; and
- a control unit that controls at least the scanning drive unit and the readout circuit to cause them to carry out the readout process of the image data from each of the radiation detection elements,
  - wherein the control unit is configured to:
  - before radiation image capturing operation, cause the scanning drive unit to sequentially apply the on-state voltage to each of the scanning lines to carry out the readout process of the image data from the radiation detection element, acquire the image data read out in a condition where radiation is not irradiated as dark image data for each of the radiation detection elements, and at the same time detect initiation of radioactive irradiation at a time when the read out image data exceeds a threshold value,
  - cause the scanning drive unit to apply an off-state voltage to all the scanning lines when the initiation of radioactive irradiation is detected, and cause each of the switching elements to be turned off to shift to an electric charge accumulation mode,
  - cause the scanning drive unit to sequentially apply the on-state voltage to each of the scanning lines after the radioactive irradiation is over, and cause the readout circuit to sequentially carry out a readout operation to carry out the readout process of the image data as main image from each of the radiation detection elements,
  - further acquire the image data read out in a condition where radiation is not irradiated as offset data for each of the radiation detection elements after the readout process of the image data, and
  - correct the image data read out as main image by the radiation image capturing operation or the image data read out as main image by radiation image capturing operation carried out after the radiation image capturing operation based on offset lag part calculated for each of the radiation detection elements based on the offset data and the dark image data.

Further, a radiation image capturing system according to an embodiment of the present invention comprises:
- a radiation image capturing apparatus that includes:
  - a plurality of scanning lines and a plurality of signal lines provided so as to cross with each other;
  - a plurality of radiation detection elements that are two-dimensionally aligned in respective areas partitioned by the plurality of scanning lines and the plurality of signal lines;
  - switching elements that discharge electric charges accumulated in the radiation detection elements to the signal lines when an on-state voltage is applied;
  - a scanning drive unit that sequentially applies the on-state voltage to each of the scanning lines at a time of readout process for reading out image data from each of the radiation detection elements and sequentially applies the on-state voltage to each of the switching elements connected to each of the scanning lines;
  - a readout circuit that converts the electric charges discharged from the radiation detection elements to the signal lines into the image data and reads out the image data at the time of readout process of the image data;
  - a control unit that controls at least the scanning drive unit and the readout circuit to cause them to carry out the readout process of the image data from each of the radiation detection elements;
  - a communication unit that transmits and receives information to/from an external device,
  - wherein the control unit is configured to:
  - before the radiation image capturing operation, cause the scanning drive unit to sequentially apply the on-state voltage to each of the scanning lines to carry out the readout process of the image data from the radiation detection elements, acquire the image data read out in a condition where radiation is not irradiated as dark image data for each of the radiation detection elements, and at the same time detect initiation of radioactive irradiation at a time when the read out image data exceeds a threshold value,
  - cause the scanning drive unit to apply an off-state voltage to all the scanning lines when initiation of radioactive irradiation is detected, turn each of the switching elements off, and shift to electric charge accumulation mode,
  - cause the scanning drive unit, after radioactive irradiation is over, to sequentially apply the on-state voltage to each of the scanning lines and cause the readout circuit to carry out a readout operation to carry out the readout process of the image data as main image from each of the radiation detection elements, and
  - further acquire the image data read out in a condition where radiation is not irradiated after the readout process of the image data, as offset data for each of the radiation detection elements; and
- a console that corrects the image data as main image read out by the radiation image capturing operation or the image data read out as main image by radiation image capturing operation carried out by use of the radiation image capturing apparatus after the radiation image capturing operation based on offset lag part calculated for each of the radiation detection elements based on the offset data transmitted from the radiation image capturing apparatus and the dark image data.

Advantageous Effects of Invention

According to the radiation image capturing apparatus and the radiation image capturing system according to preferred embodiments of the present invention, a control unit or a console of the radiation image capturing apparatus subtracts the dark image data from the offset data to calculate the portion offset by lags included in the offset data for each of the radiation detection elements. Then based on the offset portion thus calculated, the portion offset by lags included in the image data as the main image is estimated and the portion offset by lags is subtracted from the main image data read out by the radiation image capturing operation or from the image data as the main image which was read out by radiation image capturing operation carried out after the radiation image capturing operation to modify the image data as the main data.

Therefore, it becomes possible to appropriately remove the portion offset by lags which is included in the image data as the main image. Moreover, it also becomes possible to generate a final radiation image based on the main image data and the like from which the influence of lags is appropriately removed. Therefore, it becomes possible to remove the influence of lags in the middle of photographing of a final radiation image and to improve the image quality of the final radiation image.

BRIEF DESCRIPTION OF DRAWINGS

FIG. 9 is a timing chart showing on/off timing of an electric charge resetting switch and a TFT in the readout process by each of radiation detection elements.

FIG. 10 is a timing chart showing on/off timing of an electric charge resetting switch, a pulse signal, and a TFT in the readout process of image data.

FIG. 14 is a timing chart showing on/off timing of an electric charge resetting switch and a TFT in the readout process of leaked data.

FIG. 18 is a timing chart showing timing for transition from readout process of image data before photographing of a radiation image to an electric charge accumulation mode and for applying the on-state voltage to each scanning line in the readout process of main image data.

FIG. 19 is a timing chart showing timing for applying the on-state voltage to each scanning line in an acquisition process of offset data.

FIG. 20 is a timing chart showing timing for applying the on-state voltage to each scanning line in an acquisition process of dark image data carried out by setting the same period of time required for the electric charge accumulation mode, during which the off-state voltage is applied.

FIG. 21A is a view illustrating the dark electric charges generated by a certain ratio and lags reducing exponentially per unit time.

FIG. 21B is an image view illustrating offset portion by lags included in dark image data, the main data, and the offset data.

DESCRIPTION OF EMBODIMENTS

Hereinafter, embodiments of the radiation image capturing apparatus according to the present invention will be explained with reference to the drawings.

Note that an explanation will be given below of a case where the radiation image capturing apparatus is an indirect type radiation image capturing apparatus which includes a scintillator or the like and an emitted radiation is converted into an electromagnetic wave having other wavelength such as a visible light to obtain an electric signal. However, the present invention is also applicable to a direct type radiation image capturing apparatus. Moreover, although an explanation will be given of a case where the radiation image capturing apparatus is a portable type device, the present invention is also applicable to a case where the radiation image capturing apparatus is formed integrally with a supporting board (that is, so-called a dedicated machine).

First Embodiment

Figure 1:
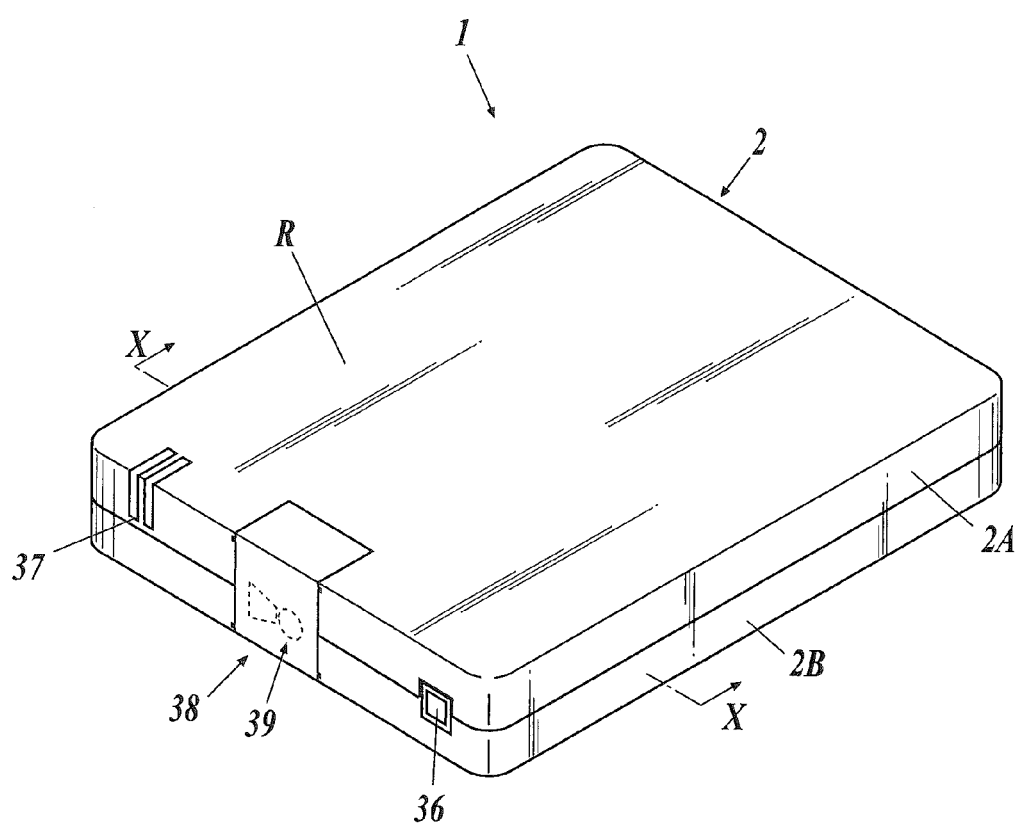
FIG. 1 is a perspective view showing a radiation image capturing apparatus according to each embodiment of the present invention.
Figure 2:
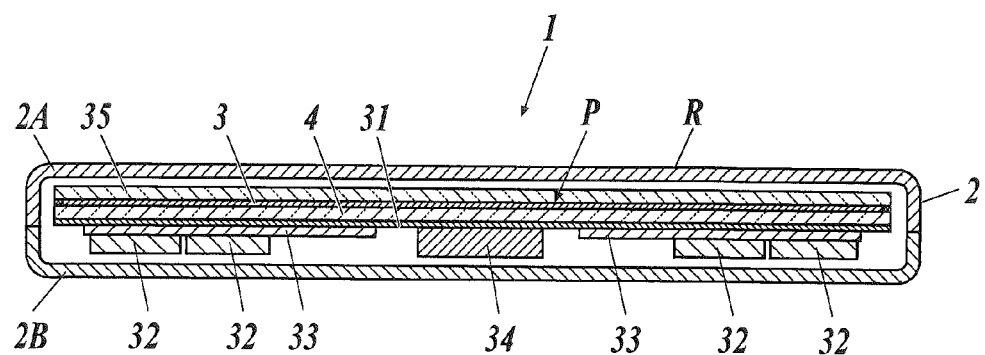
FIG. 2 is a cross-sectional view taken along X-X line in FIG. 1.

FIG. 1 is an external perspective view showing a radiation image capturing apparatus according to the present embodiment and FIG. 2 is a cross-sectional view taken along an X-X line of FIG. 1. A radiation image capturing apparatus 1 according to the present invention is configured by storing, as shown in FIG. 1 or 2, a scintillator 3, a substrate 4, or the like in a case 2.

A radiation incidence surface R of the case 2 is formed with a material such as a carbon board or plastic, which, at least allows radiation to transmit. Here, in FIG. 1 or 2, a case where the case 2 is a so-called rectangular lunchbox type one having a front board 2A and a back board 2B is shown. However, the case 2 may be integrally prismatically shaped to be a so-called mono-cock type.

Moreover, as shown in FIG. 1, on a side surface portion of the case 2, a power source switch 36, an indicator 37 including an LED or the like, a lid member 38 for exchange or the like of a battery 41 (refer to later-described FIG. 7), and the like are provided. In addition, in the present embodiment, an antenna device 39 as a communication unit for receiving and transmitting necessary information by wireless between the case 2 and an external device such as a later-described console 58 (refer to later-described FIG. 12) is embedded on a side surface part.

Note that the position for the antenna device 39 is not limited to the side surface part of the lid member 38 but may be provided at an arbitrary position of the radiation image capturing apparatus 1. Moreover, the number of the antenna device 39 to be provided is not limited to one and a plurality of antenna device 39 may be provided. Furthermore, it is also possible to transmit and receive an image data d or the like between an external device by a wire and in such a case, a connection terminal or the like for connecting the devices by plugging in a cable is provided on a side surface part or the like of the radiation image capturing apparatus 1.

As shown in FIG. 2, in the case 2, a base 31 is provided on a lower side of the substrate 4 via a lead thin plate which is not shown and a PCB substrate 33 on which electronic components 32 or the like are provided, a buffer member 34, or the like are provided to the base 31. Note that in this embodiment, a glass substrate 35 is provided to the substrate 4 or radiation incidence surface R of the scintillator 3 for protection.

The scintillator 3 is provided to face a later-described detection section P of the substrate 4. A scintillator which mainly includes a fluorescence material as a main component and upon reception of incident radiation, converts the radiation into an electromagnetic wave having a wavelength of between 300 and 800 nm, in other words, an electromagnetic wave mainly having a visible light, and outputs the electromagnetic wave, is used as the scintillator 3.

Figure 3:
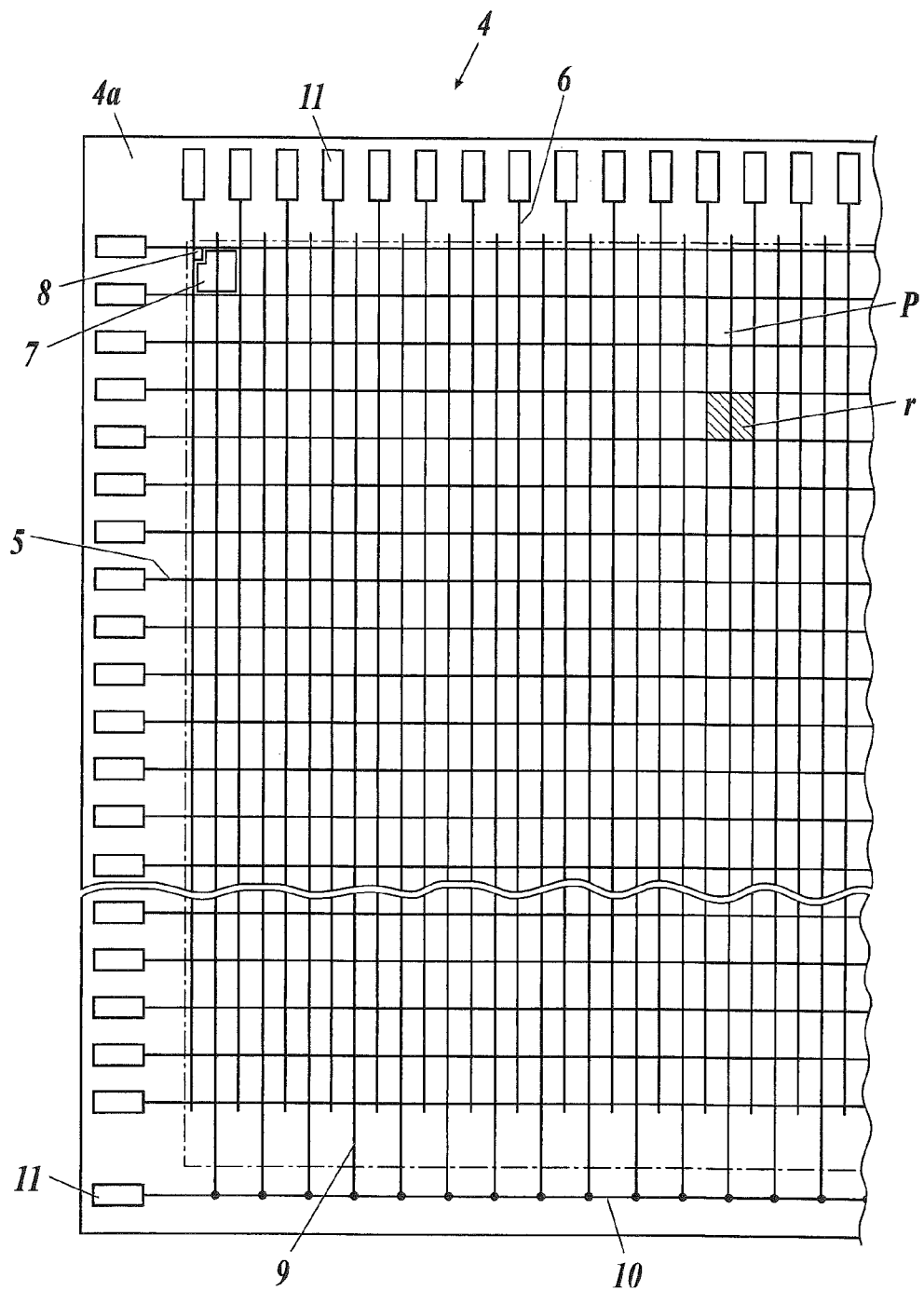
FIG. 3 is a plan view showing configuration of a substrate of the radiation image capturing apparatus.

The substrate 4 includes a glass substrate in the present embodiment and, as shown in FIG. 3, a plurality of scanning lines 5 and a plurality of signal lines 6 are provided to cross each other over a surface 4a of the substrate 4 facing the scintillator 3. In each of small regions r divided by the plurality of scanning lines 5 and the plurality of signal lines 6 on the surface 4a of the substrate 4, a radiation detection element 7 is provided.

An entire region r, which is each of the small regions r thus divided by the scanning lines 5 and the signal lines 6, and to which two-dimensionally aligned a plurality of radiation detection elements 7 are provided, that is, the region shown by dashed-dotted lines in FIG. 3, is assumed to be a detecting part P.

In the present embodiment, a photo diode is used as the radiation detection element 7. However, for example, a photo transistor or the like may be used. Each of the radiation detection elements 7 is, as shown in the enlarged views of FIG. 3 or FIG. 4, connected to a source electrode 8s of a TFT 8. Moreover, a drain electrode 8d is connected to the signal line 6.

Then, the TFT 8 is brought into an on-state when an on-state voltage is applied to the scanning line 5 to which the TFT 8 is connected and an on-state voltage is applied to a gate electrode 8g via the scanning line 5 by a later described scanning drive unit 15 so that electric charges accumulated in the radiation detection element 7 are released to the signal line 6. Moreover, the TFT 8 is brought into an off-state when an off-state voltage is applied to the scanning line 5 to which the TFT 8 is connected and an off-state voltage is applied to a gate electrode 8g via the scanning line 5 so that release of the electric charges from the radiation detection element 7 to the signal line 6 is stopped and the electric charges can be accumulated in the radiation detection element 7.

Figure 4:
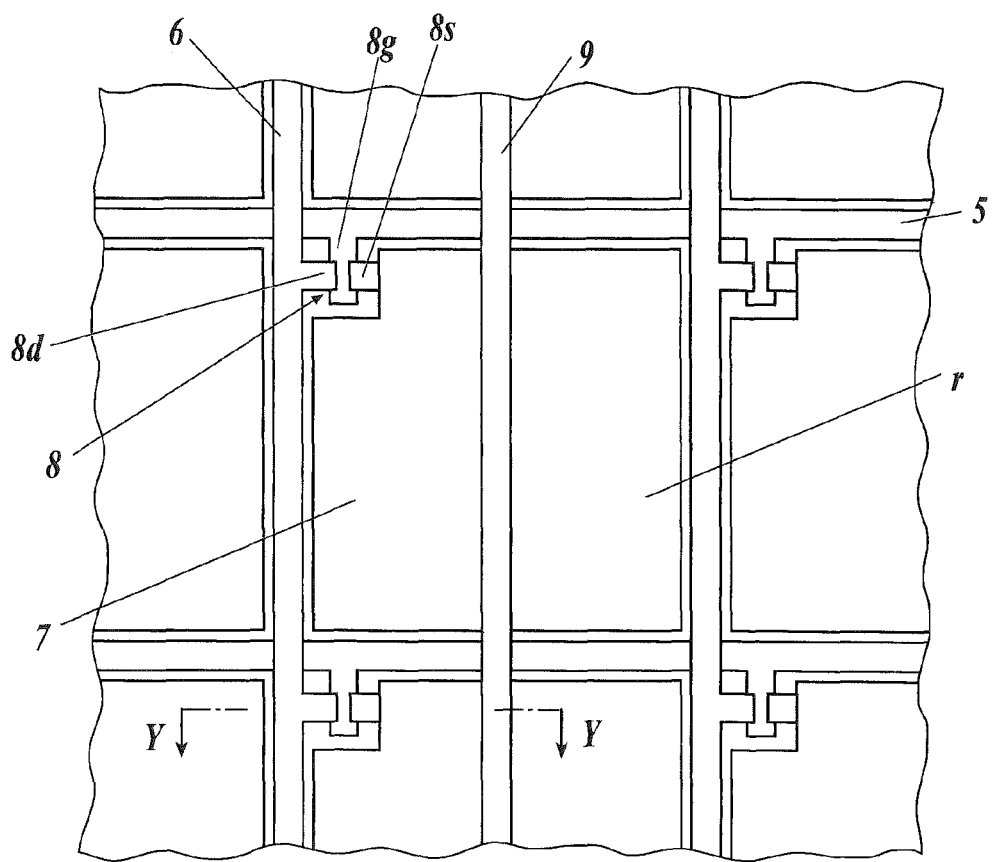
FIG. 4 is an enlarged view showing configuration of a radiation detection element, TFT, and the like formed on a small area on the substrate of FIG. 3.
Figure 5:
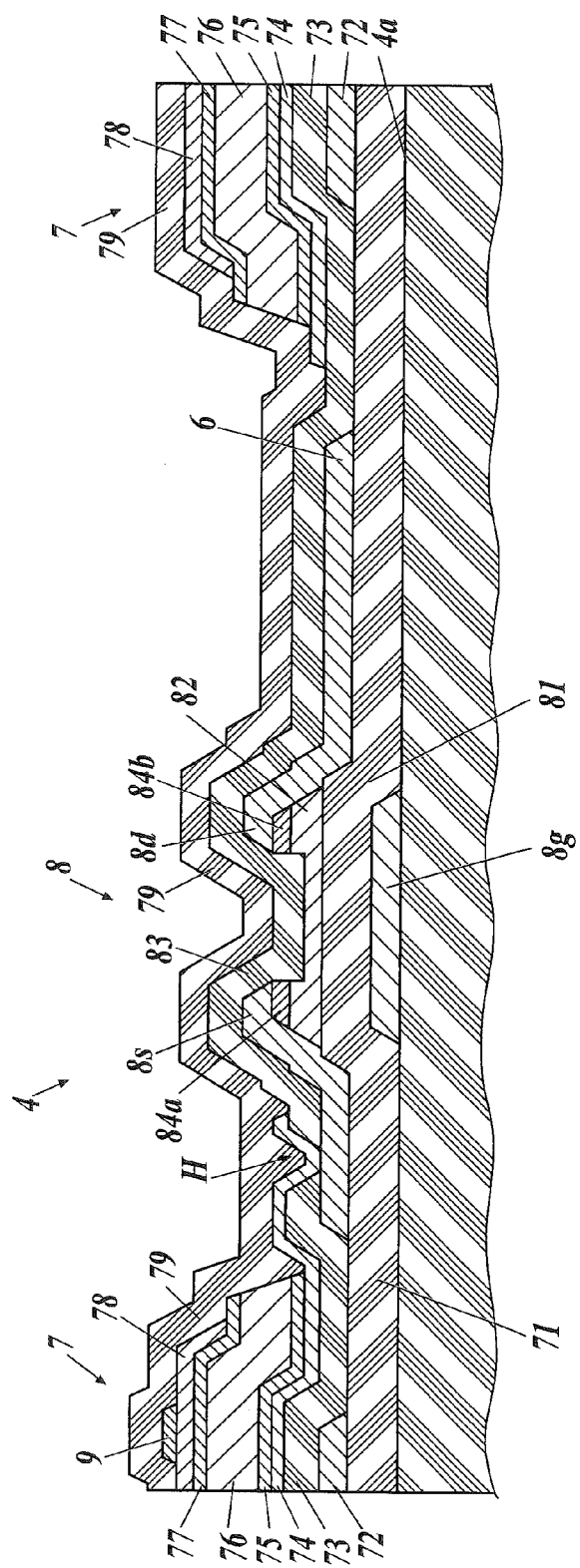
FIG. 5 is a cross-sectional view taken along Y-Y line in FIG. 4.

Here, the structure of the radiation detection element 7 and the TFT 8 of the present embodiment will be briefly explained by use of a cross-sectional view shown in FIG. 5. FIG. 5 is a cross-sectional view taken along a Y-Y line in FIG. 4.

The gate electrode 8g including Al, Cr, or the like is laminated and formed with the scanning line 5 on the surface 4a of the substrate 4 in an integrated manner. On the gate electrode 8g and an upper portion of the gate electrode 8g on a gate insulating layer 81 including silicon nitride ($SiN_x$) or the like laminated on the gate electrode 8g and the surface 4a, a source electrode 8s connected with a first electrode 74 of the radiation detection element 7 and a drain electrode 8d formed with the signal line 6 in an integrated manner are laminated and formed via a substrate layer 82 including hydrogenated amorphous silicon (a-Si) or the like.

The source electrode 8s and the drain electrode 8d are separated by a first passivation layer 83 including silicon nitride ($SiN_x$) or the like and the first passivation layer 83 covers both of the electrodes 8s and 8d from above. Moreover, between the substrate layer 82 and the source electrode 8s or the drain electrode 8d, ohmic contact layers 84a and 84b formed in an n-shape by doping a VI series element to hydrogenated amorphous silicon are respectively laminated. Thus, the TFT 8 is formed.

Moreover, in the radiation detection element 7, Al, Cr, or the like is laminated on an insulating layer 71 formed in an integrated manner with the gate insulating layer 81 on the surface 4a of the substrate 4 to form an auxiliary electrode 72 and on the auxiliary electrode 72, a first electrode 74 including Al, Cr, Mo, or the like is laminated with an insulating layer 73 formed integrally with the first passivation layer 83 in between. The first electrode 74 is connected with the source electrode 8s via a hole H formed in the first passivation layer 83. Note that the auxiliary electrode 72 does not need to be provided.

On the first electrode 74, an n layer 75 formed to have an n-shape by doping a VI series element to hydrogenated amorphous silicon, an i layer 76 which is a converting layer including hydrogenated amorphous silicon, and a p layer 77 formed to have a p-shape by doping a III series element to hydrogenated amorphous silicon, are laminated sequentially from the bottom and formed.

Then, when a radiation image is photographed, radiation emitted onto the radiation image capturing apparatus 1 is incident from the radiation incidence surface R of the case 2 and converted into an electromagnetic wave such as a visible light by the scintillator 3. When the electromagnetic wave thus converted is incident from the upper direction of the figure, the electromagnetic wave reaches the i layer 76 of the radiation detection element and an electron-hole pair is generated in the layer 76. The radiation detection element 7 thus converts the electromagnetic wave emitted from the scintillator 3 into electric charges (an electron-hole pair).

Moreover, a second electrode 78 being a transparent electrode such as an ITO is laminated and formed on the p layer 77 so that the irradiated electromagnetic wave reaches the i layer 76. In the present embodiment, the radiation detection element 7 is thus formed. Note that the order of the p layer 77, the i layer 76, the n layer 75 may be reversed. Moreover, a case where a so-called pin-type radiation detection element, in which the p layer 77, the i layer 76, and the n layer 75 are sequentially laminated to be formed, is used has been explained in the present embodiment. However, the present invention is not limited thereto.

On an upper surface of the second electrode 78 of the radiation detection element 7, a bias line 9 for applying a bias voltage to the radiation detection element 7 is connected via the second electrode 78. Note that the second electrode 78 and the bias line 9, the first electrode 74 stretching on the TFT 8 side, the first passivation layer 83 of the TFT 8, or the like, in other words, the upper surface of the radiation detection element 7 and the TFT 8 are covered with the second passivation layer 79 including silicon nitride ($SiN_x$) or the like from above.

As shown in FIG. 3 or FIG. 4, one bias line 9 is connected to a plurality of radiation detection elements 7 respectively aligned on a line and each of the bias lines 9 is provided to be parallel to each of the signal lines 6. Moreover, the bias lines 9 are tied at a position outside of the detecting part P of the substrate 4 by the wire connection 10.

In the present embodiment, as shown in FIG. 3 each of the scanning lines 5, signal lines 6, and the wire connection 10 of the bias lines 9 are connected to an input/output terminal (also called a pad) 11 provided in the vicinity of the substrate 4. To each input/output terminal 11, a chip on film (COF) 12, in which a chip such as a gate IC 12a which configures the gate driver 15 of the scanning drive unit 15 is incorporated, is connected via an anisotropic conductive adhesive material 13 such as an anisotropic conductive film or an anisotropic conductive paste.

Figure 6:
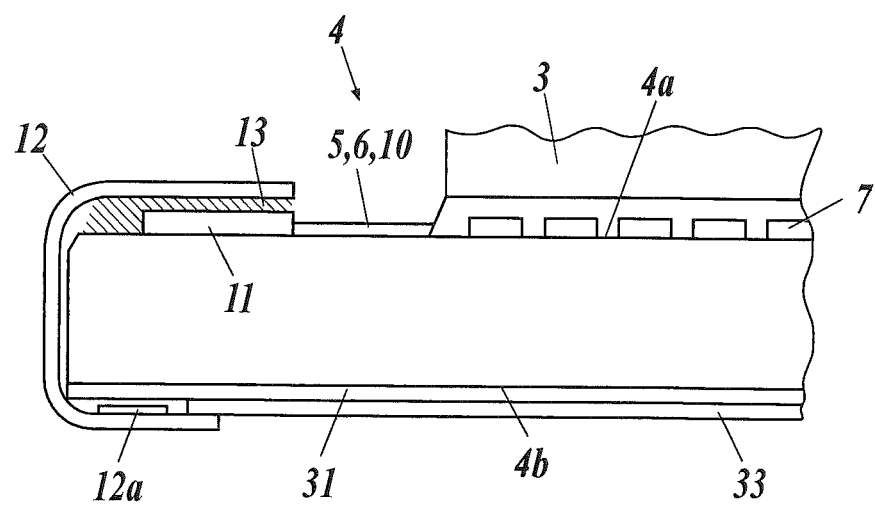
FIG. 6 is a side elevation view illustrating a substrate to which a COF or a PCB substrate or the like is attached.

Moreover, the COF 12 can be pulled to aback surface 4b of the substrate 4 and connected to the above-mentioned PCB substrate 33 on the back surface 4b side. Thus, the substrate 4 of the radiation image capturing apparatus 1 is formed. Note that in FIG. 6, an electronic component 32 or the like is not shown.

Figure 7:
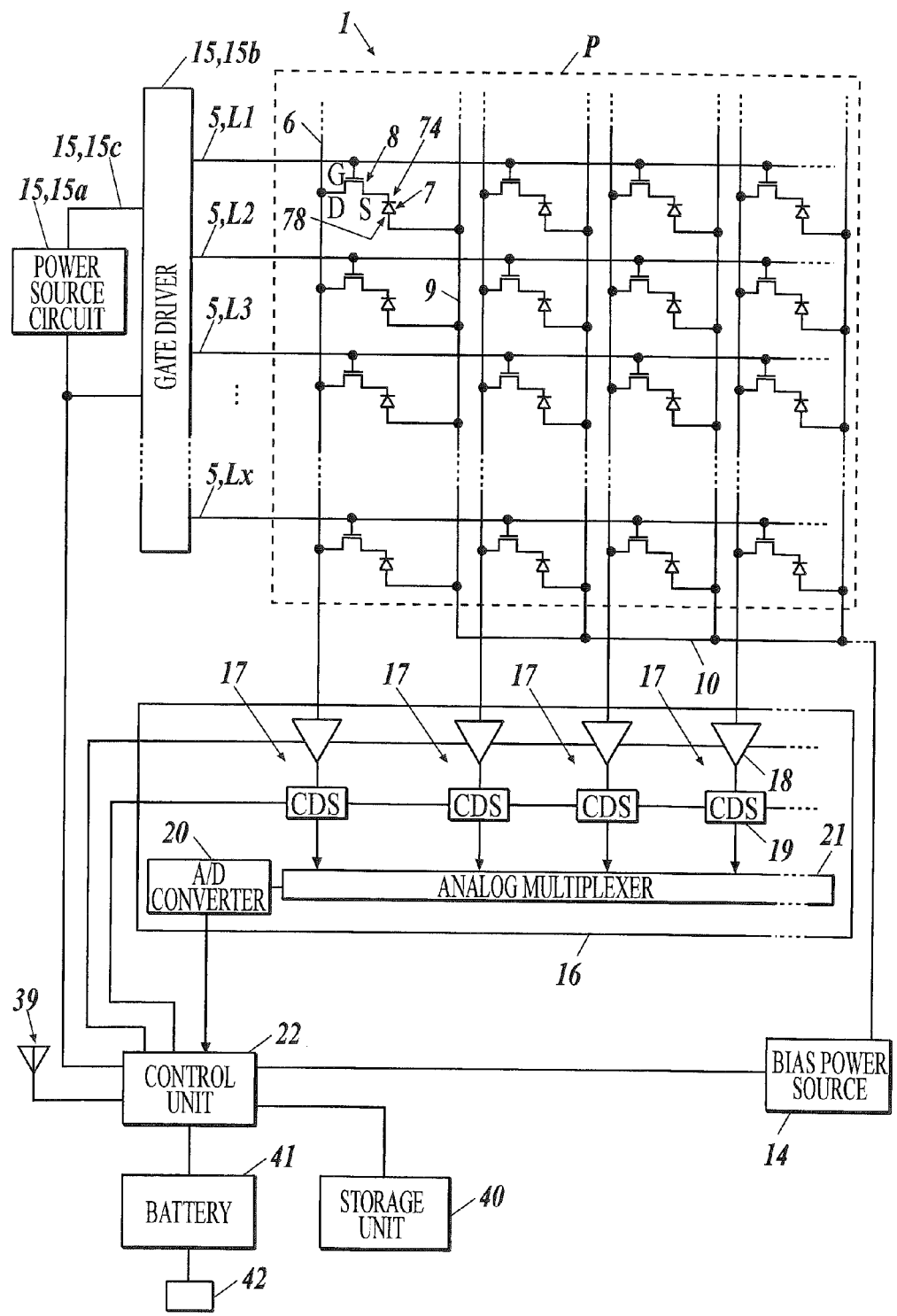
FIG. 7 is a block diagram showing an equivalent circuit of the radiation image capturing apparatus.

Here, circuit configuration of the radiation image capturing apparatus 1 will be explained. FIG. 7 is a block diagram showing an equivalent circuit of the radiation image capturing apparatus 1 according to the present embodiment and FIG. 8 is a block diagram showing an equivalent circuit for one pixel configuring the detecting part P.

As mentioned above, the second electrode 78 of each of the radiation detection elements 7 of the substrate 4 is connected with the bias line 9 and each of the bias lines 9 is tied by the wire connection 10 and connected to a bias power source 14. The bias power source 14 applies a bias voltage to the second electrode 78 of each of the radiation detection elements 7 via the wire connection 10 and each of the bias lines 9. Moreover, the bias power source 14 is connected to a later-described control unit 22 and the bias voltage applied to each of the radiation detection elements 7 by the bias power source 14 is controlled by the control unit 22.

Figure 8:
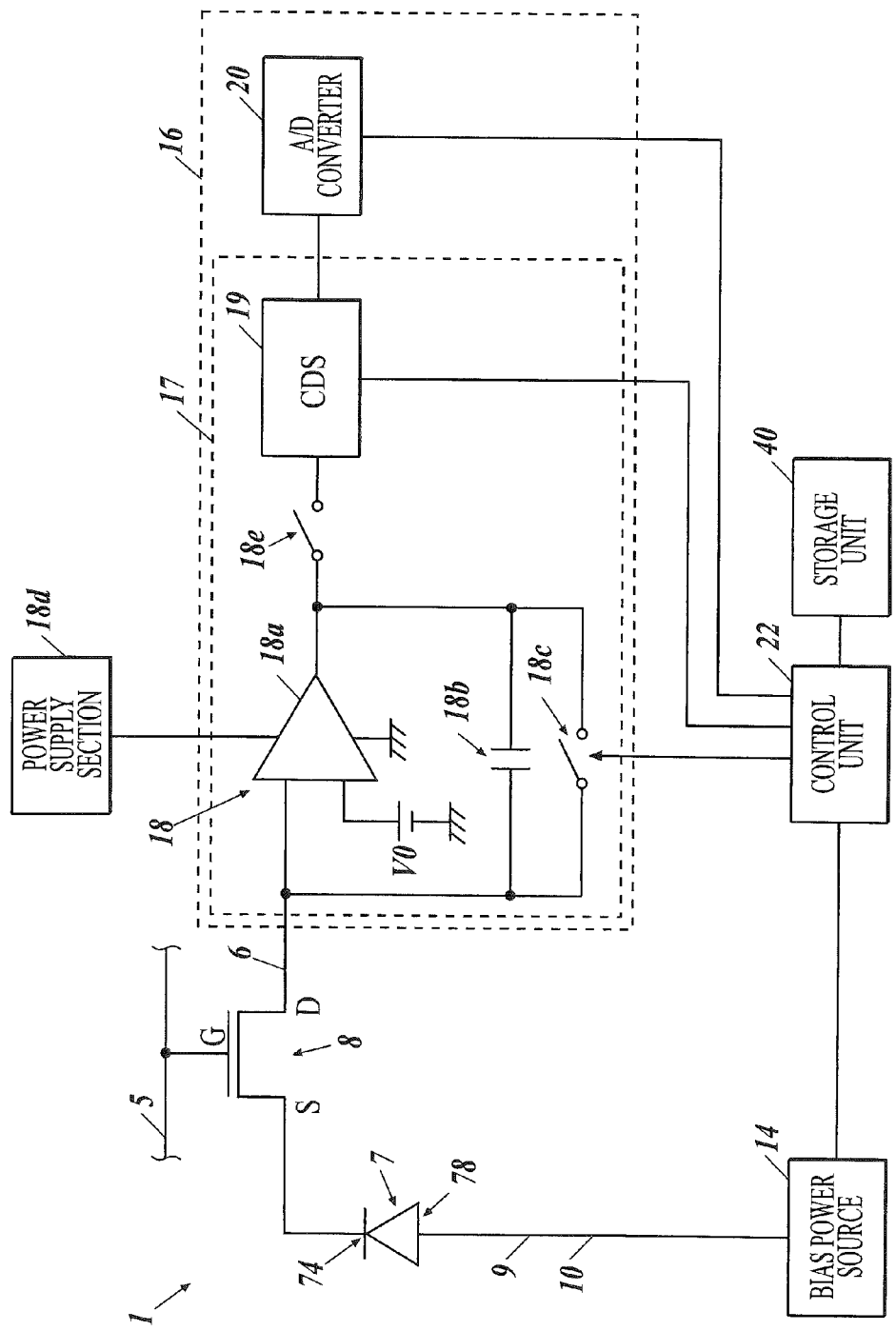
FIG. 8 is a block diagram showing an equivalent circuit for one pixel configuring a detecting part.

As shown in FIG. 7 or 8, in the present embodiment, a voltage, which is lower than the voltage applied to the first electrode 74 side of the radiation detection element 7, is applied to the second electrode 78 of the radiation detection element 7 via the bias line 9 as the bias voltage, as understood from the bias line 9 connected to the p layer 77 side of the radiation detection element 7 (refer to FIG. 5) via the second electrode 78.

The first electrode 74 of each of the radiation detection elements 7 is connected to the source electrode 8s of the TFT 8 (which is shown as S in FIG. 7 and FIG. 8) and the gate electrodes 8g of the TFT 8 (which is shown as G in FIG. 7 and FIG. 8) is respectively connected to lines $L_1$ to $L_x$ of the scanning line 5 stretching from the gate driver 15b of the later-described scanning drive unit 15. In addition, drain electrodes 8d of each TFT 8 (which is shown as D in FIG. 7 and FIG. 8) is respectively connected to the signal lines 6.

The scanning drive unit 15 includes a power circuit 15a for providing an on-state voltage and an off-state voltage to the gate driver 15b via a wire 15c and the gate driver 15b for switching the voltage to be applied to each of the lines $L_1$ to $L_x$ of the scanning line 5 to switch between on-state and off-state of each of the TFT 8.

In the present embodiment, as described later, the scanning drive unit 15 sequentially applies an on-state voltage to each of the lines $L_1$ to $L_x$ of the scanning line 5 according to an instruction from the control unit 22, or maintains a condition where an off-state voltage is applied to all the lines $L_1$ to $L_x$ of the scanning line 5.

Moreover, the TFT 8 which is a switching element causes the radiation detection element 7 to release accumulated electric charges when an on-state voltage is applied to the gate electrode 8g from the gate driver 15b of the scanning drive unit 15 via the scanning line 5 and when an off-state voltage is applied to the gate electrode 8g, stops release of electric charges from the radiation detection element 7 to accumulate generated electric charges in the radiation detection element 7.

As shown in FIG. 7 or FIG. 8, the signal lines 6 are respectively connected to readout circuits 17 that are formed in readout ICs 16, respectively. Note that one readout circuit 17 is provided for one signal line 6 in the readout IC 16.

The readout circuit 17 includes an amplifier circuit 18, a correlated double sampling circuit 19, and the like. In the readout IC 16, an analog multiplexer 21 and an A/D converter 20 are further provided. Note that in FIG. 7 or FIG. 8, the correlated double sampling circuit 19 is shown as CDS. Moreover, the analog multiplexer 21 is omitted in FIG. 8.

In the present embodiment, the amplifier circuit 18 includes a charge amplifier circuit, in which an operational amplifier 18a is provided and a capacitor 18b and an electric charge resetting switch 18c are connected in parallel to the operational amplifier 18a. Moreover, the amplifier circuit 18 is connected to a power supply section 18d for supplying power to the amplifier circuit 18. In addition, a switch 18e which is turned on/off in conjunction with the electric charge resetting switch 18c is provided between the operational amplifier 18a and the correlated double sampling circuit 19.

The signal line 6 is connected to an inverting input terminal on an input side of the operational amplifier 18a of the amplifier circuit 18 and to the non-inverting input terminal on the input side of the amplifier circuit 18, a reference potential $V_0$ is applied. Note that the reference potential $V_0$ is set to have an appropriate value and, in the present embodiment, for example, 0[V] is to be applied.

Moreover, the electric charge resetting switch 18c of the amplifier circuit 18 is connected to the control unit 22 and on/off of the switch is controlled by the control unit 22. When the electric charge resetting switch 18c is in an on-state, the switch 18e works in conjunction with that and is turned to be in an off-state and when the electric charge resetting switch 18c is in an off-state, the switch 18e works in conjunction with that and is turned to be in an on-state.

Then, as shown in FIG. 9, when resetting each of the radiation detection elements 7, if each of the TFT 8 is turned on in a condition where the electric charge resetting switch 18c is in an on-state (and the switch 18e is in an off-state), electric charges accumulated in each of the radiation detection elements 7 are released to the signal line 6 via each of the TFT 8, the electric charges flow through the signal lines 6, and passes through the electric charge resetting switch 18c of the amplifier circuit 18.

Then, the electric charges which passed through the electric charge resetting switch 18c enters the operational amplifier 18a from the output terminal side of the operational amplifier 18a and exits from the non-inverting input terminal to be grounded or flown out to the power supply section 18d so that the electric charges remaining in each of the radiation detection elements 7 are released and reset process of each of the radiation detection elements 7 are carried out.

Note that in FIG. 9, later-described FIG. 10, or the like, only on/off of the electric charge resetting switch 18c is shown and on/off of the switch 18e (refer to FIG. 8) is not shown. However, as described above, on/off of the switch 18e is turned in conjunction with on/off of the electric charge resetting switch 18c. Moreover, in the following explanation, there may be a case where only operation of the electric charge resetting switch 18c will be described, but same will be applied in such a case.

In the mean time, when readout process of the image data d is carried out, as shown in FIG. 10, in the amplifier circuit 18, the electric charge reset switch 18c is in an off-state condition (and the switch 18e is in an on-state) and the electric charges accumulated in each of the radiation detection elements 7 are released to the signal lines 6 via each of the TFT 8 set to be in an on-state, the electric charges flow through the signal lines 6, and flow into the capacitor 18b of the amplifier circuit 18 to be accumulated.

Figure 45:
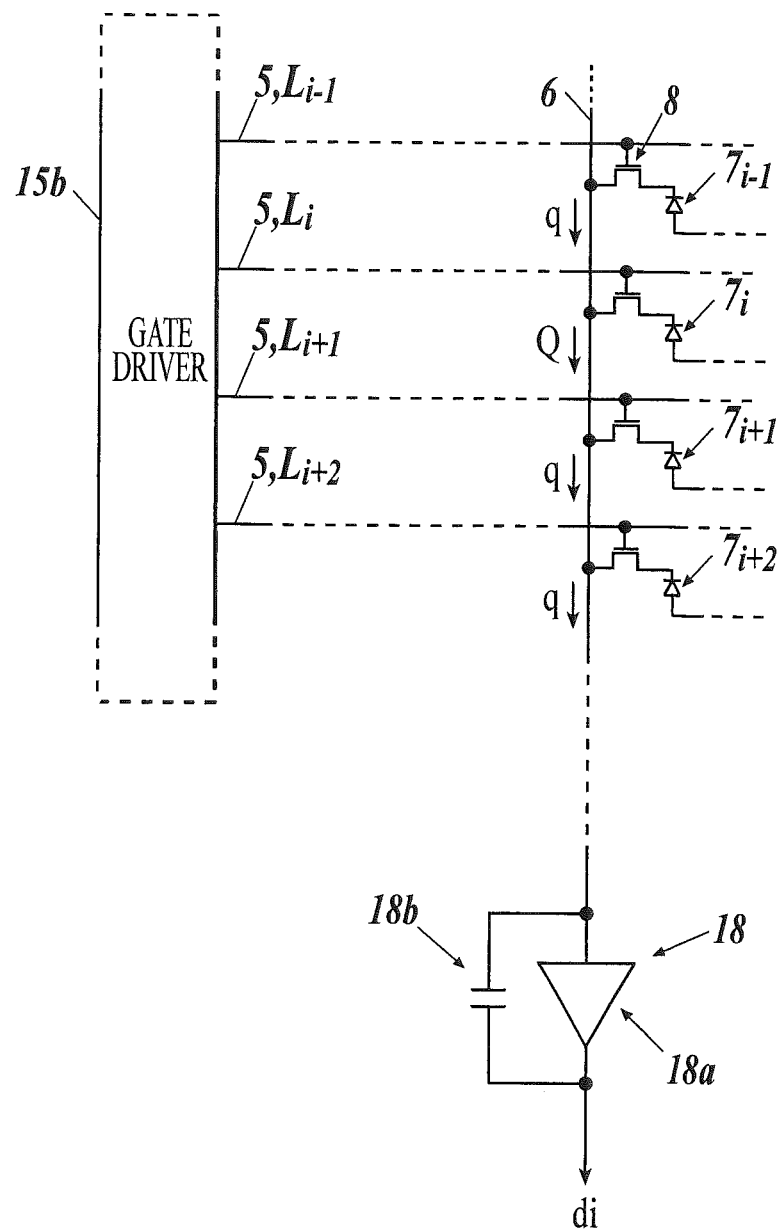
FIG. 45 is a view illustrating that sum of the electric charges read out from the radiation detection element and the electric charges leaked out from other radiation detection elements is readout as the image data.

Note that at this time, not only the electric charges from the radiation detection element 7 but also electric charges leaked out from the other radiation detection element 7, which is connected to the same signal line 6, flows into the capacitor 18b via the TFT 8, as shown in FIG. 45.

Then, in the amplifier circuit 18, a voltage value corresponding to the amount of the electric charges accumulated in the capacitor 18b is output from the output side of the operational amplifier 18a. The amplifier circuit 18 thus outputs a voltage value corresponding to the amount of electric charges output from each of the radiation detection elements 7 and carries out charge-voltage conversion.

Note that it is possible to configure the amplifier circuit 18 to output an electric current according to the electric charges output from the radiation detection element 7. Moreover, when resetting the amplifier circuit 18, the electric charge reset switch 18c is turned to be in an on-state and when the switch 18e is turned to be in an off-state in conjunction with the electric charge reset switch 18c, the input side and the output side of the amplifier circuit 18 are short-circuited and the electric charges accumulated in the capacitor 18b are discharged. Then the electric charges thus discharged enter from the output terminal side of the operational amplifier 18a and exits from the non-inverting input terminal side through the operational amplifier 18a to be grounded or to flow into the power supply section 18d so that the amplifier circuit 18 is reset.

On the output side of the amplifier circuit 18, a correlated double sampling circuit (CDS) 19 is connected. The correlated double sampling circuit 19 has a sample hold function in the present embodiment and on/off of the sample hold function of the correlated double sampling circuit 19 is controlled by a pulse signal transmitted from the control unit 22.

That is, in the case of the readout process of the image data d, for example, the electric charge reset switch 18c of the amplifier circuit 18 of each readout circuit 17 is controlled to be in an off-state first, as shown in FIG. 10. At this time, at the moment when the electric charge reset switch 18c is in an off-state condition, a so-called kTC noise is generated and electric charges attributable to the kTC noise are accumulated in the capacitor 18b of the amplifier circuit 18.

Figure 11:
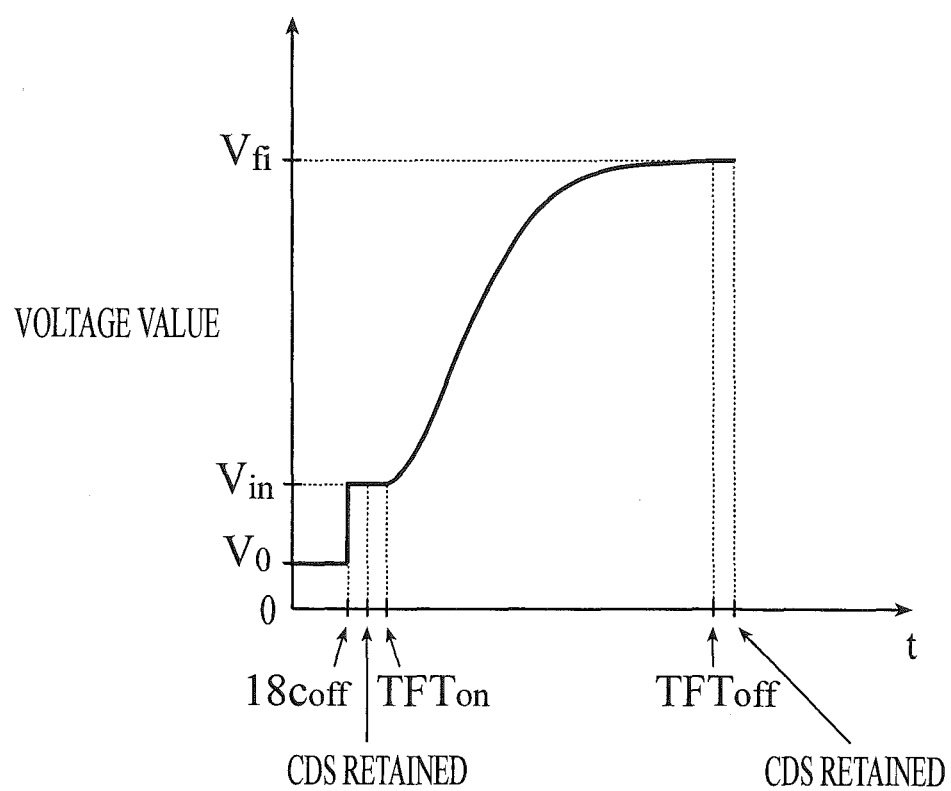
FIG. 11 is a graph showing changes or the like in voltage values of a correlated double sampling circuit.

Therefore, as shown in FIG. 11, at the moment when the voltage value output from the amplifier circuit 18 turns the electric charge reset switch 18c to an off-state (shown as "18c off" in FIG. 11), the voltage value changes from the above-mentioned reference potential $V_0$ to a voltage value $V_{in}$ for the amount of the electric charges attributable to the kTC noise. The control unit 22 transmits a first pulse signal Sp1 to the correlated double sampling circuit 19, as shown in FIG. 10, and at this point of time (shown as "CDS retained" (left side) in FIG. 11), causes the correlated double sampling circuit 19 to retain the voltage value Vin output from the amplifier circuit 18.

Subsequently, as shown in FIG. 10, an on-state voltage is applied to one scanning line 5 (for example, a line $L_n$ of the scanning line 5) from the gate driver 15b of the scanning drive unit 15 and causes the TFT 8 connected with the gate electrode 8g of this scanning line 5 to be in an on-state (refer to FIG. 10. In FIG. 11, shown as "TFT on"). Then, electric charges accumulated in each of the radiation detection elements 7, to which these TFTs 8 are respectively connected, flow into the capacitor 18b of the amplifier circuit 18 via each signal line 6 and, as shown in FIG. 11, the voltage value output from the amplifier circuit 18 increases according to the amount of the electric charges accumulated in the capacitor 18b.

Then, the control unit 22 switches the on-state voltage applied to the scanning line 5 from the gate driver 15b to an off-state voltage when a predetermined period of time elapses, as shown in FIG. 10, to turn the TFT 8 whose gate electrode 8g is connected to the scanning line 5 to an off-state (shown as "TFT off" in FIG. 11), and transmits a second pulse signal Sp2 to the correlated double sampling circuit 19 at this stage to cause the correlated double sampling circuit 19 to retain a voltage value Vfi output from the amplifier circuit 18 at this moment (shown as "CDS retained" (right side) in FIG. 11").

When the voltage value Vfi is retained by the second pulse signal Sp2, each of the correlated double sampling circuits 19 calculates a difference of voltage values Vfi−Vin and outputs the difference Vfi−Vin thus calculated to a downstream side as the analog value image data d.

The image data d of each radiation detection element 7 output from the correlated double sampling circuit 19 is transmitted to an analog multiplexer 21 and is sequentially transmitted from the analog multiplexer 21 to an A/D converter 20. Then, the image data d is sequentially converted into the image data d having a digital value by the A/D converter 20, output to a storage unit 40, and sequentially stored.

The control unit 22 includes a computer which is not shown, where a central processing unit (CPU), a read only memory (ROM), a random access memory (RAM), an input/output interface, and the like are connected to a bus, or a field programmable gate array (FPGA). The control unit 22 may include a dedicated control circuit. Then, the control unit 22 controls operations or the like of each member of the radiation image capturing apparatus 1. Moreover, as shown in FIG. 7 or the like, storage unit 40 including a dynamic RAM (DRAM) is connected to the control unit 22.

In addition, in the present embodiment, the above-mentioned antenna device 39 is connected to the control unit 22 and also a battery 41 for supplying power to each member such as the detecting part P, the scanning drive unit 15, the readout circuit 17, the storage unit 40, the bias power source 14, and the like. Furthermore, to the battery 41, a connection terminal 42 for recharging the battery 41 from a recharging device which is not shown by supplying power to the battery 41 is provided.

As mentioned above, the control unit 22 controls operations of each function part of the radiation image capturing apparatus 1 such as controlling the bias power source 14 by setting or changing the bias voltage to be applied to each of the radiation detection elements 7 from the bias power source 14.

Moreover, in the present invention, the control unit 22 carries out acquisition process of a dark image data Od prior to photographing of a radiation image which is carried out by irradiating radiation to the radiation image capturing apparatus 1, carries out readout process of the image data D as main image after the radiation image capturing operation, and subsequently thereto, carries out acquisition process of offset data O. Explanation of these processes will be given after configuration of a radiation image capturing system 50 is explained.

[Radiation Image Capturing System]

Figure 12:
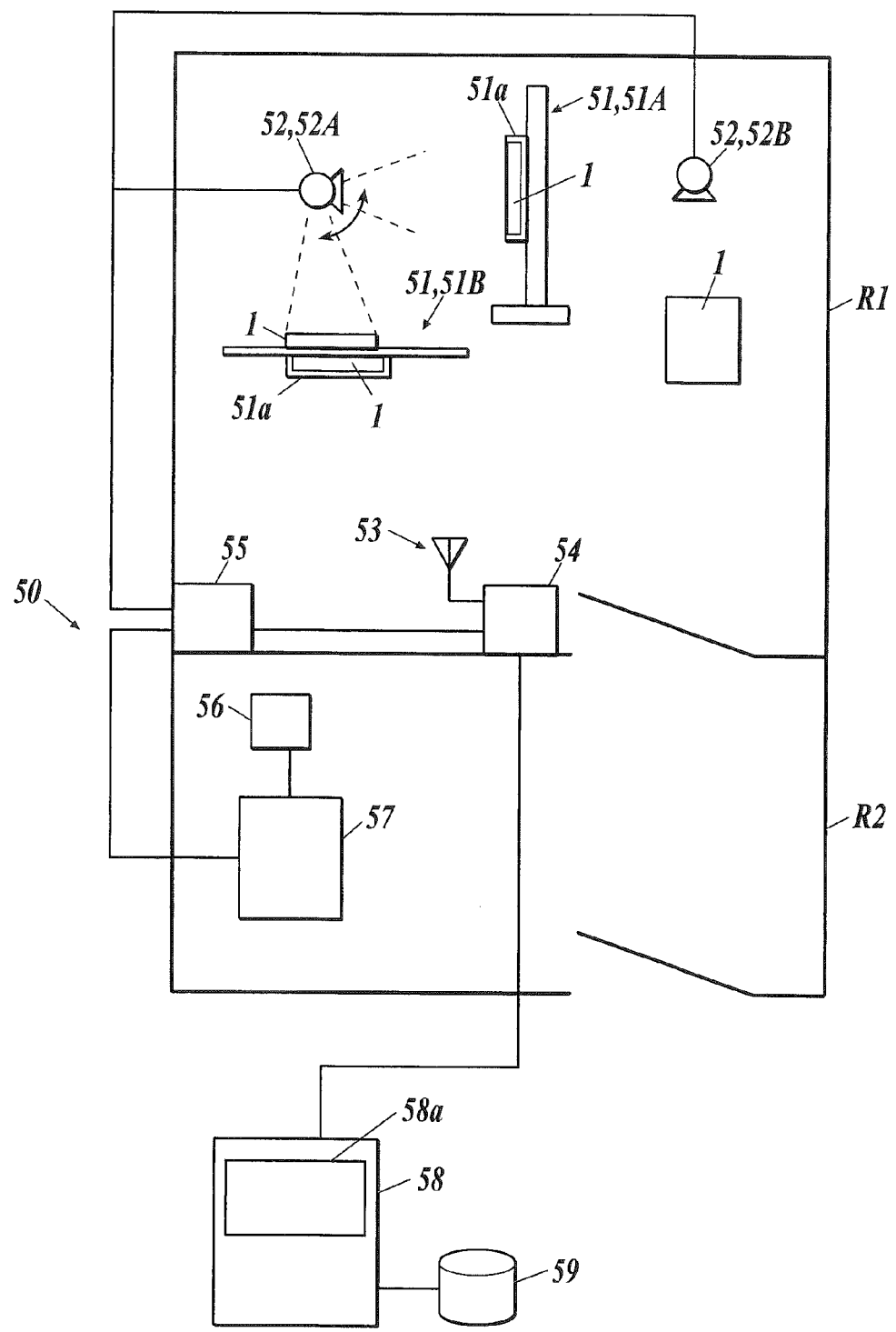
FIG. 12 is a view showing an overall configuration of a radiation image capturing system according to each embodiment of the present invention.

FIG. 12 is a view showing an overall configuration of a radiation image capturing system according to the present embodiment. The radiation image capturing system 50 is provided to a photographing chamber R1 for carrying out photographing of, for example, a subject, which is a part of a body of an unillustrated patient (a part of a patient which is to be photographed), by irradiating with radiation, an anterior chamber R2 where various operations such as control of initiation of irradiation with radiation which is to be irradiated onto the subject are carried out by an operator such as a radiology technician, and outside thereof or the like.

In the photographing chamber R1, a bookie device which can mount the above-described radiation image capturing apparatus 1, a radiation source 52 including an unillustrated X-ray tube for generating radiation to be irradiated onto the subject, a radiation generating device 55 for controlling the radiation source 52, a relaying device 54 having a wireless antenna 53 for relaying communication when the radiation generating device 55 and a console 58 communicates or when the radiation image capturing apparatus 1 and the console 58 communicates, and the like are provided.

Note that in FIG. 12, a case where the portable type radiation image capturing apparatus 1 is mounted on a cassette retention part 51a of the bookie device 51 is shown. However, as mentioned above, the radiation image capturing apparatus 1 may be integrally formed with the bookie device 51 or a supporting board. Moreover, as described above, the radiation image capturing apparatus 1 transmits and receives necessary information by a wireless method between the console 58 via the antenna device 39 (refer to FIG. 1 or FIG. 7) or the relaying device 54. However, for example, a cable may be provided between the relaying device 54 and each of the Bucky devices 51 and the cable is connected to the radiation image capturing apparatus 1 to transmit and receive by cable.

The relaying device 54 is connected to the radiation generating device 55 or the console 58 and an unillustrated converter for carrying out conversion of a signal for LAN communication or the like for transmitting information between the relaying device 54 and the console 58 or the like into a signal for transmitting information between the relaying device 54 and the radiation generating device 55 and for carrying out the opposite conversion is incorporated in the relaying device 54.

In the anterior chamber R2, according to the present embodiment, there is provided an operation table 57 for the radiation generating device 55 and an exposure switch 56 is provided on the operation table 57 for instructing the initiation of irradiation with radiation to the radiation generating device 55 through manipulation by an operator such as a radiology technician.

The radiation generating device 55 carries out various controls to the radiation source 52 such as moving the radiation source 52 to a predetermined position so that radiation can be appropriately irradiated onto the mounted radiation image capturing apparatus 1, adjusting direction of the irradiation, adjusting unillustrated focus diaphragm so that irradiation can be performed within a predetermined area of the radiation image capturing apparatus 1, or adjusting the radiation source 52 so that an appropriate dose of radiation can be emitted.

Configuration of the radiation image capturing apparatus 1 or the like has been described above, and, although the radiation image capturing apparatus 1 is used by being mounted on the bookie device 51 in the present embodiment, the radiation image capturing apparatus 1 can be used independently, without being mounted on the bookie device 51.

That is, the radiation image capturing apparatus 1 may be used by setting the device on a bed provided in the photographing chamber R1 or, as shown in FIG. 12, setting the device on an upper surface side of a bookie device 51B for photographing a recumbent position so that a hand or the like of a patient, which is a subject, can be set on the radiation incidence surface R (refer to FIG. 1), or for example, setting the device between a recumbent patient's lower back or a leg and a bed. In this case, radiation is emitted from, for example, the portable radiation source 52B onto the radiation image capturing apparatus 1 through the subject to carry out photographing of a radiation image.

In the present embodiment, image process is carried out to image data based on the image data or the like transmitted from the radiation image capturing apparatus 1 and the console 58 including a computer or the like which can generate final radiation image is provided outside of the photographing chamber R1 or the anterior chamber R2. Note that it is also possible to provide the console 58 to the anterior chamber R2 or the like.

In the present embodiment, the console 58 includes a display unit 58a having a cathode ray tube (CRT) or a liquid crystal display (LCD) and a storage unit 59 having a hard disk drive (HDD) or the like is connected to or incorporated in the console 58.

Note that it is also possible to cause the console 58 to display a preview image based on the image data acquired by photographing a radiation image, to have a function to transit the radiation image capturing apparatus 1 between awake up condition and a sleep condition, or to enable an operator such as the radiology technician to create or select an imaging order information indicating the content of radiation imaging carried out in the photographing chamber R1. Thus, the console 58 may be appropriately configured.

[On Detection of Initiation of Irradiation with Radiation by Radiation Image Capturing Apparatus 1 Itself]

Here, as described above, several methods for detecting initiation of irradiation with radiation by the radiation image capturing apparatus 1 itself for a case where an interface is not, or cannot be, constructed between the radiation image capturing apparatus 1 and the radiation generating device 55.

[Method 1]

For example, as shown in the above-mentioned FIG. 4, it is configured that readout process of the image data d is carried out while on-state voltage is sequentially applied to each of the lines $L_1$ to $L_x$ of the scanning line 5 from the gate driver 15b for each frame prior to the photographing of a radiation image.

Then, it is possible to configure that if the image data d which was read out by applying the on-state voltage to a line $L_n$ of the scanning line 5 significantly increases compared to the image data d read out before the application of the voltage and exceeds a predetermined threshold value, it is judged that irradiation with radiation to the radiation image capturing apparatus 1 started and initiation of irradiation with radiation is detected.

Figure 13:
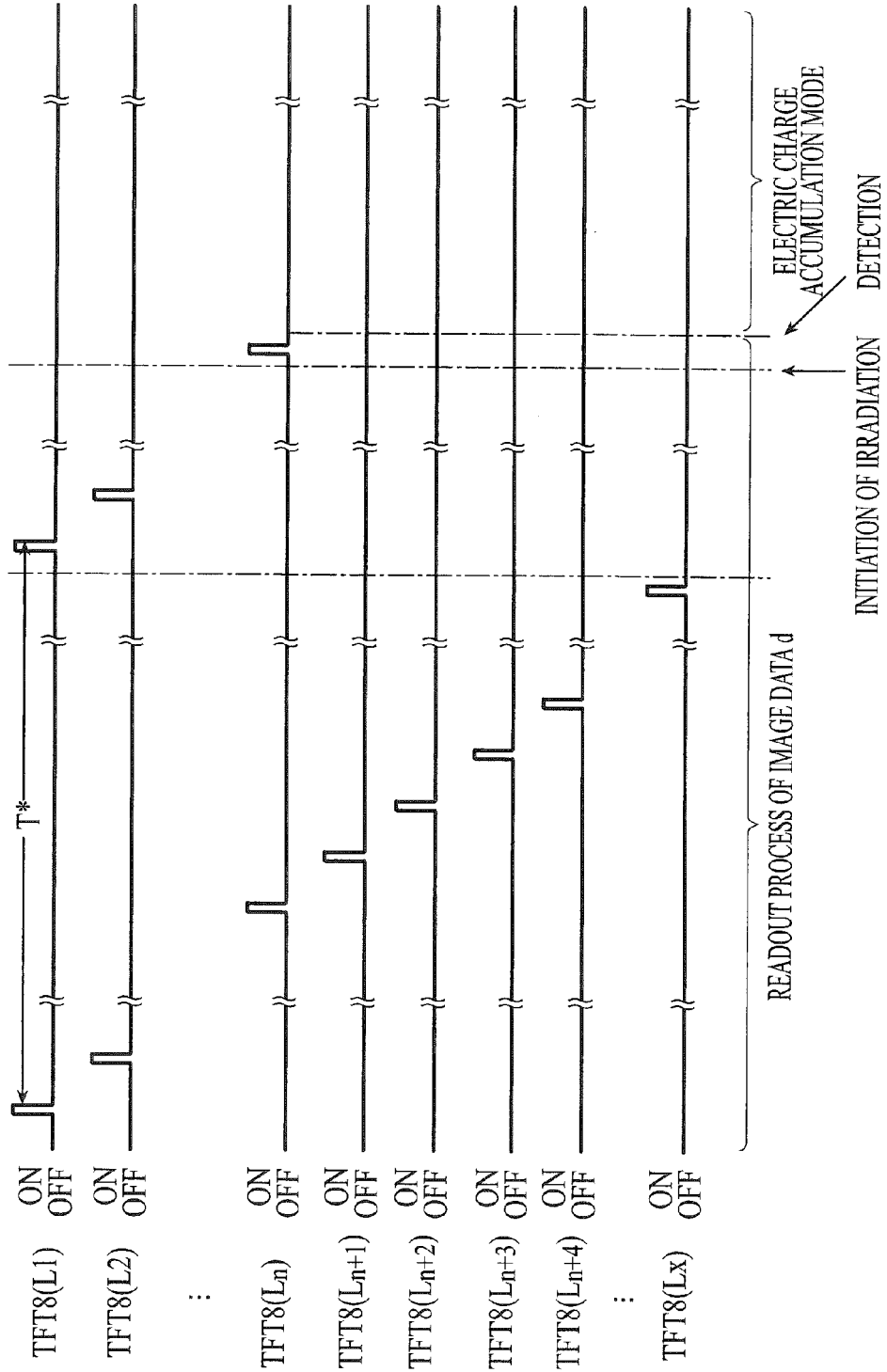
FIG. 13 is a timing chart showing timing for applying an on-state voltage to each scanning line in the readout process of image data before photographing of a radiation image and illustrating that application of the on-state voltage is stopped at the point of time when initiation of irradiation with radiation is detected.

In this case, if detection of initiation of irradiation with radiation is carried out on the basis of the image data d read out by applying the on-state voltage to the line $L_n$ of the scanning line 5, as shown in FIG. 13, readout process of the image data d, that is, application of the on-state voltage to the lines $L_{n+1}$ and beyond of each scanning line 5, is stopped and an on-state voltage is applied to all the lines $L_1$ to $L_x$ of the scanning line 5 from the gate driver 15b of the scanning drive unit 15 so that the mode is shifted to an electric charge accumulation mode for accumulating electric charges in each of the radiation detection elements 7.

Note that stop of applying the on-state voltage to each scanning line 5, switching to the off-state voltage, and shift to the electric charge accumulation mode at the point of time when initiation of irradiation with radiation is detected will be similarly applied to the cases of the following methods or the like and explanation thereof will be omitted. Moreover, an effective accumulation time T* is shown in FIG. 13 and explanation thereof will be given later.

[Method 2]

In addition, instead of carrying out the readout process of the image data d prior to photographing of a radiation image and detecting the initiation of irradiation with radiation based on the value of the read out image data d, it is possible to configure that the electric charges leaked out to the signal lines 6 from each of the radiation detection elements 7 via the TFT 8 are read out as leaked data $d_{leak}$ by the readout circuit 17 and detect the initiation of irradiation with radiation based on the leaked data $d_{leak}$ thus read out.

Specifically, prior to photographing of a radiation image, each readout circuit 17 is operated in a condition where the off-state voltage is applied to all the lines $L_1$ to $L_x$ of the scanning line 5, as shown in FIG. 14. That is, similarly to the case of reading out the image data d, the electric charge reset switch 18c of the amplifier circuit 18 of the readout circuit 17 (refer to FIG. 8) is set to be in an off-state and the capacitor 18b is set to be in a condition where the electric charges can be accumulated. Then, pulse signals Sp1 and Sp2 are transmitted from the control unit 22 to the correlated double sampling circuit 19. However, on/off operation of each TFT 8 is not carried out during this period.

Figure 15:
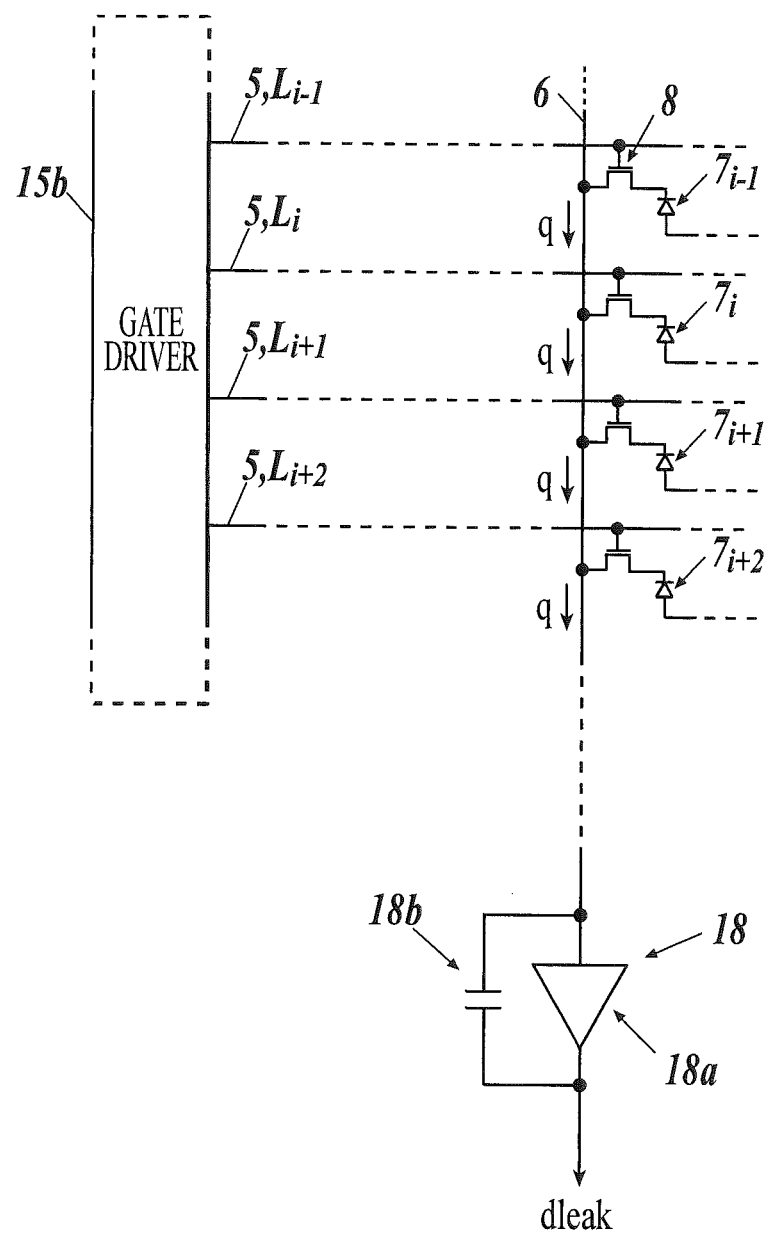
FIG. 15 is a view illustrating that each electric charge leaked out from each of the radiation detection elements via TFT is read out as leaked data.

If each of the readout circuits 17 is thus operated, each of electric charges q leaked out from each of the radiation detection elements 7 is accumulated in the capacitor 18b of the amplifier circuit 18 via each of the TFT 8 set to be in the off-state. Therefore, the electric charges thus accumulated, that is, a voltage value equivalent to the sum of the electric charges q leaked out from each of the radiation detection elements 7, are output from the amplifier circuit 18 and sampled by the correlated double sampling circuit 19 which is not shown in FIG. 15, and the leaked data $d_{leak}$ is read out.

According to such a configuration, similarly to the case where an explanation was given by using the above-mentioned FIG. 45, the electric charge q leaked out from each of the radiation detection elements $7_i$ via each of the TFT 8 is very small before irradiation with radiation to the radiation image capturing apparatus 1, sum of such electric charges is also a small value and therefore, the leaked data $d_{leak}$ has a small value. However, when irradiation with radiation to the radiation image capturing apparatus 1 is started, the electric charge q leaked out from each of the radiation detection elements $7_i$ via each of the TFT 8 becomes high and sum of such electric charges becomes high. Therefore, the value of the leaked data $d_{leak}$ thus read out increases.

Therefore, it is possible to configure that the leaked data $d_{leak}$ is periodically read out and initiation of irradiation with radiation is detected when the leaked data $d_{leak}$ significantly increases compared to the previously read out leaked data $d_{leak}$ and, for example, exceeds a predetermined threshold value, and it is judged that irradiation with radiation to the radiation image capturing apparatus 1 is started at that point of time.

Note that in this case, readout process of the leaked data $d_{leak}$ is carried out while the off-state voltage is applied to each of the lines $L_1$ to $L_x$ of the scanning line 5 and each of the TFT 8 is in an off-state. Then, if the off-state voltage remains to be applied to each of the lines $L_1$ to $L_x$ of the scanning line 5, dark electric charges are accumulated in each of the radiation detection elements 7.

Figure 16:
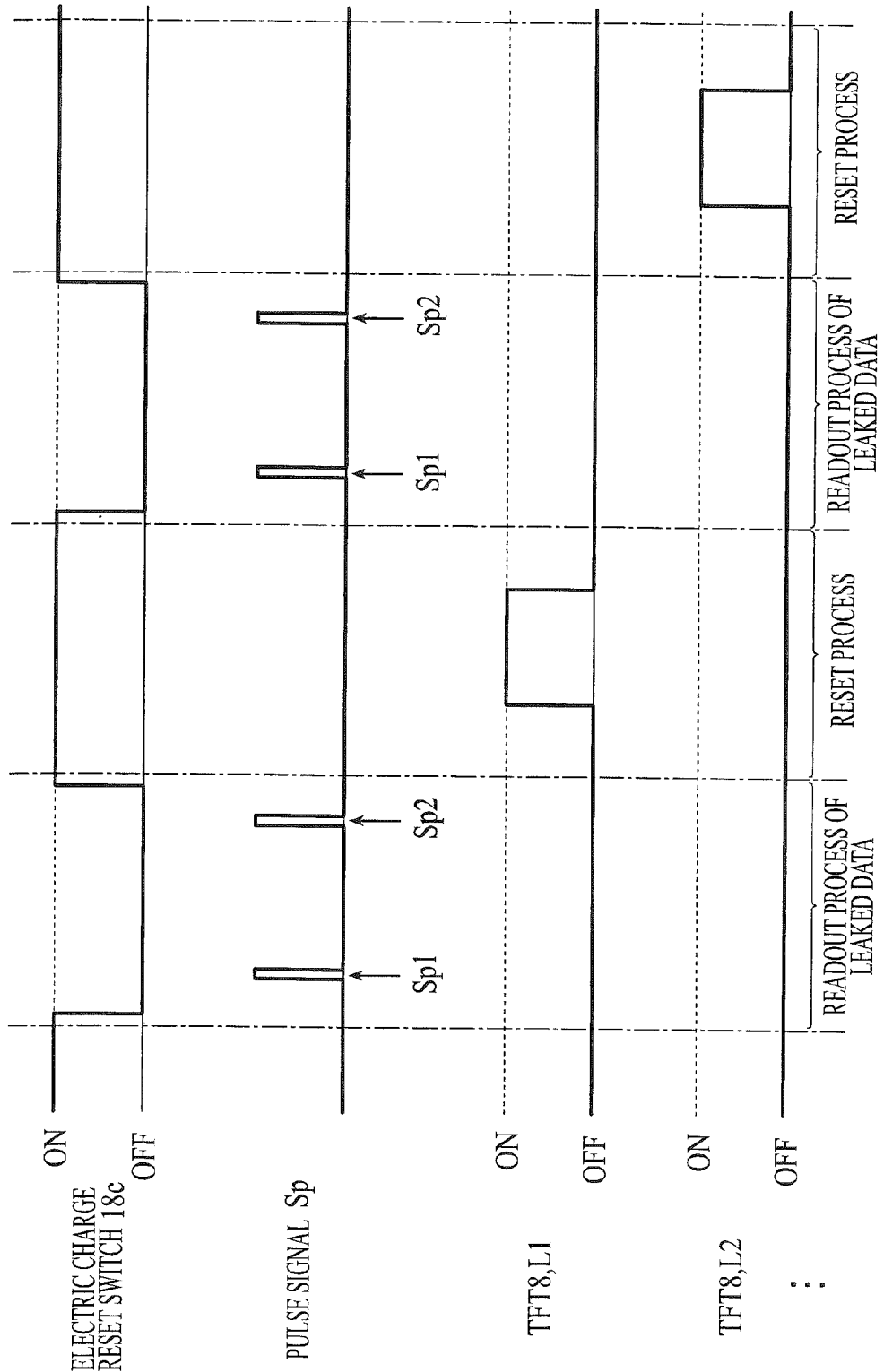
FIG. 16 is a timing chart for a case where readout process of the leaked data and reset process of each of radiation detection elements are alternately carried out.

Therefore, as shown in FIG. 16, for example, it is possible to alternately carry out the readout process of the leaked data $d_{leak}$ and reset process of each of the radiation detection elements 7 which is carried out by sequentially applying an on-state voltage to each of the lines $L_1$ to $L_x$ of the scanning line 5.

Moreover, instead of alternately carrying out the readout process of the leaked data $d_{leak}$ and reset process of each of the radiation detection elements 7, it is also possible to configure that the readout process of the leaked data $d_{leak}$ and readout process of the image data d from each of the radiation detection elements 7 are alternately carried out. Note that in case of adopting such a configuration, it is also possible to configure that the read out image data d is not used for detection of initiation of irradiation with radiation to the radiation image capturing apparatus 1 and it is also possible to use both the read out leaked data $d_{leak}$ and the image data d to carry out initiation of irradiation with radiation to the radiation image capturing apparatus 1.

[Method 3]

In addition, as described above, it has been known that when irradiation is performed to the radiation image capturing apparatus 1, part of the electric charges generated by the irradiation with radiation in each of the radiation detection elements 7 flows out to the bias line 9 or an electric current flows through the wire of the radiation image capturing apparatus 1 by changes in difference of potential between the first electrode 74 and the second electrode 78 of each of the radiation detection elements 7 (refer to FIG. 7) due to an electron-hole pair generated in each of the radiation detection elements 7.

Figure 17:
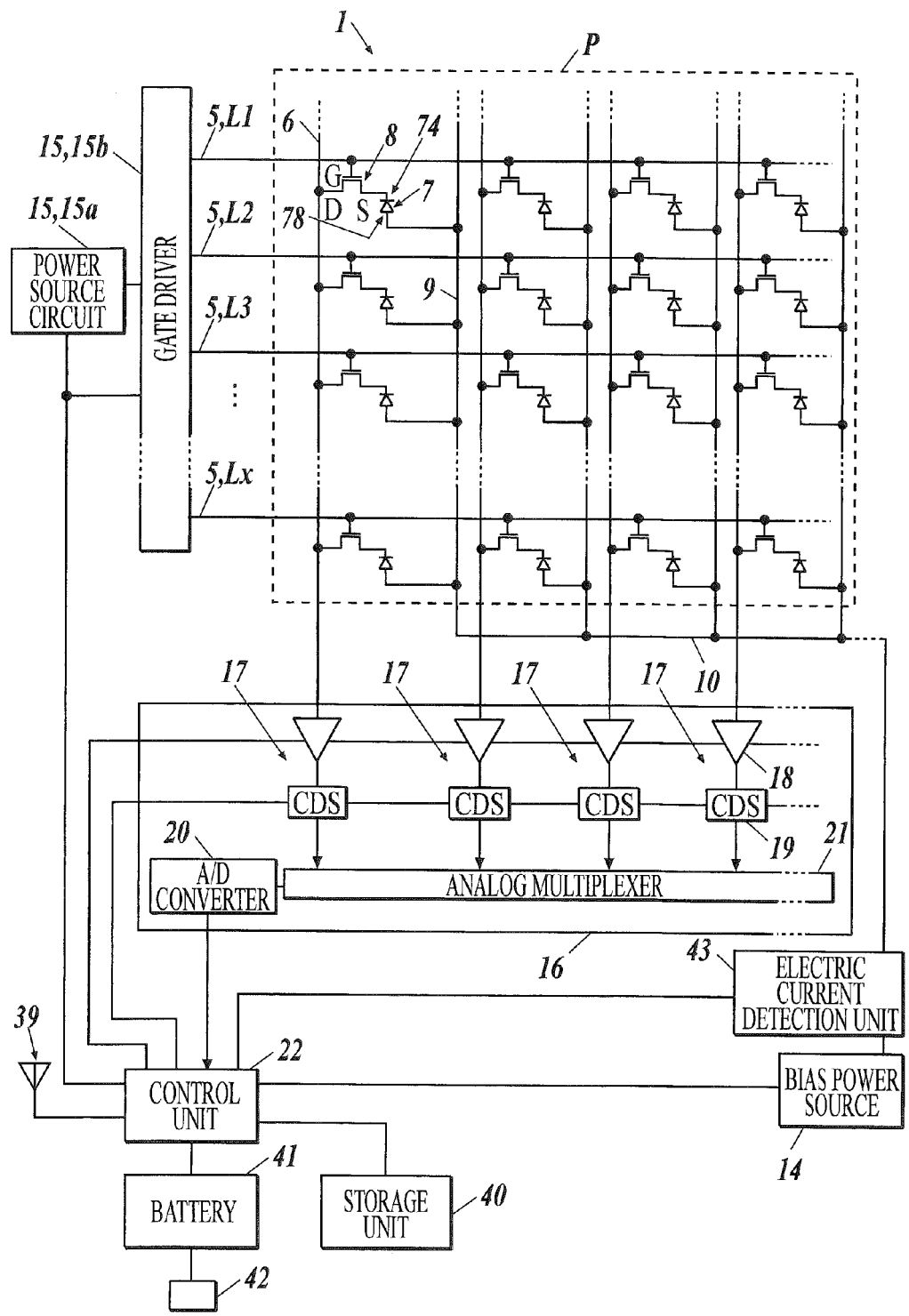
FIG. 17 is a block diagram showing an example of an equivalent circuit of a radiation image capturing apparatus to which an electric current detecting means is provided.

Therefore, as shown in FIG. 17, for example, it is possible to configure that an electric current detection unit 43 is provided to the bias lines 9 for connecting each of the radiation detection elements 7 and bias power source 14 or to the wire connection 10 for binding the bias lines 9, to the wire 15c (refer to FIG. 7) connecting each of the scanning lines 5 or the power source circuit 15a of the scanning drive unit 15 with the gate driver 15b, or the like so that a value of the current which flows through the wire connection 10, the scanning line 5, or the wire 15c can be monitored.

In this case, only dark electric charges are generated in each of the radiation detection elements 7 and electric charges attributable to irradiation with radiation are not generated until the radiation image capturing apparatus 1 is irradiated with radiation. Therefore, the value of the electric current is small. However, when the radiation image capturing apparatus 1 is irradiated with the radiation, the value of the electric current which flows through the radiation image capturing apparatus 1 increases, as described above. Therefore, it is possible to configure that the initiation of irradiation with radiation is detected at the point of time when the value of the electric current detected by the electric current detecting means 43 or the like exceeds, for example, a predetermined threshold value.

Note that the method for detecting the initiation of irradiation with radiation by the radiation image capturing apparatus 1 itself is not limited to the above-described methods 1 to 3. For example, it is also possible to configure the radiation image capturing apparatus 1 to detect the initiation of irradiation with radiation by providing a radiation sensor to the radiation image capturing apparatus 1 and it is possible to adopt any appropriate method.

Moreover, a case shown in FIG. 13 where the readout process of the image data d is carried out for each frame prior to the photographing of a radiation image, that is, a case where the method 1 is adopted, will be explained below. However, similar explanation will be given in a case where another method is adopted.

[On Readout Process of Main Image Data D and Acquisition Process of Offset Data O]

Next, readout process of the image data D as the main image after the photographing of the radiation image and acquisition process of the offset data following the readout process will be explained. Note that in the following explanation, the image data D as the main image to be read out after the photographing of the radiation image will be referred to as the main image data D.

In the present embodiment, as shown in FIG. 13, at the point of time when irradiation with radiation is detected based on the image data d read out by applying the on-state voltage to the line $L_n$ of the scanning line 5, the readout process of the image data d is stopped and the off-state voltage is applied to all the lines $L_1$ to $L_x$ of the scanning line 5 to shift to the electric charge accumulation mode.

Then, as shown in FIG. 18, after a predetermined period of time t elapsed since the shift to the electric charge accumulation mode, the readout process of the main image data D will be carried out. Note that during this predetermined period of time τ, irradiation with radiation to the radiation image capturing apparatus 1 is finished.

At this time, in the present embodiment, the readout process of the main image data D is carried out at the point of time when the initiation of irradiation with radiation is detected in the readout process of the image data d prior to the photographing of the radiation image or by applying the on-state voltage to a scanning line 5 (for the case of FIG. 18, line $L_{n+1}$ of the scanning line 5) to which the on-state voltage is to be applied subsequently to the scanning line 5 (for the case of FIG. 18, line $L_n$ of the scanning line 5) to which the on-state voltage has been applied just previously and sequentially applying the on-state voltage to each of the scanning lines 5 to carry out the readout process of the main image data D.

Moreover, in the present embodiment, in the readout process of the main image data D, as shown in FIG. 13 and FIG. 18, the on-state voltage is sequentially applied to each of the lines $L_{n+1}$ to $L_x$ and $L_1$ to $L_n$ of the scanning line 5 from the gate driver 15b of the scanning drive unit 15 at the same timing at the readout process of the image data d prior to photographing of the radiation image, that is, at the same timing as the timing between application of the on-state voltage to one scanning line 5 and timing when the on-state voltage is applied to a next scanning line 5.

In the present embodiment, the on-state voltage is thus applied sequentially to the line $L_n$ of the scanning line 5 to finish the readout process of the main image data D. Then, subsequently, reset process of each of the radiation detection elements 7 for one frame is carried out. Note that it may be configured that the reset process of each of the radiation detection elements 7 is carried out for a predetermined number of frames.

Then, after the reset process of each of the radiation detection elements 7 is carried out, the off-state voltage is applied to each scanning line 5 for a predetermined period of time T and then the on-state voltage is sequentially applied to each of the lines $L_{n+1}$ to $L_x$ and $L_1$ to $L_n$ of the scanning line 5 at the same timing as in the case of the main image data D to read out and acquire the offset data O from each of the radiation detection elements 7 (acquisition process of the offset data O).

Note that as described above, in the electric charge accumulation mode prior to the readout process of the main image data D (refer to FIG. 18), radiation is emitted to the radiation image capturing apparatus 1 from the radiation source 52 (refer to FIG. 12). However, in the electric charge accumulation mode prior to the acquisition process of the offset data O (refer to FIG. 19), the radiation image capturing apparatus 1 is not irradiated with radiation. Moreover, the effective accumulation time T is shown in FIG. 18 and FIG. 19, and explanation thereof will be given later.

[On Acquisition Process of Dark Image Data Od Before Photographing of Radiation Image]

Figure 41:
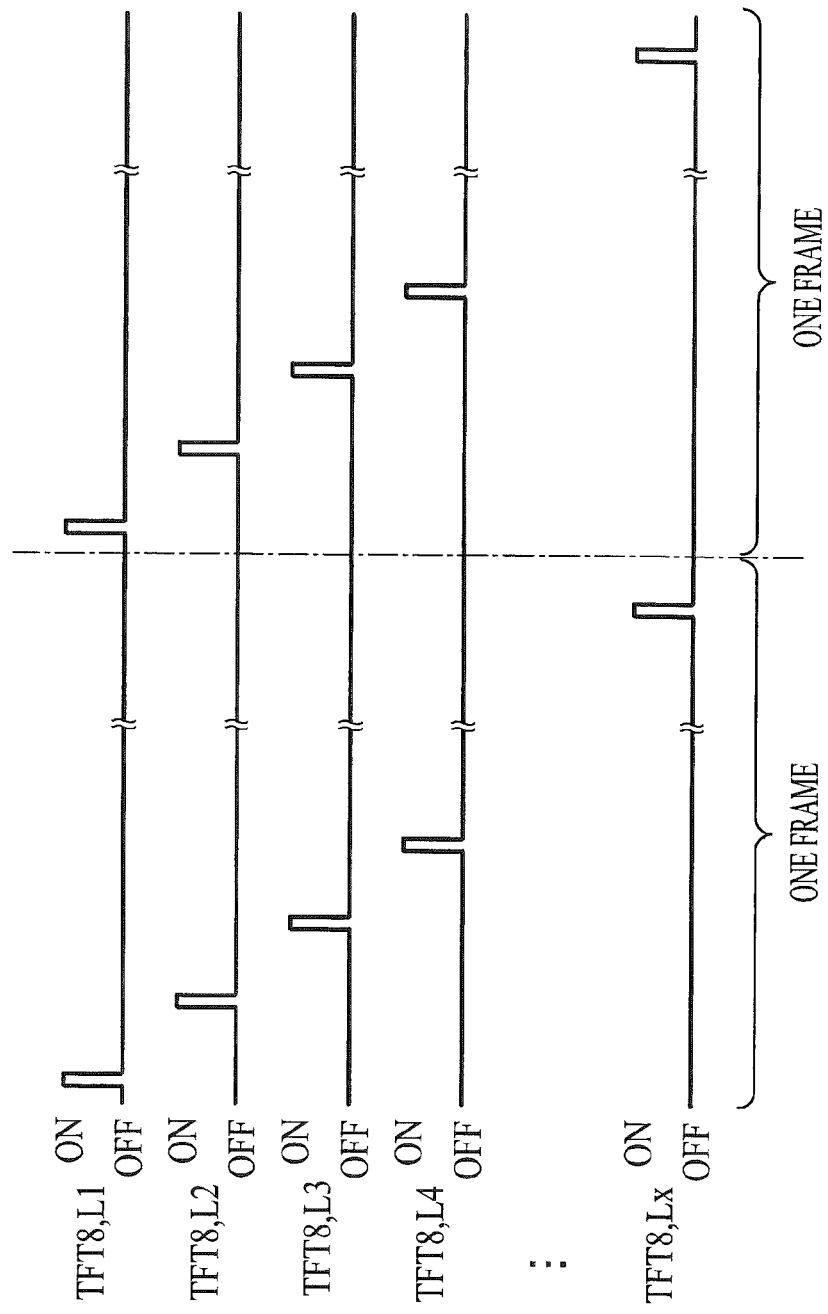
FIG. 41 is a timing chart illustrating that the readout process of the image data is repeatedly carried out for each frame.
Figure 42:
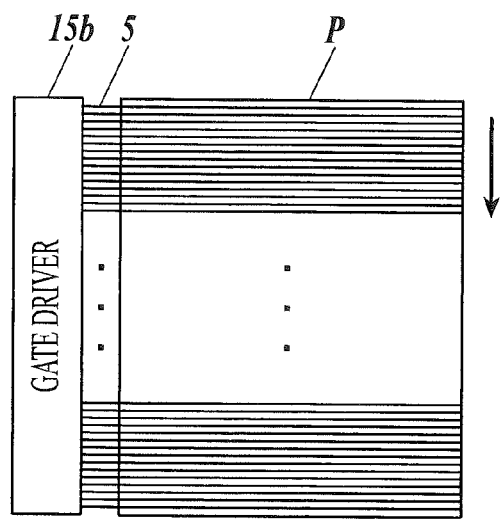
FIG. 42 is a view illustrating the readout process of the image data from each radiation detection element for each frame.
Figure 43:
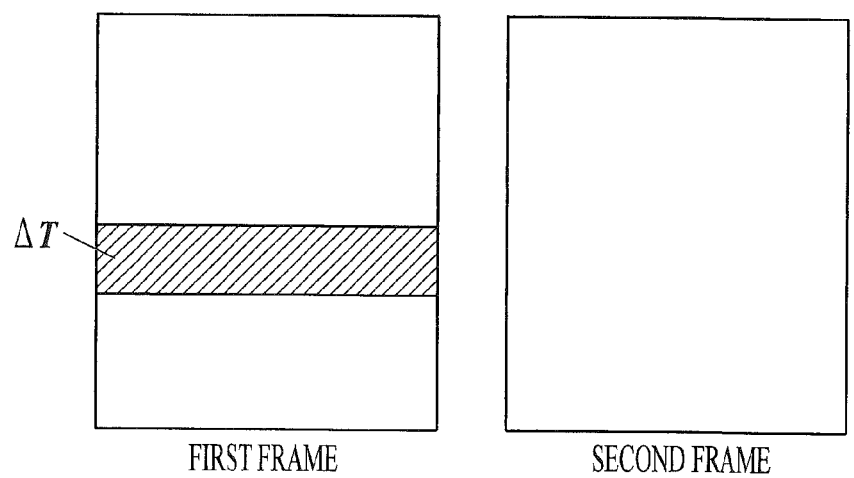
FIG. 43 is a view showing that irradiation was performed while the on-state voltage was sequentially applied to the scanning lines in the ΔT part and irradiation was finished.
Figure 44A:
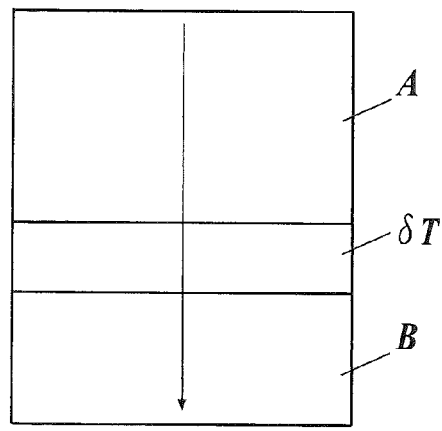
FIG. 44A is a view showing a radiation image generate on the basis of the reconstructed image data.
Figure 44B:
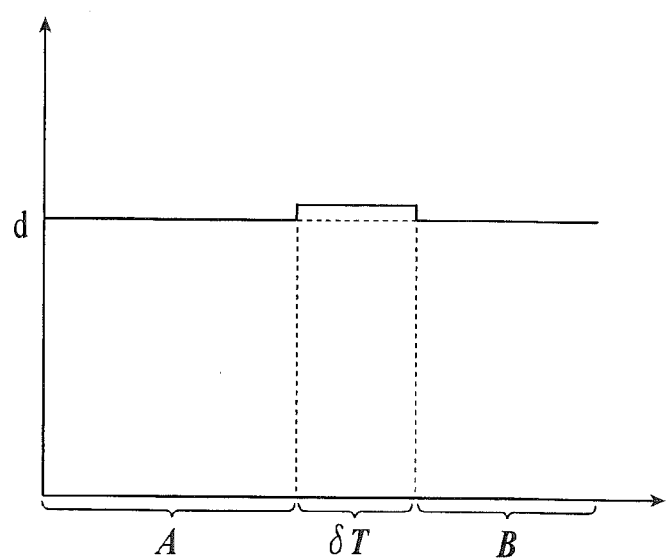
FIG. 44B is a graph showing that the image data in the image area δT becomes greater than the image data in image areas A and B.

In the meantime, in the present embodiment, readout process of the image data d from the radiation detection element 7 is carried out by sequentially applying the on-state voltage to each of the lines $L_1$ to $L_x$ of the scanning line 5 before photographing of a radiation image, that is, before irradiation with radiation to the radiation image capturing apparatus 1, as shown in FIG. 13 or FIG. 41.

Because the image data d in this case is the data read out before irradiation is performed to the radiation image capturing apparatus 1, the image data d does not include the above-mentioned true image data D*, that is, image data attributable to the electric charges generated in each of the radiation detection elements 7 by irradiation with radiation to the radiation image capturing apparatus 1, as a matter of course.

Moreover, since the radiation image capturing apparatus 1 has not been irradiated with radiation yet, the image data d does not include the above-mentioned offset portion Olag attributable to the lag caused by the electric charges generated in each of the radiation detection elements 7 by irradiation with radiation, as a matter of course, and includes only the data attributable to the dark electric charges generated in each of the radiation detection elements 7.

That is, the image data d read out before photographing of the radiation image is data attributable only to the dark electric charges generated in each of the radiation detection elements 7 during a period from the moment when the on-state voltage applied to the scanning line 5 in one frame is switched to the off-state voltage and the TFT 8 is set to be in an off-state until the on-state voltage applied to the scanning line 5 in the subsequent frame is switched to the off-state voltage (hereinafter, this period of time will be referred to as the effective accumulation time. For example, refer to the effective accumulation time T* in FIG. 13).

Therefore, it is possible to use the image data d as the above-mentioned offset data Odark, that is, the offset data Odark attributable to the dark electric charges included in the read out main image data D. Note that the image data d is read out prior to photographing of a radiation image and is not the offset data Odark itself included in the main image data D read out after photographing of the radiation image and in that sense, in the present invention, the image data d acquired before photographing of the radiation image will be referred to as a dark image data Od.

However, if the above-mentioned effective accumulation time differs, the dark image data Od has a different value. However, according to a study by the inventors of the present invention, it is understood that the value of the dark image data Od does not necessarily change proportionally to the effective accumulation time when the effective accumulation time is short.

Moreover, in the acquisition process of the dark image data Od before photographing of the radiation image (readout process of the image data d), the effective accumulation time T* (refer to FIG. 13) is shorter for the amount of time τ (that is, the above-mentioned predetermined period of time τ) required for the electric charge accumulation mode than the effective accumulation time T in the case of the readout process of the main image data D (refer to FIG. 18) or following acquisition process of the offset data O (refer to FIG. 19).

Therefore, the dark image data Od acquired before photographing of the radiation image cannot be used as the offset data Odark in this condition.

Therefore, as a method for solving this problem, for example, conversion factor for converting the dark image data Od acquired in the case of the effective accumulation time T* into the offset data Odark read out in the effective accumulation time T is experimentally acquired beforehand. Then, it is possible to configure that at the time of actual photographing of a radiation image, the image data d, that is, the dark image data Od, is read out and saved for each frame before photographing of the radiation image, and by multiplying the conversion factor to the data, the offset data Odark included in the main image data D is calculated and estimated.

Moreover, as another method, it is possible to configure that at the time of the readout process of the image data d before photographing of a radiation image, as shown in FIG. 20, between a frame to which acquisition process of the dark image data Od is carried out and a frame just prior to that, a period of time for applying the off-state voltage to each of the scanning line 5 from the gate driver 15b of the scanning drive unit 15 for the same amount of time as time T necessary for the electric charge accumulation mode.

According to such a configuration, it becomes possible to set the effective accumulation time T* in the acquisition process of the dark image data Od before photographing of the radiation image to be the same time as the effective accumulation time T for the case of readout process of the main image data D (refer to FIG. 18) or the case of acquisition process of the offset data O (refer to FIG. 19) following that process. Thus, it becomes possible to use the dark image data Od acquired before photographing of the radiation image as the same value as the offset data Odark included in the main image data D.

However, during the time T in which the off-state voltage is applied to each scanning line 5 as described above, readout process of the image data d (or acquisition process of the dark image data Od) is not carried out. Therefore if irradiation with radiation to the radiation image capturing apparatus 1 is started during that period, detection process of initiation of irradiation with radiation based on the image data d (or the dark image data Od) cannot be carried out. Therefore, detection of initiation of irradiation with radiation is delayed.

Therefore, it is preferable that the device is configured to carry out the process for acquiring the dark image data Od by setting time between frames for the predetermined period of time τ, as described above, at a predetermined ratio such as once every 10 times of readout processes of the image data d for each frame.

Moreover, when reset process of each of the radiation detection elements 7 is carried out before photographing of a radiation image such as a case where readout process of the leaked data $d_{leak}$ and reset process of each of the radiation detection elements 7 are alternately carried out before photographing of a radiation image or a case where the reset process of each of the radiation detection elements 7 is repeatedly carried out before photographing of a radiation image when the electric current detection unit 43 is provided by the above-mentioned method 3, the electric charges released from each of the radiation detection elements 7 are not read out as the image data, but as described above, are grounded from the non-inverting input terminal through the operational amplifier 18a of the amplifier circuit 18 or flow out to the power supply section 18d. Therefore, it becomes impossible to acquire the dark image data Od in this condition.

Therefore, similarly to the above, for example, it is possible to configure that at an appropriate timing before photographing of a radiation image such as once every 10 times of reset process of each of the radiation detection elements 7 for each frame, after the reset process of each of the radiation detection elements 7 is finished, the off-state voltage is applied to each scanning line 5 for the above-mentioned predetermined period of time τ and then the image data d, that is, the dark image data Od is read out. In this case, readout process is not carried out in other frames and reset process of each of the radiation detection elements 7 is carried out.

[On Correction Process of Main Image Data D]

Next, the console 58 carries out an image process to the true image data D* calculated on the basis of the main image data D or the like acquired as above and a final radiation image is generated. However, as mentioned above, the acquired offset data O includes the Olag, the portion offset by lag, other than the offset data Odark attributable to the dark electric charges. Therefore, if the Olag, the portion offset by lag, cannot be appropriately processed, even if the offset data O is subtracted from the main image data D according to the above equation (2), true image data D* cannot be acquired and the appropriate radiation image cannot be generated.

Therefore, as a preliminary process for generating the final radiation image by image process (that is, a preliminary process for calculating appropriate true image data D*), a preliminary process unique to the present invention, that is, process to accurately eliminate the Olag, the portion offset by lag, from the main image data D by use of the above-mentioned dark image data Od and the offset data O will be explained. Moreover, operation of the radiation image capturing apparatus 1 and the radiation image capturing system 50 according to the present invention will also be explained.

The control unit 22 of the radiation image capturing apparatus 1 may be configured to carry out the correction process, or the console 58 may be configured to carry out the correction process. In a case where the console 58 is configured to carry out the correction process, necessary information such as the main image data D, the offset data O, and the dark image data Od is transmitted from the radiation image capturing apparatus 1 to the console 58.

The reason why the appropriate true image data D* cannot be acquired even if the offset data O acquired as above is subtracted from the main image data D is thought as follows.

As described above, the offset data O acquired after readout process of the main image data D includes the Olag, the portion offset by lag which was generated by radiation irradiated to the radiation image capturing apparatus 1 at the time of photographing of a radiation image, other than the offset data Odark attributable to the dark electric charges generated and accumulated in each of the radiation detection elements 7 during the effective accumulation time T (refer to FIG. 19) after the readout process of the main image data D.

That is, as shown in the above equation (3), following equation holds:

$$O = O\text{lag} + O\text{dark} \quad (4)$$

Then, although the offset data Odark attributable to the dark electric charges is not necessarily read out as a value which increases in proportion to the effective accumulation time T similarly to the case of the dark image data Od, to simplify the explanation, it is assumed in the following that the dark electric charges are generated at a constant rate by a unit time, as shown in α of FIG. 21A. The offset data Odark or the dark image data Od is calculated by a value of integral of the effective accumulation time T of the dark electric charges generated at a constant rate by a unit time.

Moreover, as mentioned above, although there are many uncertainties concerning the mechanism of generation or continuation of the lag, it is assumed that the lags are generated at the time of irradiation with radiation and generation rate of the lags per a unit time decays exponentially to elapsed time t since the initiation of irradiation with radiation, as shown in β of FIG. 21A. The Olag, portion offset by lag, is calculated by a value of integral of the generation rate per a unit time.

If assumed as above, the relation between the dark image data Od, the Olag(D), portion offset by lag, which is included in the main image data D, and the offset data Od(D) attributable to the dark electric charges, and Olag, portion offset by lag, which is included in the offset data O, and the offset data Odark attributable to the dark electric charges become as one shown in the image view in FIG. 21B.

Note that in FIG. 21B, timing when the on-state voltage is applied to each scanning line 5 is indicated by arrows. Moreover, in FIG. 21B, illustration of reset process of each of the radiation detection elements 7 carried out between the readout process of the main image data D and acquisition process of the offset data O (refer to FIG. 19) is omitted. In addition, in FIG. 21A and FIG. 21B, illustration of the true image data D* attributable to the electric charges generated by irradiation with radiation. Note that the true image data D* generally has a significantly larger value than the dark electric charge or the lag.

Furthermore, since the main image data D includes the unillustrated true image data D*, the offset portion Olag (D), and the offset data Od(D) attributable to the dark electric charges, following equation holds:

$$D = D^* + O\text{lag}(D) + Od(D) \quad (5)$$

In this case, as described above, if it is configured that duration of the effective accumulation time T* in the acquisition process of the dark image data Od carried out at the time of readout process of the image data d before photographing of a radiation image (refer to FIG. 20) and duration of the effective accumulation time T in the case of the readout process of the main image data D (refer to FIG. 18) or acquisition process of the offset data O (refer to FIG. 19) become equal, the dark image data Od shown in FIG. 21B, the offset data Od(D) attributable to the dark electric charges included in the main image data D, and the offset data Odark attributable to the dark electric charges included in the offset data O become equal in terms of all the radiation detection elements 7.

That is, following equation holds:

$$Od = Od(D) = Odark \quad (6)$$

Then, in the above equation (4) or (5), instead of the Odark or Od(D), the dark image data Od acquired by the acquisition process of the dark image data Od can be used.

However, for example, in each of the radiation detection elements 7 connected to the line $L_n$ of the scanning line 5 to which the on-state voltage was applied when initiation of irradiation with radiation to the radiation image capturing apparatus 1 was detected, as shown in the image view shown below the arrows of FIG. 21B, the readout process of the main image data D or the acquisition process of the offset data O is carried out finally among the lines $L_1$ to $L_x$ of the scanning line 5 and therefore the value of the Olag, portion offset by lag, which is included in the offset data O, becomes small.

On the other hand, in each of the radiation detection elements connected to the line $L_{n+1}$ to which the readout process of the main image data D or the acquisition process of the offset data O is carried out first among lines $L_1$ to $L_x$ of the scanning line 5, value of Olag, portion offset by lag, which is included in the offset data, becomes large.

Therefore, even if the acquired offset data O is subtracted from the main image data D according to the above equation (2) as in the conventional method (that is, even if calculation of D*=D−O is carried out), it is considered that an appropriate true image data D* cannot be acquired.

Actually, for example, if a case where strong radiation is uniformly irradiated to the radiation image capturing apparatus 1 without a subject, that is, strong radiation having same dose is irradiated on the entire surface of the radiation incidence surface R (refer to FIG. 1), is assumed, in this case, true image data D* for each of the radiation detection elements 7, that is, the true image data D* attributable to the electric charges generated by irradiation of the radiation come to have the same value for all the radiation detection elements 7.

However, as described above, depending on the timing when the acquisition process of the offset data O is carried out in each of lines $L_1$ to $L_x$ of the scanning line 5, the value of the Olag, portion offset by lag, which is included in the offset data O, becomes large or small.

Then, as shown in FIG. 21B, the value of Olag, portion offset by lag, in the line $L_n$ of the scanning line 5 at which initiation of irradiation with radiation to the radiation image capturing apparatus 1 was detected was the smallest and the value of Olag, portion offset by lag, in the line $L_{n+1}$, the line immediately next to the line $L_n$ of the scanning line 5, becomes the largest.

Figure 22:
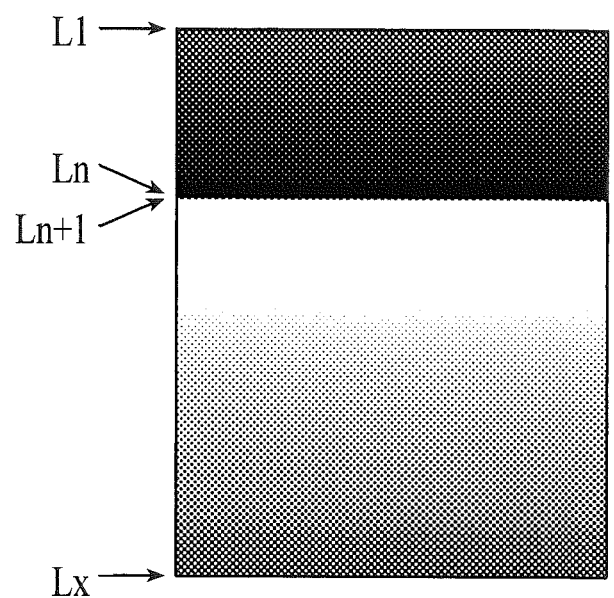
FIG. 22 is a view illustrating a condition where a gap is generated between a scanning line to which the on-state voltage was applied at the point of time when start of radiation was detected and a scanning line next to that scanning line.

Therefore, if process to subtract the offset data O from the main image data D is simply carried out, true image data D* thus calculated becomes larger from the first line $L_1$ toward line $L_n$ of the scanning line 5, as shown in FIG. 22, and after the value of the line $L_{n+1}$, the line immediately next to the line $L_n$, of the scanning line 5 becomes suddenly small to create a gap in the true image data D*, it becomes larger toward the final line of the scanning line 5. Note that in FIG. 22, difference for each scanning line 5 of the true image data D* is expressed in an exaggerated manner.

Thus, if calculation process of the true image data D: according to the conventional equation (2) is adopted, even though it was a case where radiation is uniformly irradiated to the radiation image capturing apparatus 1, there were cases where size of the true image data D* for each of the radiation detection elements 7 of each scanning line 5 varied other and a gap was generated between the line $L_n$ of the scanning line 5 which detected the initiation of irradiation with radiation and the line $L_{n+1}$, which is a line immediately next to the line $L_n$, in the true image data D*.

Therefore, in the present embodiment, true image data D* is calculated by correcting the main image data D by estimating the Olag (D), portion offset by lag, which is included in the main image data D, from the Olag, portion offset by lag, which is included in the offset data O, through utilization of a fact that the true image data D* can be calculated by $$D^* = D - Olag(D) - Od(D) \quad (7)$$

an equation derived from the above equation (6).

Specifically, for example, if it is assumed that the generation rate of the lags per a unit time decays exponentially to elapsed time t since the initiation of irradiation with radiation, as described above, and a and b are assumed as predetermined constants, it becomes possible to assume the generation rate of lags by a unit time as b exp (−a t).

Then, in terms of each of the radiation detection elements 7 connected to one scanning line 5, Olag(D), portion offset by lag, which is included in the main image data D, can be calculated according to the following equation (8), on an assumption that the elapsed time tp from the initiation of irradiation with radiation to start of readout process of the main image data D by application of the on-state voltage to the scanning line 5. Note that the elapsed time tp differs for each scanning line 5.

[Math. 1]

$$Olag(D) = \int_0^{tp} be^{-at} dt = \frac{b}{a}(1 - e^{-atp}) \quad (8)$$

Moreover, in terms of each of the radiation detection elements 7 connected to the scanning line 5, since time from application of the on-state voltage to the scanning line 5 for carrying out the readout process of the main image data D to acquisition process of the offset data is carried out is the above-mentioned effective accumulation time T, Olag, portion offset by lag, which is included in the offset data O, can be calculated according to the following equation (9). Note that in the present embodiment, the effective accumulation time T is the same in each scanning line 5, as mentioned above.

[Math. 2]

$$Olag = \int_{tp}^{tp+T} be^{-at} dt = \frac{b}{a}\{e^{-atp} - e^{-a(tp+T)}\} \quad (9)$$

$$\therefore Olag = \frac{b}{a}(1 - e^{-aT}) \cdot e^{-atp}$$

Then, from the above equations (8) and (9), following equation holds:

[Math. 3]

$$Olag(D): Olag = (1-e^{-atp}):(1-e^{aT}) \cdot e^{-atp} \quad (10)$$

Therefore, Olag(D), portion offset by lag, which is included in the main image data D, can be estimated on the basis of Olag, portion offset by lag, which is included in the offset data O, according to equation (11), which is a modification of the above equation (10):

[Math. 4]

$$Olag(D) = \frac{1-e^{-atp}}{(1-e^{-aT}) \cdot e^{-atp}} \times Olag \quad (11)$$

$$\therefore Olag(D) = \frac{e^{atp}-1}{1-e^{-aT}} \times Olag$$

Here, as mentioned above, although the effective accumulation time T is a predetermined constant value, tp is time which differs for each scanning line 5 and is elapsed time from the end of irradiation with radiation, which can be calculated from the time when irradiation with radiation was initiated or duration of irradiation.

Moreover, Olag, portion offset by lag, which is included in the offset data O, can be calculated by subtracting the dark image data Od from the offset data O according to the following equation (12) obtained by substituting the above equation (6) in an equation obtained by modification of the above equation (4):

$$Olag = O - Odark$$

$$\therefore Olag = O - Od \quad (12)$$

Therefore, in the present embodiment, if the above equation (6) is substituted in the above equation (7), following equation holds:

$$D^* = D - Olag(D) - Od \quad (13)$$

Therefore, in terms of each of the radiation detection elements 7 connected to each of the lines $L_1$ to $L_x$ of the scanning line 5, Olag(D), portion offset by lag, which is included in the main image data D, is calculated by substituting Olag, portion offset by lag, which is calculated from the offset data O and the dark image data Od or the elapsed time tp in the above equation (11), according to the equation (12) and Olag(D), portion offset by lag, which was thus calculated, the main image data D, and the dark image data Od are substituted in the above equation (13).

In the present embodiment, Olag(D), portion offset by lag, which is included in the main image data D, is estimated from the Olag, portion offset by lag, which is included in the offset data O, and the main data D is corrected so that Olag(D), portion offset by lag is accurately eliminated from the main image data D to calculate the true image data D*.

Note that in a case where the above-described preliminary process, that is, process for calculating appropriate true image data D* is carried out by the radiation image capturing apparatus 1, a final radiation image is generated by carrying out image process to the true image data D* for each of the radiation detection elements 7 thus calculated and therefore necessary information such as the calculated true image data D* is transmitted from the radiation image capturing apparatus 1 to the console 58.

As described above, according to the radiation image capturing apparatus 1 or the radiation image capturing system 50 according to the present embodiment, the control unit 22 or the console 58 subtracts the dark image data Od from the offset data O and calculates Olag, portion offset by lag, which is included in the offset data O, for each of the radiation detection elements 7.

Then, based on Olag, portion offset by thus calculated lag, Olag(D), portion offset by lag, which is included in the main image data D, is estimated and the main image data D is corrected by subtracting the Olag(D), portion offset by lag, from the main image data D read out by photographing of the radiation image.

Therefore, it becomes possible to accurately eliminate Olag(D), portion offset by lag, which is included in the main image data D. Then, it becomes possible to generate a final radiation image based on the main image data D from which the influence by lags is accurately eliminated, that is, true image data D*. Therefore, it becomes possible to accurately eliminate the influence by lags from the final radiation image and to improve the visual quality of the final radiation image.

Note that in the above-described example, the explanation was given of a case where the generation rate of the lags per a unit time decays exponentially to elapsed time t since the initiation of irradiation with radiation. However, the generation rate of the lags per a unit time does not always decay exponentially. Therefore, it is possible to carry out calculation process similar to the above by, for example, experimentally acquiring the generation rate of lags or the like and setting an approximation formula for approximating it.

Moreover, it is also possible to configure that an approximation formula of the generation rate of lags per a unit time is set and instead of carrying out integral treatment of the formula, as shown in above equation (9), for example, an approximation formula for approximating temporal change of Olag, portion offset by lag, itself, which is equivalent to the right side of the above equation (9) is set (that is, an approximation formula of a value after integration of the rate of generation of lags per a unit time) from the experiment result.

In the later-described second embodiment, as an approximation formula for approximating the temporal change of Olag, portion offset by lag, Olag, portion offset by lag is approximated in the form of power of the elapsed time t from the initiation of irradiation with radiation will be explained, as shown in later-described formula (14). However, it is also possible to utilize an approximation formula having such a form in the above-described first embodiment. Moreover, it is also possible to configure that an approximation formula having a form other than exponent function or power of the elapsed time t is used.

Second Embodiment

In the above-described first embodiment, a case was explained where the main image data D, which was read out in readout process (refer to FIG. 18 or FIG. 21B) carried out immediately prior to the acquisition process of offset data O (refer to FIG. 19 or FIG. 21B), is corrected on the basis of the offset data O, which was acquired by the acquisition process of the offset data O, and the like. That is, the main image data D and the offset data O acquired by one photographing of a radiation image were targets.

On the other hand, as mentioned above, it is known that in a case where radiation is irradiated again to the radiation image capturing apparatus 1 within a close time to the photographing of the radiation image (that is, within a time frame during which the influence by lags generated in the photographing of the radiation image remains) and another radiation image is photographed, Olag, portion offset by lag, generated by the previous photographing of a radiation image remains in each of the radiation detection elements 7 and is overlapped in the main image data D readout after the subsequent photographing of a radiation image as a so-called residual image.

Figure 23A:
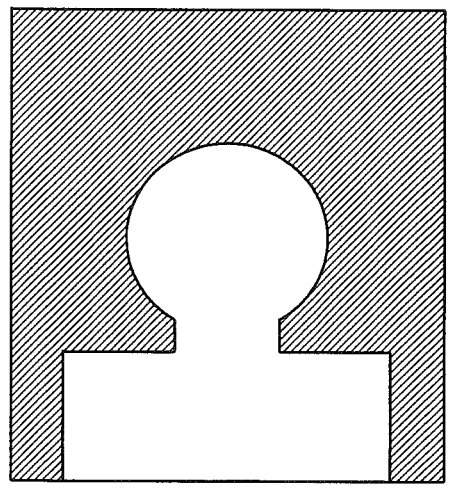
FIG. 23A is a view showing an example of an image photographing a head of a subject.
Figure 23B:
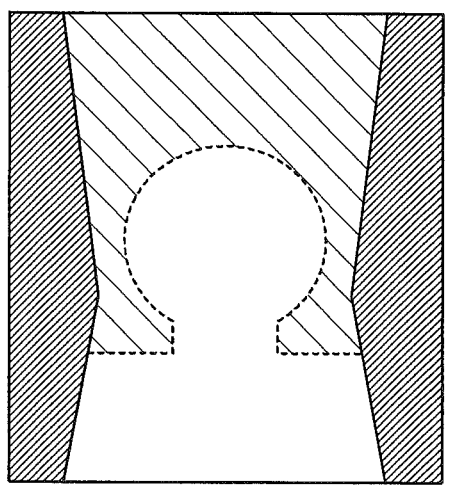
FIG. 23B is a view illustrating a condition where a residual image of the head of the subject is taken in an image of abdominal part taken subsequently.

That is, for example, if an abdominal part of a subject is photographed within a close time frame by use of the same radiation image capturing apparatus 1 after the head of the subject has been photographed, as shown in FIG. 23A, there may be a case where a residual image of the head of the subject, which was photographed in the previous photographing of a radiation image, is photographed in the subsequently taken image of the abdominal part of the subject. If such a phenomenon occurs, it becomes difficult to see the radiation image taken in the subsequent photographing and, in a case where the radiation image is used for, for example, diagnosis or the like, there is a possibility that the medical doctor who checks the radiation image would make a wrong diagnosis on the patient's illness.

If the method of the present invention explained in the first embodiment is adopted, it becomes possible to accurately eliminate the influence by Olag, portion offset by lag, which remains in the main image data D read out in the subsequent photographing and to acquire the main image data D where there is no residual image.

Hereinafter, in the second embodiment, explanation will be given of the elimination of Olag, portion offset by lag, which was generated in the previous photographing, from the main image data D.

Figure 24:
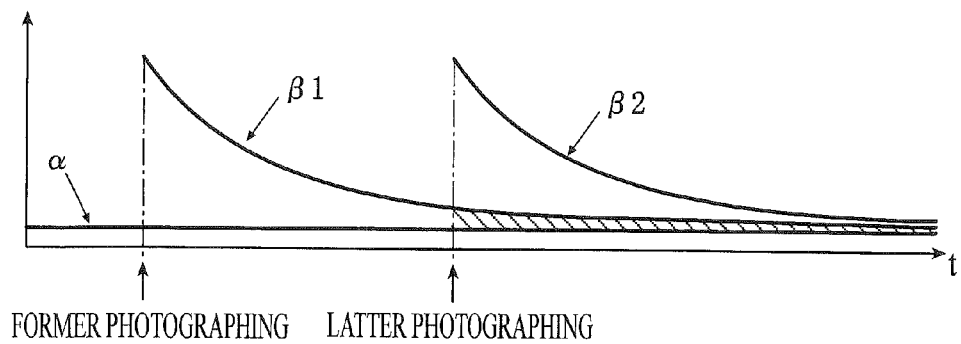
FIG. 24 is a view illustrating that the lags generated in the previous photographing are continuously generated in the subsequent photographing and thereafter.

In this case, the lag generated in the previous photographing continues to be generated after the previous photographing, as shown by β1 in FIG. 24, and also continues to be generated after the subsequent photographing, as shown by the shaded part in FIG. 24. Then, the continuously generated lags become the residual image overlapped in the main image data D acquired in the subsequent photographing. Therefore, the residual image by lags generated by the previous photographing is eliminated from the main image data D read out in the subsequent photographing as follows.

First, detection of initiation of irradiation with radiation to the radiation image capturing apparatus 1 can be carried out by monitoring the increase in the value of the image data d or the leaked data $d_{leak}$ read out by the readout process of the image data d before photographing of a radiation image or readout process of the leaked data $d_{leak}$ (refer to FIG. 14 to FIG. 16), similarly to the case of the above-described first embodiment, also in the subsequent photographing of a radiation image.

Moreover, it may be configured that the electric current detection unit 43 is provided to the bias line 9 or the wire connection 10 (refer to FIG. 17) or an electric current detection unit is provided to each scanning line 5 or to the wire 15c of the scanning drive unit 15 (refer to FIG. 7) to monitor the value of the electric current which flows through the wire connection 10, the scanning line 5, or the wire 15c so that initiation of irradiation with radiation can be detected, as explained in the first embodiment.

Note that the acquisition process of the dark image data Od carried out before photographing of a radiation image (refer to FIG. 20) has already been carried out before the previous photographing and is not carried out before the subsequent photographing. If the acquisition process of the dark image data Od is carried out before the subsequent photographing, a value to which not only the dark image data Od attributable to the dark electric charges generated in each of the radiation detection elements 7 but Olag, portion offset by lags, which were generated in the previous photographing and still remaining, is added, is acquired.

Then, after irradiation is performed to the radiation image capturing apparatus 1 in the subsequent photographing, similarly to the case of the first embodiment, readout process of the main image data D (refer to FIG. 18) and acquisition process of the offset data O (refer to FIG. 19) are carried out.

Figure 25:
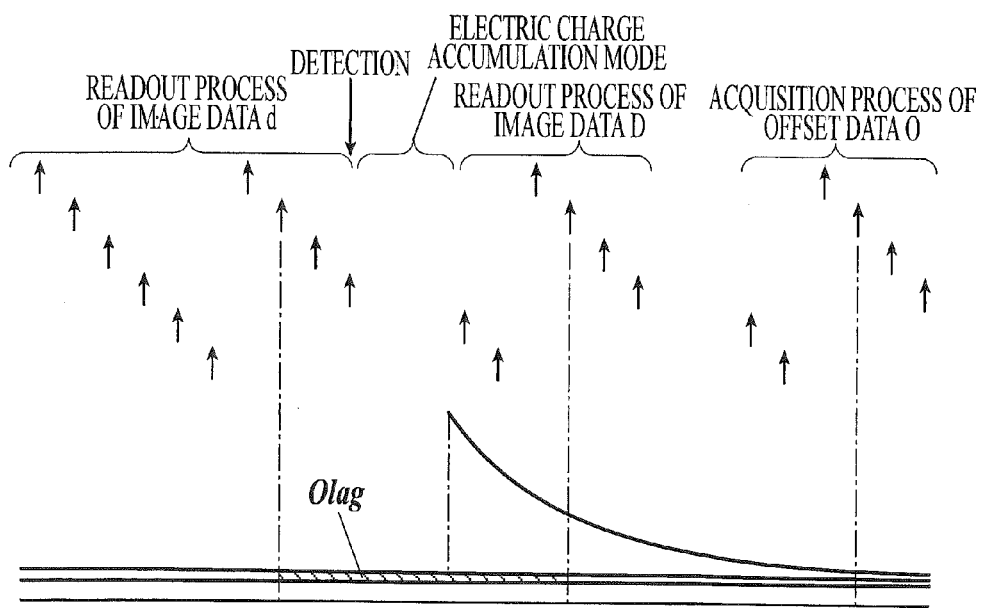
FIG. 25 is an image view illustrating a portion offset by the lags which were generated in the previous photographing and are superimposed on the main data read out in the subsequent photographing.

Olag, portion offset by lags, which were generated in the previous photographing and to be overlapped on the main image data D read out in the subsequent photographing, can be calculated as a value of integral of rate of generation of lags generated during the effective accumulation time T, which is from the application of the on-state voltage to the final scanning line 5 in the readout process of the image data d until the main image data D is read out after the on-state voltage is applied to the scanning line 5 in the readout process of the main image data D, per a unit time, as shown in FIG. 25.

Therefore, Olag, portion offset by lags, which were generated in the previous photographing and to be overlapped in the main image data D readout in the subsequent photographing, can be calculated by use of the above equation (9) shown in the above-described first embodiment without any change.

Moreover, as described above, instead of using the above-mentioned equation (9) without any change, that is, instead of setting that the rate of generation of lags per a unit time is approximated by the exponential function and Olag, portion offset by lags, is calculated exponentially as a value of integral of the approximation, it is also possible to configure that, for example, Olag, portion offset by lags, which were generated in the previous photographing and to be overlapped in the main image data D to be read out in the subsequent photographing, itself is set in the form of power of elapsed time t from the initiation of irradiation with radiation in the previous photographing, according to the following equation (14):

$$O\text{lag} = O\text{lag\_pre} \cdot y \cdot t^z \qquad (14)$$

Here, Olag_pre in the above equation (14) indicates Olag, portion offset by lags in the previous photographing, which is calculated for each of the radiation detection elements 7 by subtracting the dark image data Od from the offset data O acquired by the acquisition process of the offset data O in the previous photographing according to the above-mentioned equation (12).

In this case, constants y and z in the above equation (14) can be determined previously through an experiment as follows.

That is, as shown in FIG. 18, for example, after the readout process of the main image data D is carried out by irradiating radiation to the radiation image capturing apparatus 1, reset process of each of the radiation detection elements 7, shift to the electric charge accumulation mode, and acquisition process of the offset data O as shown in FIG. 19 are repeatedly carried out and the dark image data Od is subtracted from each of offset data O read out by each acquisition process of the offset data O to calculate Olag, portion offset by lags, which were generated in the first photographing, for each acquisition process of the offset data O.

Figure 26:
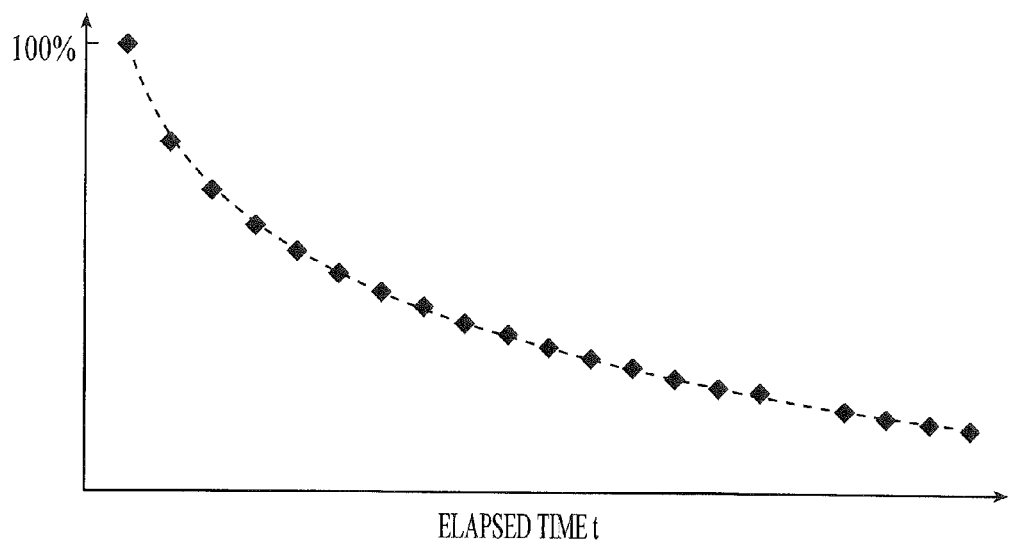
FIG. 26 is a graph plotting a relative ratio of the portion offset by the lags acquired by acquisition process of the first offset data to the portion offset by the lags acquired by acquisition process of acquisition process of each offset data.

Then, each of Olag, portion offset by lags, which were thus calculated for acquisition process of each offset data O, is plotted on a graph for elapsed time t which is from the initiation of irradiation with radiation until the acquisition process of each offset data is carried out, as shown in FIG. 26, for example, and is used an approximation formula for determining the constants y and z in the above equation (14).

Thus, it becomes possible to previously set Olag, portion offset by lags, which were generated in the previous photographing and to be overlapped in the main image data D read out in the subsequent photographing, can be set in the form of power of the elapsed time t.

Note that in FIG. 26, a relative ratio of Olag, portion offset by lags, which are acquired for each acquisition process of each offset data O and generated in the first photographing, to the portion offset by lags, which are acquired by the acquisition process of the first offset data O (that is, Olag_pre in the above equation (14)), in other words, briefly speaking, a value equivalent to the portion of y·t² in the above equation (14) is plotted.

On the other hand, in each of the above-mentioned cases, t in the above equation (14) and tp in the above equation (9) are, as described above, elapsed time from initiation of irradiation with radiation in the previous photographing and duration of the elapsed times t and tp differs for each scanning line 5.

In order to determine the elapsed times t and tp, it may be configured that the control unit 22 counts the elapsed times t and tp, for example, or the control unit 22 calculates the elapsed times t and tp based on the number of frames for which readout process of the image data d was carried out between the previous photographing and the subsequent photographing or on the number of frames for which reset process of each of the radiation detection elements 7 was carried out.

In a case where the process for calculating Olag, portion offset by lags, which were generated in the previous photographing and are to be overlapped in the main image data D read out in the subsequent photographing, is carried out according to the above equation (14) or the above equation (9) by the console 58, the control unit 22 transmits necessary information such as the elapsed times t and tp to the console 58.

Then, when correction process is carried out to the main image data D read out in the subsequent photographing by the control unit 22 or the console 58, Olag, portion offset by lags, which were generated in the previous photographing, the main image data D, and the dark image data Od are substituted in the following equation (15) to correct the main image data D acquired in the subsequent photographing so that true image data D* is calculated.

$$D^* = D - O\text{lag} - Od \quad (15)$$

In the present embodiment, Olag, portion offset by lags, which were generated in the previous photographing, is thus calculated and estimated and based thereon, the main image data D acquired in the subsequent photographing is corrected to accurately eliminate at least Olag, portion offset by lags, which were generated in the previous photographing, so that the true image data D* is calculated.

Note that it the above equation (15) is expressed by use of the above equation (14) or the above equation (12), following equation holds:

$$\begin{aligned} D^* &= D - O\text{lag} - Od \\ &= D - Od - O\text{lag\_pre} \times y \cdot t^z \\ \therefore D^* &= D - Od - (O - Od) \times y \cdot t^z \end{aligned} \quad (16)$$

Note that the offset data O in (O−Od) in the above equation indicates the offset data O acquired by acquisition process of the offset data O in the previous photographing, as described above. Moreover, same is applied to a case where the above equation (9) or the like is used instead of the above equation (14).

Thus, in the above-described second embodiment, a case was explained where the main image data D acquired by the subsequent photographing is corrected by use of the previously acquired dark image data Od and the offset data O acquired in the previous photographing, without using the offset data O acquired by the acquisition process of the offset data O (refer to FIG. 25) carried out after the readout process of the main image data D in the subsequent photographing.

However, it is also possible to configure that in the subsequent photographing, the main image data D read out in the subsequent photographing is corrected by use of the offset data O acquired in the subsequent photographing.

In this case, for example, according to the above equation (2), which expresses a principle when the main image data D is corrected by use of the offset data O, the main image data D is corrected and the true image data D* is calculated.

$$D^* = D - O \quad (2)$$

However, in this case, as shown in FIG. 25, similarly to the case where Olag, portion offset by lag, which was generated in the previous photographing, is overlapped on the main image data D which is read out in the subsequent photographing, Olag, portion offset by lag, which was generated in the previous photographing, is overlapped on the offset data O acquired in the subsequent photographing.

Moreover, in this case, elapsed times t and tp, which are time from initiation of irradiation with radiation in the previous photographing, differ for the readout process of the main image data D and acquisition process of the offset data O in the subsequent photographing. Therefore, Olag, portion offset by lag, which was generated in the previous photographing and is overlapped on the main image data D read out in the subsequent photographing, and Olag, portion offset by lag, which was generated in the previous photographing and is overlapped on the offset data O acquired by the subsequent photographing have different values.

If elapsed time from the initiation of irradiation with radiation in the previous photographing until readout process of the main image data D in the subsequent photographing is expressed as t(D) and elapsed time from the initiation of irradiation with radiation in the previous photographing until acquisition process of the offset data O in the subsequent photographing is expressed as t(O), Olag, portion offset by lag, which was generated in the previous photographing and is overlapped on the main image data D and the offset data O acquired by the subsequent photographing respectively, is expressed by use of the above equation (14) as follows:

$$O\text{lag} = O\text{lag\_pre} \times y \cdot t(D)^z \quad (17)$$

$$O\text{lag} = O\text{lag\_pre} \times y \cdot t(O)^z \quad (18)$$

Then since Olag, portion offset by lag, is overlapped on the main image data D and the offset data O acquired in the subsequent photographing respectively, if Olag, portion offset by lags, which were generated in the previous photographing and expressed by the above equations (17) and (18), is respectively subtracted from the main image data D or the offset data O acquired in the subsequent photographing, as $$D - O\text{lag\_pre} \times y \cdot t(D)^z \quad (19)$$

$$O - O\text{lag\_pre} \times y \cdot t(O)^z \quad (20)$$

influence by Olag, portions offset by lags, which were generated in the previous photographing, can be eliminated.

Then, as shown in the equation (21) below, it is possible to calculate the true image data D* by substituting the equation (19) or equation (20) for D or O in the above equation (2). Note that it is needless to say that same is applied to a case where the above equation (9) or the like it used instead of the above equation (14).

$$D^* = (D - O\mathrm{lag\_pre} \times y \cdot t(D)^z) - (O - O\mathrm{lag\_pre} \times y \cdot t(O)^z) \qquad (21)$$

According to such configuration, it becomes possible to accurately correct the main image data D acquired in the subsequent photographing based on the offset data O acquired in the subsequent photographing in a condition where the influence of Olag, portion offset by lags generated in the previous photographing, from the main image data D or the offset data O acquired in the subsequent photographing and to calculate the true image data D* without being influenced by Olag, portion offset by lags generated in the previous photographing.

Note that it is also possible to configure that by applying the method of the above-described first embodiment to the main image data D and the offset data O, the main image data D read out in the subsequent photographing is corrected by the offset data O acquired in the subsequent photographing, or the like, taking a fact that Olag, portion offset by lags generated in the previous photographing, is overlapped on the main image data D and the offset data O acquired in the subsequent photographing respectively. However, in this case, the method of the first embodiment is applied to the main image data D or the offset data O acquired in the subsequent photographing after Olag, portion offset by lags generated in the previous photographing, is respectively subtracted, as shown in the above equation (19) or the equation (20).

As described above, according to the radiation image capturing apparatus 1 or the radiation image capturing system 50 according to the present embodiment, the control unit 22 or the console 58 estimates Olag, portion offset by lags generated in the previous photographing, and subtracts Olag, portion offset by lags generated in the previous photographing, to correct the main image data D.

Therefore, it becomes possible to accurately eliminate Olag, portion offset by lags generated in the previous photographing, included in the main image data D. Moreover, it becomes possible to generate a final radiation image based on the main image data D from which the influence of lags is eliminated, that is, true image data D*. Therefore, it becomes possible to eliminate the influence of lags from the final radiation image and to improve the quality of the final radiation image.

Note that in the second embodiment also, explanation was given of a case where Olag, portion offset by lags generated in the previous photographing, which is overlapped on the main image data D read out in the subsequent photographing, is set in the form of power of the elapsed time t from the initiation of irradiation with radiation, or a case where it is assumed that the rate of generation of lags per a unit time is exponentially attenuated from the initiation of irradiation with radiation.

However, instead of using the above equation (14) or equation (9), it is also possible to set an approximation formula which approximates the rate of generation of lags per a unit time in a form other than exponent function and to carry out integral treatment of the approximation formula, or to calculate Olag, portion offset by lags generated in the previous photographing, on the basis of an equation which approximates temporal alteration or the like of Olag, portion offset by lags, by the form than power of the elapsed time t.

In addition, for example, in a case where the radiation image capturing apparatus 1 is irradiated with radiation three times and photographing of a radiation image is carried out three times in a consecutive manner within a relatively short period of time, both of Olag, portion offset by lags generated by irradiation with radiation in the first photographing, and Olag, portion offset by lags generated by irradiation with radiation in the second photographing, are overlapped on the main image data D acquired in the third photographing of a radiation image or the offset data O acquired in the subsequent acquisition process of the offset data O.

Thus, in a case where a plurality of radiation images are photographed in a consecutive manner by irradiation with radiation to the radiation image capturing apparatus 1 a plurality of times within a relatively short period of time, all Olags, portion offset by lags generated in photographing carried out previously, are overlapped on the main image data D or the offset data O read out in the latter photographing.

Therefore, in a case where photographing of radiation image is carried out a plurality of times, the main image data D or the like is corrected by subtracting all Olags, portion offset by lags generated in the previous photographing, from the main image data D or the offset data O.

Note that at this time as understood from the above equation (9), equation (14), or the like, the longer time between photographings becomes, that is, the longer the elapsed times t and tp become, the smaller Olag, portion offset by lags generated in previous photographing, becomes. Therefore, it is also possible to configure that, for example, in terms of the previous photographing until which the elapsed times t and tp longer than predetermined period of time have passed, the overlapping portion on the main image data D or the like read out in the subsequent photographing by Olag, portion offset by lags generated in the previous photographing, is ignored and Olag, portion offset by the lags, is not a target of calculation such as the above equation (15).

Third Embodiment

As described above, there are still many uncertainties concerning the mechanism of generation and continuation of lags generated by radiation toward the radiation image capturing apparatus 1. Moreover, configuration of the radiation detection element 7 where a lag is generated, configuration of the TFT 8 which may be related to leakage of a lag, or a value of the bias voltage applied to the radiation detection element 7 or a value of the off-state voltage applied to the TFT 8 is changed to other configuration or a value, there is a possibility that the mechanism of generation or continuation of lags changes or the like and the form of the approximation formula or the like to the elapsed time t (hereinafter, the elapse time tp in a case of the above equation (9) and the like is included) of Olag, portion offset by lags may change.

Therefore, there is a possibility that the form or the like of the approximation formula used may differ depending on the model or the like of the radiation image capturing apparatus 1 and an approximation formula corresponding to the radiation image capturing apparatus 1 is appropriately set.

Hereinafter, some methods for determining an approximation formula to elapsed time t of Olag, portion offset by lags, or constants y and z used in the above equation (14) will be explained.

[Determination Method 1]

In the radiation image capturing apparatus 1 having a configuration explained in the first embodiment or the like, change of Olag, portion offset by lags generated in the first photographing, to the elapsed time t from the initiation of irradiation with radiation, that is, attenuation tendency, is the tendency shown in FIG. 26. Such an experimental result was obtained by irradiating radiation to the radiation image capturing apparatus 1, carrying out readout process of the main image data D, and subsequently carrying out shift of each of the radiation detection elements 7 from reset process to electric charge accumulation mode to acquisition process of offset data O in a repeated manner, as shown in FIG. 19.

Therefore, if, for example, a scanning line 5 to which the on-state voltage was applied at the point of time when irradiation with radiation to the radiation image capturing apparatus 1 was detected was the 500$^{th}$ line of the scanning lines 5, in the present embodiment, application of the on-state voltage is started from the 501$^{st}$ line of the scanning line 5, a line to which the on-state voltage must be applied next (in the case of the FIG. 18, line $L_{n+1}$ of the scanning line 5) to carry out the readout process of the main image data D, and in the acquisition process of each offset data O to be carried out repeatedly subsequently, the same 501$^{st}$ line of the scanning line 5 is the scanning line 5 where acquisition process is started in the acquisition process of any of the offset data O.

Therefore, the constants y or z in the above equation (14) obtained by approximating the result shown in FIG. 26 can be applied only to a case where readout process of the main image data D or acquisition process of the offset data O is carried out from the 501$^{st}$ line of the scanning line 5 and there is a possibility that the constants cannot be applied to a case where readout process of the main image data D or acquisition process of the offset data O is carried out from the other line of the scanning lines 5.

Figure 27:
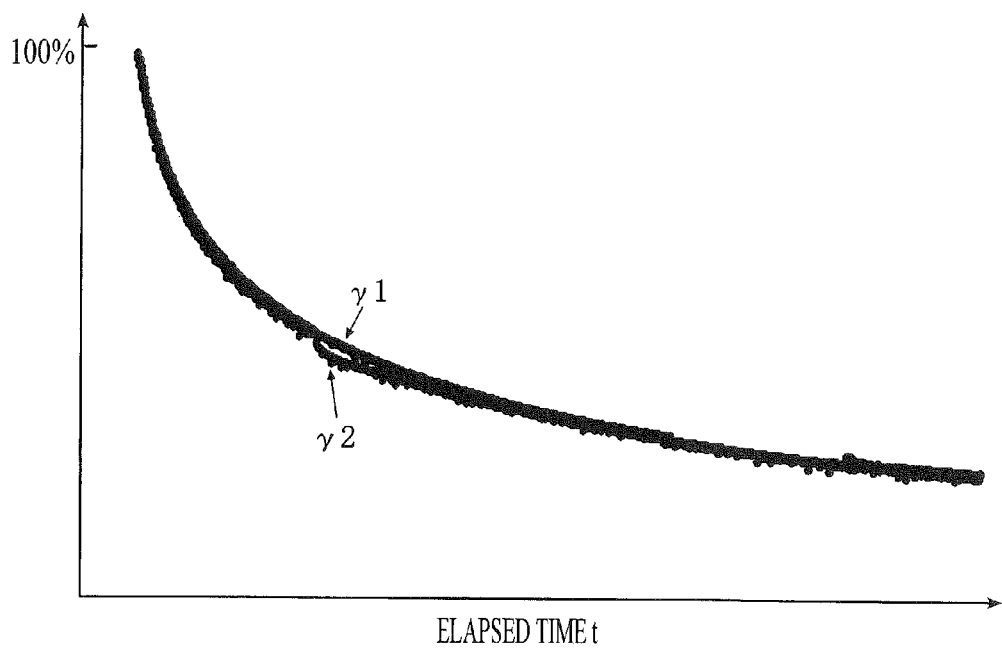
FIG. 27 is a graph showing that attenuation tendencies of the relative ratio shown in FIG. 26 to elapsed time from initiation of irradiation with radiation become approximately same even if starting scanning lines differ.

Regarding this point, in the experiment using the radiation image capturing apparatus 1 having a configuration explained in the first embodiment or the like, it is understood that even if the scanning lines 5 from which the readout process of the main image data D and the acquisition process of the offset data O were started (hereinafter referred to as starting scanning line) are scanning lines 5 having difference line numbers, attenuation tendency of ratio of Olag, portion offset by lags acquired in the repeatedly-carried out acquisition process of each offset data O, relative to Olag_pre, portion offset by lags acquired in the acquisition process of the offset data O at the time of irradiation with radiation, becomes almost same, as shown in FIG. 27.

Note that in FIG. 27, a case where the starting scanning lines 5 from which the readout process of the main image data D and the acquisition process of the offset data O were started were 453$^{rd}$ line (y1) and 965$^{th}$ line (y2) of the scanning line 5 is shown.

Therefore, at least by the radiation image capturing apparatus 1 having a configuration explained in the first embodiment or the like, it is possible to approximate Olag, portion offset by lags, by one approximation formula in which same constants y and z are applied to the above equation (14) in terms of all the scanning lines 5, irrespective of which scanning line 5 was the starting scanning line 5 from which the readout process of the main image data D and the acquisition process of the offset data O was started.

[Determination Method 2]

However, depending on the radiation image capturing apparatus 1, there may be a case where the constants y and z to be applied to the above equation (14) for approximating Olag, portion offset by lags, or the like differ depending on which scanning line 5 is the starting scanning line 5 for the readout process of the main image data D or the acquisition process of the offset data O. That is, depending on which scanning line 5 was the starting scanning line 5 from which the readout process of the main image data D or the acquisition process of the offset data O is started, form of the approximation formula for approximating Olag, portion offset by lags, may differ.

Therefore, in such a case, for example, a table for correlating the line numbers of the starting scanning lines 5 from which the readout process of the main image data D and the acquisition process of the offset data O were started and constants y and z, or a table for correlating the above-mentioned line numbers of the starting scanning lines 5 and the approximation formula is provided in advance.

Then, it is possible to configure that by referring to the table, the constants y and z or the approximation formula is obtained according to the line numbers of the starting scanning lines 5 from which the readout process of the main image data D and the acquisition process of the offset data O were started, and based thereon, Olag, portion offset by lags generated in the previous photographing, which is to be overlapped in the main image data D to be read out in the subsequent photographing, is calculated.

[Determination Method 3]

On the other hand, as shown in FIG. 27, according to the radiation image capturing apparatus 1 having a configuration explained in the first embodiment or the like, it was possible to use one approximation formula in which same constants y and z were applied to the above equation (14), at least in terms of the starting scanning line 5, no matter which line number of the scanning line 5 was the starting scanning line 5 from which the readout process of the main image data D or the acquisition process of the offset data O was started, as described above.

However, it is not known whether it is possible to use the same constants y and z of the starting scanning line 5 or the same approximation formula for a scanning line 5 to which the on-state voltage is applied next to the starting scanning line 5 in the readout process of the main image data D or the like, or for a scanning line 5 to which the on-state voltage is applied next to the above-mentioned scanning line 5 for carrying out readout process.

That is, even if the starting scanning line 5 indicated as the line $L_{n+1}$ of the scanning line 5 in FIG. 18 or FIG. 19 is the 453$^{rd}$ line (y1), the 965$^{th}$ line (y2) shown in FIG. 27, or another line of the scanning line 5, as shown in FIG. 27, it was possible to use the constants y and z which are same as the constants y and z applied to the above equation (14) in terms of the starting scanning line 5.

However, in a case where the starting scanning line 5 is line $L_{n+1}$ of the scanning line 5 in FIG. 18 or FIG. 19, it is not known whether it is possible to apply the constants y and z, which are the same constants y and z in the case of the starting scanning line 5 (that is, line $L_{n+1}$ of the scanning line 5), for a line $L_{n+2}$, to which the on-state voltage is applied next to read out offset data O, to the above equation (14) in order to acquire an approximation formula for elapsed time t of Olag, portion offset by lags. Same is applied to each of line $L_{n+3}$ and subsequent lines of the scanning line 5.

Moreover, although it is possible to apply the same constants y and z or same approximation formula in terms of the scanning line 5 other than the starting scanning line 5, there may be a case where it would be better to apply different constants y and z to the above equation (14) or to set other approximation formula for each of scanning line 5 other than the starting scanning line 5 in order to improve accuracy of calculation (approximation) of Olag, portion offset by lags.

Figure 28A:
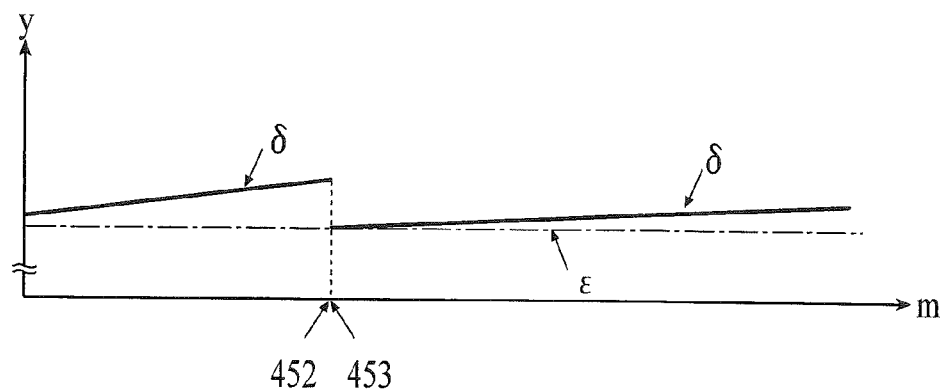
FIG. 28A is a graph plotting a constant y for each line number of the scanning lines.
Figure 28B:
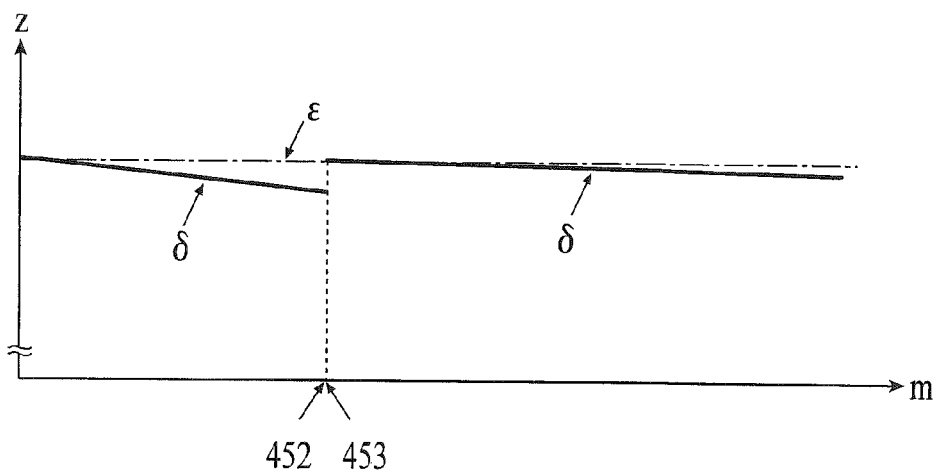
FIG. 28B is a graph plotting a constant z for each line number of the scanning lines.

For example, the graphs shown in FIG. 28A and FIG. 28B are graphs each showing a case where the starting scanning line 5 is the 453$^{rd}$ line of scanning line 5, constants y and z are respectively plotted against line number m of line $L_m$ of scanning line 5 in a case where a curve line obtained by plotting relative ratio of Olag, portion offset by lags acquired in repeatedly carried out acquisition process of each offset data O, to Olag_pre, portion offset by lags acquired in acquisition process of offset data O at the time of irradiation with radiation (that is, the member of $y \cdot t^z$ in the above equation (14)), against elapsed time t from initiation of irradiation with radiation is approximated in the form of $y \cdot t^z$.

Note that the straight lines indicated by 5 in FIG. 28A and FIG. 28B indicate constants y and z for each line $L_m$ of scanning line 5 as described above. Moreover, dashed-dotted lines indicated by ∈ in FIG. 28A and FIG. 28B indicate constants y and z in the above described determination method 1 and show a case where the constants y and z at the starting scanning line 5 are applied to each line $L_m$ of scanning line 5 with no exception.

Moreover, when the constants y and z acquired for each line $L_m$ of scanning line 5 are plotted for line number m of line $L_m$ of scanning line 5 as described above, the constants y and z vary in vertical axis direction for line number m in the graphs of FIG. 28A and FIG. 28B. In FIG. 28A, a result of a case where each constant y is subject to straight-line approximation before and after starting scanning line 5 is shown and in FIG. 28B, a result of a case where each constant z is subject to straight-line approximation before and after starting scanning line 5 is shown.

In addition, in FIG. 28A and FIG. 28B, a case where starting scanning line 5 is the 453$^{rd}$ line is shown. However, it is known that same results are obtained in a case where starting scanning line 5 is another line of scanning line 5.

Then, no matter which line number of the scanning line 5 is the starting scanning line 5, it was possible to apply the same constants y and z to the above equation (14) in terms of the starting scanning line 5, as described above, and it is known that same constants y and z can be applied in terms of a scanning line 5 next to the starting scanning line 5 (that is, second scanning line 5) for the next scanning line 5 no matter which line number of scanning line 5 is the starting scanning line 5 and in terms of the third or subsequent scanning line 5, same constants y and z can be applied to the above equation (14) in terms of the scanning lines 5 in the same order.

Then, in a case where it is possible to apply same constants y and z to the above equation (14) in terms of starting scanning lines 5 or scanning lines 5 in the same order from starting scanning lines 5, for example, it is possible to apply the constants y and z or an approximation formula for calculating Olag, portion offset by lags overlapped on the main image data D which is read out when an on-state voltage is applied to the starting scanning line 5 or other scanning line 5, as follows.

That is, for example, an image readout number is defined by assuming that an image readout number of a scanning line 5 from which the readout process of main image data D or the acquisition process of the offset data O was started, in other words, starting scanning line 5, is No. 1, an image readout number of a scanning line 5 to which an on-state voltage is applied next and readout process was carried out is No. 2, and image readout numbers for third, fourth, . . . scanning lines 5 to which on-state voltage is applied subsequently are No. 3, No. 4, and so on.

If the image readout number is thus defined, the image readout numbers amount from 1 to all the number of scanning lines 5. Note that although starting scanning line 5 differs for each photographing, once a starting scanning line 5 is determined, the scanning lines 5 and the image readout numbers make a pair, respectively.

Figures 29, 30:
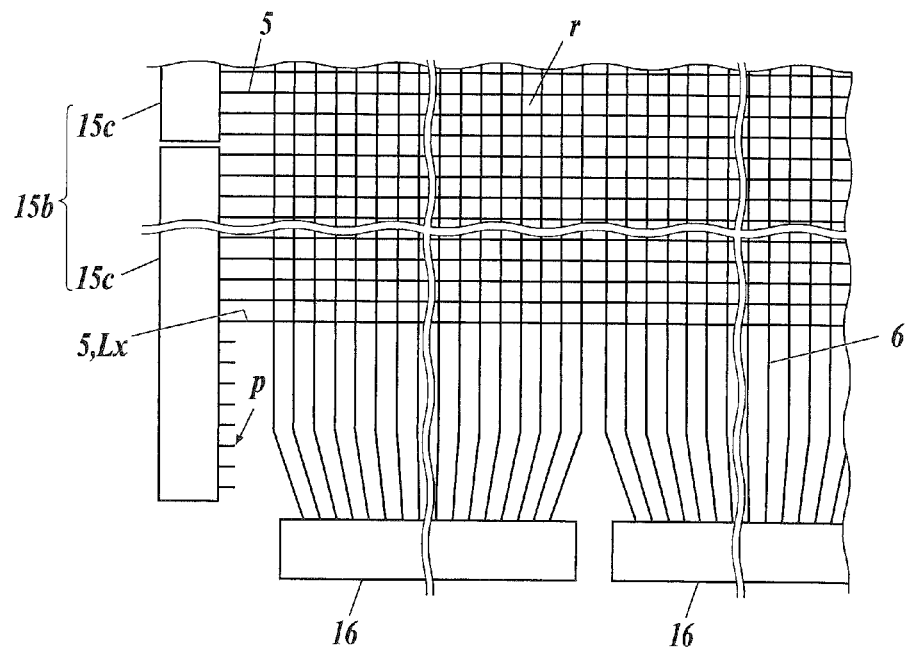
FIG. 29 is a view showing a table correlating image readout numbers with y and z.
FIG. 30 is a view showing a gate driver and a gate IC having an unconnected terminal.

Then, a table for correlating, for example, image readout numbers shown in FIG. 29 and constants y and z to be applied to the above equation (14) is prepared in advance by carrying out an experiment shown above or the like in advance.

Then, it is possible to configure that when calculating Olag, portion offset by lags, the table is referred to calculate constants y and z or an approximation formula on the basis of the image readout number allotted to each scanning line 5 according to starting scanning line 5 from which readout process of main image data D or acquisition process of offset data O was carried out in the previous photographing, and based thereon, Olag, portion offset by lags generated in the previous photographing, which is overlapped on main image data D to be read out in the subsequent photographing, is calculated.

Note that it is also possible to configure that instead of preparing the table for correlating the image readout numbers and constants y and z, as shown in FIG. 29, a table for correlating image readout numbers and approximation formulae, which is not shown, is prepared.

Moreover, if the above-described experiment is carried out a plurality of times, starting scanning line 5 changes for each experiment. Therefore, utilizing this, the above-described experiment is carried out a plurality of times and constant y (or constant z) corresponding to image readout number is acquired for the plurality of times for each image readout number. Then, it is possible to configure that an average value or the like of each constant y (or constant z) for each image readout number is calculated and a table is created so as to correlate each image readout number and the average value of the constant y (or constant z) or the like. If thus structured, it becomes possible to accurately calculate constants y and z to be applied to the above equation (14) (that is, an average value of constants y and z, or the like) based on the constants y and z acquired in a condition where starting scanning lines 5 differ.

In addition, it is possible to configure that, as shown in FIG. 28A and FIG. 28B, for example, constants y and z acquired for each line $L_m$ of scanning line 5 (or an average value of constants y and z, or the like) are plotted for line number m of the line $L_m$ of scanning line 5 and on the basis of, for example, approximating a result thereof by straight-line approximation or the like before and after scanning line 5 to determine constants y and z to be correlated with image readout numbers.

[Determination Method 4]

On the other hand, as shown in the above-described determination method 3, in a case where starting scanning lines 5 differ (refer to FIG. 27), even if same constants y and z can be applied to the above equation (14) for starting scanning lines 5, there may be a case where same constants y and z cannot be applied to the above equation (14) for scanning lines 5 having same numbers for the subsequent scanning lines 5 (that is, each of scanning lines 5 having No. 2 or subsequent number of the above-mentioned image readout number).

Moreover, there may be a case where an approximation formula for approximating Olag, portion offset by lags, differs or constants y and z to be applied to the above equation (14) differs, depending on which scanning line 5 is starting scanning line 5 in the first place.

Therefore, in such a case, it is possible to configure that a table which correlated approximation formula or constants y and z for each scanning line 5 is prepared in advance for each case where starting scanning line 5 differs. That is, in this case, if there exist 1000 scanning lines 5 on the detecting part P, for example, 1000 tables, which are the same amount as the number of all the scanning lines 5 which can become starting scanning line 5 and by which an approximation formula or constants y and z are correlated with each of 1000 scanning lines 5, are prepared in advance.

If configured as shown in the above-described determination method 1 to 4, the effect of the radiation image capturing apparatus 1 or the radiation image capturing system 50 explained in the first and second embodiment can be more accurately produced.

Note that the above-described experiment for acquiring attenuation tendency of Olag, portion offset by lags generated in the first photographing, to elapsed time t from initiation of irradiation with radiation, that is, the experiment for acquiring constants y and z of the above equation (14) or the like is to carry out readout process of main image data D by irradiating radiation to the radiation image capturing apparatus 1, and subsequently, carry out reset process of each of radiation detection elements 7, shift to electric charge accumulation mode, and acquisition process of offset data O in a repeated manner, as shown in FIG. 18.

Therefore, as described above, if scanning line 5 to which on-state voltage was applied at the point of time when irradiation with radiation to the radiation image capturing apparatus 1 was, for example, $500^{th}$ line, for the following readout process of main image data D or acquisition process of each offset data O, each process is carried out by starting application of on-state voltage to the $501^{st}$ line of scanning line 5 to which on-state voltage must be applied next.

However in a case where initiation of irradiation with radiation is detected when radiation is irradiated to the radiation image capturing apparatus 1 in the former photographing and latter photographing in actual photographing of radiation images as in the second embodiment, scanning lines 5 to which on-state voltage was applied at the point of time when radiation was irradiated to the radiation image capturing apparatus 1 generally differ in the former photographing and the latter photographing. Therefore, starting scanning lines 5 to which on-state voltage is applied in the readout process of main image data D or acquisition process of offset data O to start each process are generally different starting scanning lines 5.

Therefore, in a case where each method explained in the present embodiment is applied to a case explained in, for example, the second embodiment, attention is required as follows:

That is, for example, in a case where the radiation image capturing apparatus 1 is irradiated with radiation three times and photographing of images are carried out three times within a relative short period of time, both Olag, portion offset by lags generated in the first irradiation with radiation, and Olag, portion offset by lags generated in the second irradiation with radiation, are overlapped in main image data D acquired in the third photographing of a radiation image or offset data O acquired by subsequent acquisition process.

At this time, Olag, portion offset by lags generated by irradiation with radiation in the first photographing, which is overlapped on main image data D or the like acquired in the third photographing of a radiation image, is calculated according to constants y and z or an approximation formula determined on the basis of line number of starting scanning line 5 from which readout process of main image data D or the like was started, or the like, in the first photographing.

However, Olag, portion offset by lags generated by irradiation with radiation in the second photographing, which is overlapped on main image data D or the like acquired by the third photographing of a radiation image, is calculated according to constants y and z or an approximation formula determined on the basis of line number of starting scanning line 5, from which readout process of main image data D or the like was started, or the like, in the second photographing.

Thus, in a case where each method explained in the present embodiment is applied, starting scanning line 5 differs for each photographing of a radiation image and therefore it is necessary to accurately change constants y and z or approximation formula based on the starting scanning line 5 in each photographing.

Meanwhile, depending on the radiation image capturing apparatus 1, there may exist a so-called non-connecting terminal P, a gate driver 15b of scan diving means 15 or a gate IC 15c which configures the gate driver 15b (hereinafter collectively referred to as gate driver 15b) to which scanning line 5 is not connected.

In a case where such a gate driver 15b is used, when on-state voltage is sequentially applied to each of lines $L_1$ to $L_x$ of scanning line 5 from gate driver 15b in the above-described readout process of image data D, acquisition process of offset data O, or acquisition process of dark image data Od before photographing of a radiation image, the on-state voltage is sequentially applied from, for example, a terminal of the gate driver 15b to which the first line $L_1$ of the scanning line 5 is connected, and after the on-state voltage is applied to a terminal to which the final line $L_x$ of the scanning line 5 is connected, on-state voltage is sequentially applied to non-connecting terminal p to which scanning line 5 is not connected.

Figure 31:
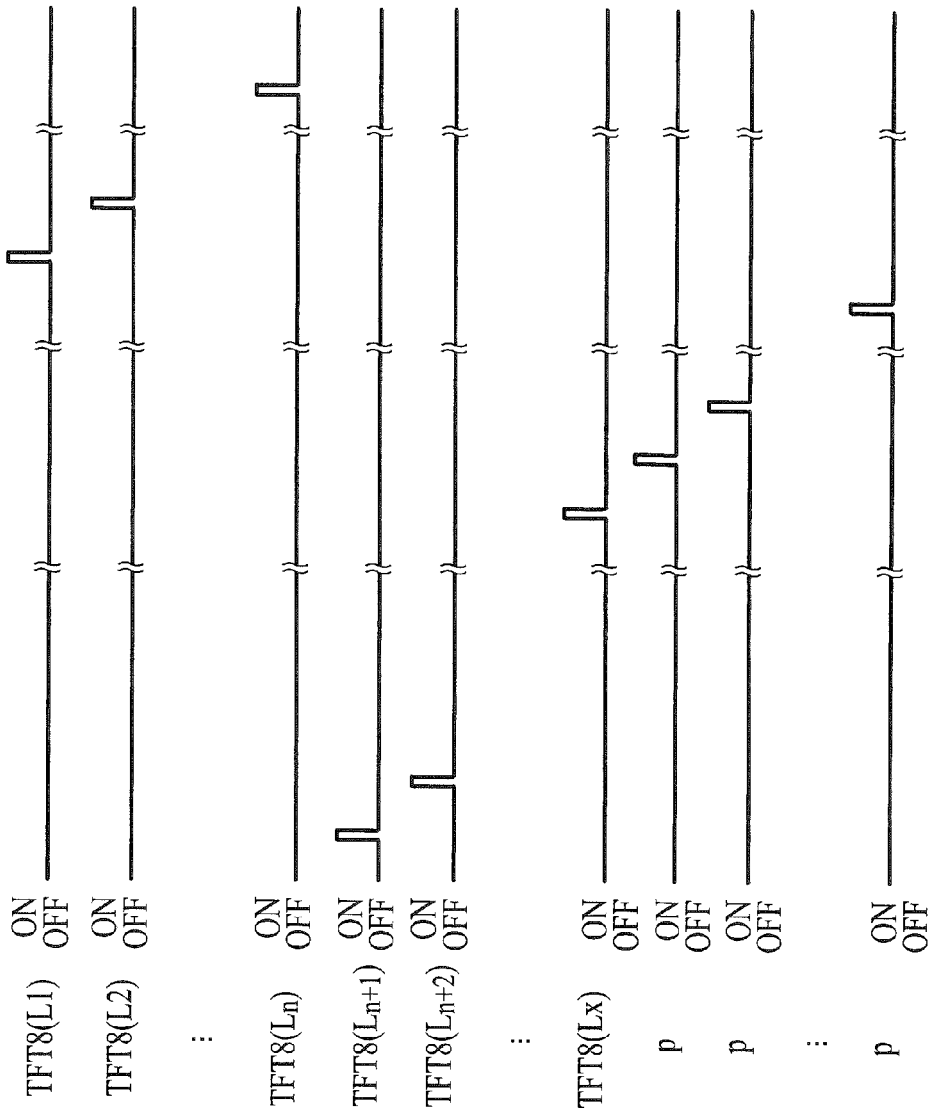
FIG. 31 is a timing chart of a case where the on-state voltage is applied to the unconnected terminal in the acquisition process of offset data according to the configuration of FIG. 30.

Therefore, same is applied to the readout process of the image data D, the acquisition process of dark image data Od, or the like. However, in the acquisition process of the offset data O, for example, after the on-state voltage is sequentially applied from, for example, line $L_{n+1}$ of the scanning line 5 and readout operation of offset data O is started, as shown in FIG. 31, the on-state voltage is sequentially applied to each of the non-connecting terminals p and then, back to the first line $L_1$ of the scanning line 5, the on-state voltage is sequentially applied to the lines $L_1$ to $L_n$ of the scanning line 5.

In a case where non-connecting terminal p thus exists in gate driver 15b, process to sequentially apply the on-state voltage to every terminal including the non-connecting terminal p is carried out on the gate driver 15b side. However, when seen from each scanning line 5 side, when the on-state voltage is applied to the non-connecting terminal p, it becomes a condition where the on-state voltage is not applied to any of the scanning lines 5, as shown in FIG. 31.

Therefore, in a case where, for example, a table for correlating image readout number and the constants y and z shown in FIG. 29 is prepared in the above-described three determination methods, attention must be paid to the following (same is applied to a case where a table for correlating image readout number and approximation formula is prepared).

Note that in the following, explanation will be given of a case where the number of scanning lines 5 is 1000 and the number of non-connecting terminals p is 50, that is, there exist 1050 terminals to the gate driver 15b including the non-connecting terminal p.

In this case, if irradiation was performed to the radiation image capturing apparatus 1 and the starting scanning line 5 from which the readout process of the main image data D is carried out (which corresponds to line $L_{n+1}$ of scanning line 5 in FIG. 18) was $301^{st}$ line of the scanning line 5, in the above-described experiment, starting scanning line 5 becomes the $301^{st}$ line of the same scanning line 5 as in the readout process of the main image data D.

Then, in the acquisition process of each offset data O, the on-state voltage is sequentially applied from starting scanning line 5, that is, $301^{st}$ line of the scanning line 5, to $1000^{th}$ line (that is, final line $L_x$ of the scanning line 5) and the offset data O is read out respectively. Subsequently, the on-state voltage is sequentially applied to the non-connecting terminals p and following that, the on-state voltage is sequentially applied from the first line of the scanning line 5 (that is, the first line $L_1$ of the scanning line 5) to the $300^{th}$ line to read out offset data O respectively.

Then, this process is repeated for each acquisition process of each offset data O. Note that while the on-state voltage is applied to the non-connecting terminal p, the offset data O is not read out.

Then, Olag, portion offset by lags, is calculated from each offset data O acquired in the acquisition process of each offset data O and the above-mentioned constants y and z are calculated for each scanning line 5.

Moreover, in the above-mentioned case, image readout numbers for $301^{st}$ to $1000^{th}$ lines of the scanning lines 5 are 1 to 700, respectively, 701 to 750 for non-connecting terminals p, and 751 to 1050 for $1^{st}$ to $300^{th}$ lines of scanning lines 5. Therefore, if a table is created by correlating each of calculated constants y and z with each image readout number, a table will have a form as one shown in FIG. 32.

That is, if the non-connecting terminal p exists in the gate driver 15b as described above and calculated constants y and z are correlated with image readout numbers respectively, constants y and z cannot be correlated with the image readout numbers corresponding to the non-connecting terminals p.

Therefore, there arises a problem if a table thus created is applied to a case where starting scanning line 5 happens to be, for example, the first line $L_1$ of the scanning line 5.

That is, in a case where the starting scanning line 5 is the first line $L_1$ of the scanning lines 5, image readout numbers for the $1^{st}$ to $1000^{th}$ lines of the scanning lines 5 are 1 to 1000, respectively, and 1001 to 1050 for non-connecting terminals p. However, since constants y and z cannot be allocated to $700^{th}$ to $750^{th}$ lines of the scanning lines 5 with image readout numbers of 700 to 750 in the table, in terms of each of the radiation detection elements 7 connected to these scanning lines, Olag, portion offset by lags, cannot be calculated on the basis of the above equation (14).

Therefore, in a case like this where the non-connecting terminal p exists in the gate driver 15b, for example, it is possible to prepare a table in which image readout numbers and average values of constants y and z or the like are correlated by conducting the above-described experiment a plurality of times by changing starting scanning line 5 to various scanning line 5, as mentioned above, and calculating the average value or the like of constant y or constant z for each image readout number. Note that in this case also, it is possible to configure that the constants y and z to be correlated with image readout numbers are determined on the basis of a result obtained by straight-line approximation or the like of average value or the like of constants y and z before and after, for example, starting scanning line 5.

Figure 32:
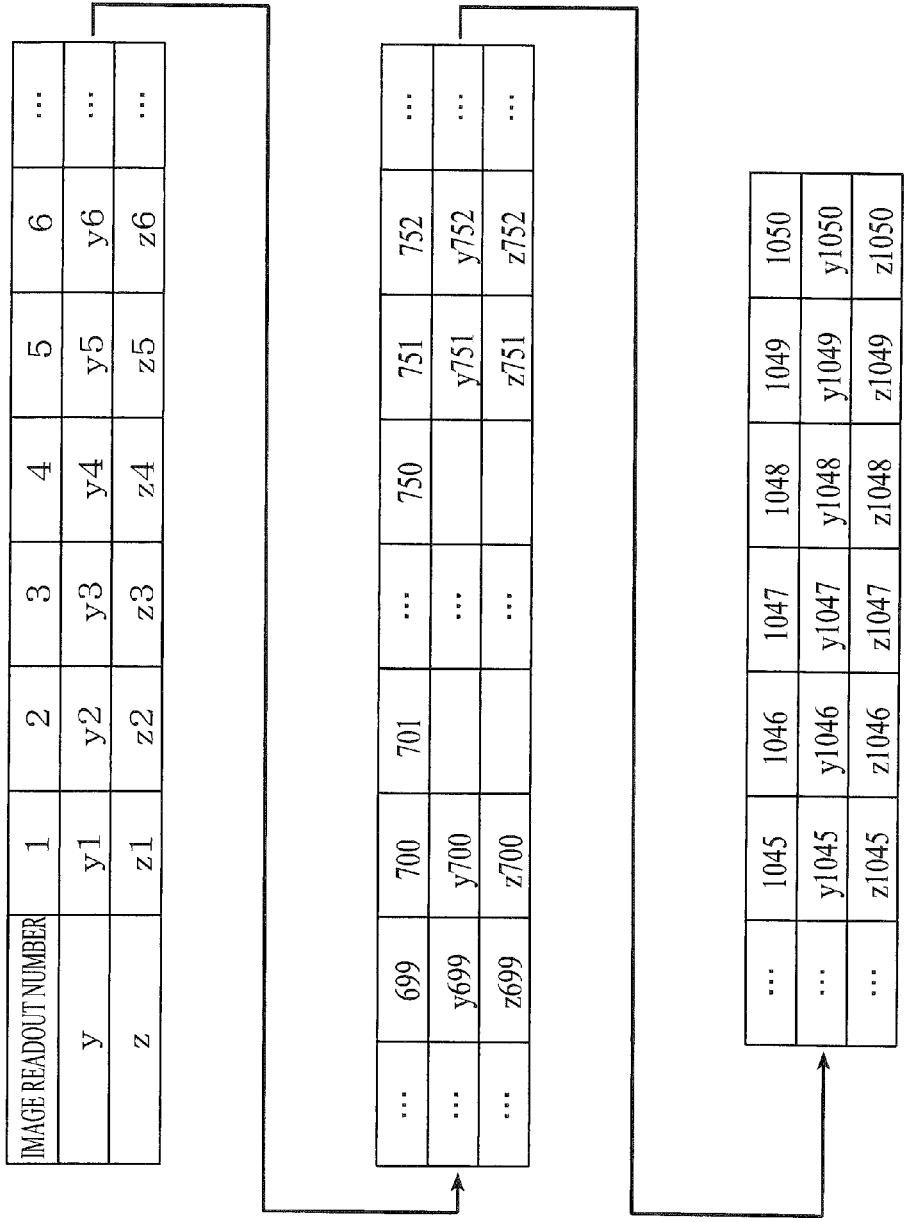
FIG. 32 is a view showing an example of a table created in a case where there exists an unconnected terminal in the gate driver.

Moreover, it is also possible to configure that constant y or constant z for each image readout number obtained by one experiment as shown in FIG. 32 is plotted for each line number m of the scanning line 5, as shown in FIG. 28A and FIG. 28B, and, for example, subject to straight-line approximation before and after the starting scanning line 5, to estimate constants y and z for the part of the non-connecting terminals p (parts with image readout numbers 701 to 750 in FIG. 32) by extending the straight-approximation.

That is, as shown in FIG. 30, in a case where a non-connecting terminal p exists outside of the final line $L_x$ of the scanning line 5, it is possible to configure that straight-approximation on right side (that is, on the side with a larger line number) of starting scanning line 5 (a line with a line number m of 453 in FIG. 28A and FIG. 28B) is extended further right than the final line $L_x$ of scanning line 5 to estimate constants y and z for the part of non-connecting terminal p.

Moreover, although illustration thereof is omitted, in a case where non-connecting terminal p exists outside of line $L_1$, the first line of the scanning line 5, straight-approximation on left side of the starting scanning line 5 (a line with a line number m of 453 in FIG. 28A and FIG. 28B) (that is, on the side with a smaller line number) is extended further left than the first line $L_1$ of scanning line 5 to estimate constants y and z for the part of the non-connecting terminal p.

By creating a table in this manner, it also becomes possible to create a table in which each image readout number and constants y and z are correlated.

Fourth Embodiment

On the other hand, in each of the above embodiments, it was assumed that an approximation formula for approximating Olag, portion offset by lags, is an approximation formula in which a member dependent on the dose of emitted radiation (that is, a member of Olag_pre) and a member which is not dependent on the dose of radiation but dependent on elapsed time t (that is, a member of $y \cdot t^z$) are separated, as shown in the above equation (14).

Moreover, in a case where an approximation formula shown in the above equation (9) is used as an approximation formula of Olag, portion offset by lags, it was a precondition that the approximation formula is separated into a member dependent on the dose of emitted radiation (that is, a member of $(b/a) \cdot (1-e^{aT})$) and a member which is not dependent on the dose of radiation but dependent on elapsed time t (that is, a member of $e^{-atp}$). Note that in the above equation (9), dose of emitted radiation is reflected by constant b in the above-mentioned member.

However, there arises a problem whether an approximation formula for approximating Olag, portion offset by lags, particularly, Olag, portion offset by lags generated in the previous photographing which is to be overlapped on main image data D to be read out in the subsequent photographing, can be separated into a member dependent on the dose of emitted radiation and a member which is not dependent on the dose of radiation but dependent on elapsed time t, as shown in above equation (14) or equation (9).

According to a study by inventors of the present invention concerning this problem, in a case where it is configured that reset process of each radiation detection element 7 is conducted between readout process of main image data D and acquisition process of offset data O as shown in FIG. 19, it is understood that an approximation formula for approximating Olag, portion offset by lags, can be separated into a member dependent on the dose of emitted radiation and a member which is not dependent on the dose of radiation but dependent on elapsed time t, as shown in above equation (14) or equation (9).

Note that it was also understood that even if it is configured that readout process of image data d from each of the radiation detection elements 7 instead of carrying out reset process of each of the radiation detection elements 7 between the readout process of the main image data D and the acquisition process of the offset data O, an approximation formula for approximating Olag, portion offset by lags, can be separated into a member dependent on the dose of emitted radiation and a member which is not dependent on the dose of radiation but dependent on elapsed time t.

Therefore, in each of the above embodiments, it is possible to configure that reset process of each of the radiation detection elements 7 carried out between readout process of main image data D and acquisition process of offset data O is substituted with readout process of image data d from each of the radiation detection elements 7.

In the above-mentioned study conducted by the inventors of the present invention, an experiment similar to the one in the case of FIG. 26 was conducted by use of radiation image capturing apparatus 1 having a configuration explained in the first embodiment or the like, by configuring that readout process of the image data d from each of the radiation detection elements 7 is carried out between the readout process of the main image data d and the acquisition process of the offset data O as shown in FIG. 19 and changing dose of radiation emitted onto the radiation image capturing apparatus 1 variously.

Figure 33:
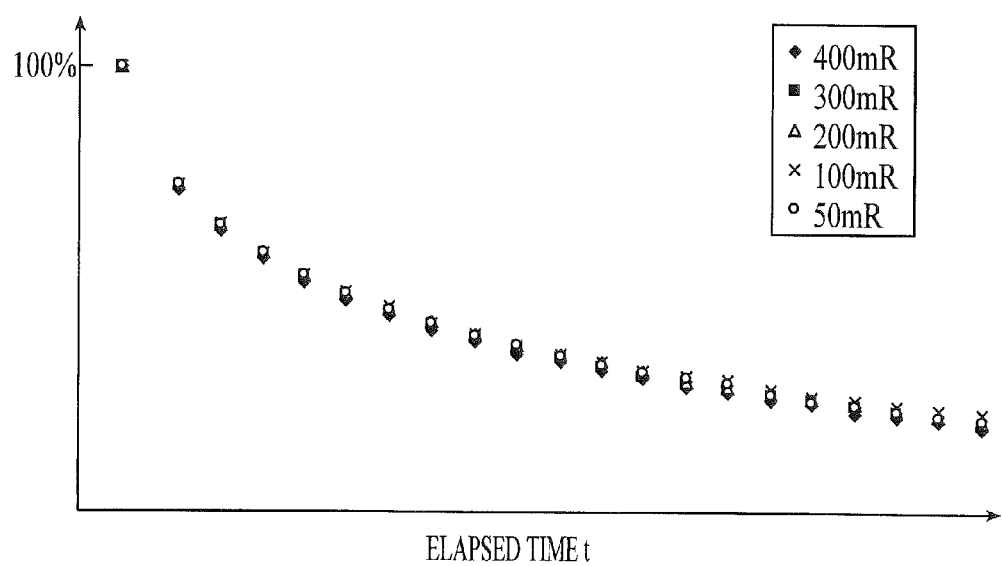
FIG. 33 is a graph showing a result of an experiment in which the same experiment as that of FIG. 26 was conducted while the amount of dose of radiation to be emitted was changed variously.

Then, when a relative ratio of Olag, portion offset by lags calculated from offset data O acquired by each acquisition process of the offset data O which was repeatedly carried out, to Olag_pre, portion offset by lags acquired by the acquisition process of the offset data O at the time of irradiation with radiation, (equivalent to the member of $y \cdot t^2$ in the above equation (14)) was plotted to elapsed time t, a result shown in FIG. 33 was obtained.

As understood from the result of FIG. 33, if it is configured that the readout process of the image data d from each of the radiation detection elements 7 is carried out between readout process of main image data d and acquisition process of offset data O as shown in FIG. 19, a relative ratio of Olag, portion offset by lags, with respect to Olag_pre is not dependent on the dose of the emitted radiation, but attenuates almost in the same attenuating manner regardless of the radiation dose.

As described above, at least in the radiation image capturing apparatus 1 having a configuration described in the first embodiment and the like, if it is configured that the readout process of the image data d from each of the radiation detection elements 7 is carried out between readout process of main image data d and acquisition process of offset data O, an approximation formula for approximating Olag, portion offset by lags generated in the previous photographing and overlapped on main image data D to be read out in the subsequent photographing can be separated into a member which is dependent on dose of emitted radiation and a member which is not dependent on the dose of radiation but is dependent on elapsed time t (that is, a member concerning the above-mentioned relative ratio) and can be expressed as a product thereof.

However, even if it is configured that reset process of each of the radiation detection elements 7 or the like is carried out between readout process of main image data D and acquisition process of offset data O, approximation formula for approximating Olag, portion offset by lags generated in the previous photographing which is overlapped on main image data D to be read out in the subsequent photographing, is not necessarily expressed in the above-mentioned form concerning all the radiation image capturing apparatus.

Moreover, in a study by the inventors of the present invention, even in a case where the radiation image capturing apparatus 1 having a configuration explained in the first embodiment was used, when it was configured that acquisition process of offset data O was carried out immediately after readout process of main image data D by shifting to electric charge accumulation mode without carrying out reset process of each of the radiation detection elements 7 between readout process of main image data D and acquisition process of offset data O, an approximation formula cannot be necessarily separated into a member which is dependent on dose of emitted radiation and a member which is not dependent on the dose of radiation but is dependent on elapsed time t as mentioned above.

Figure 34:
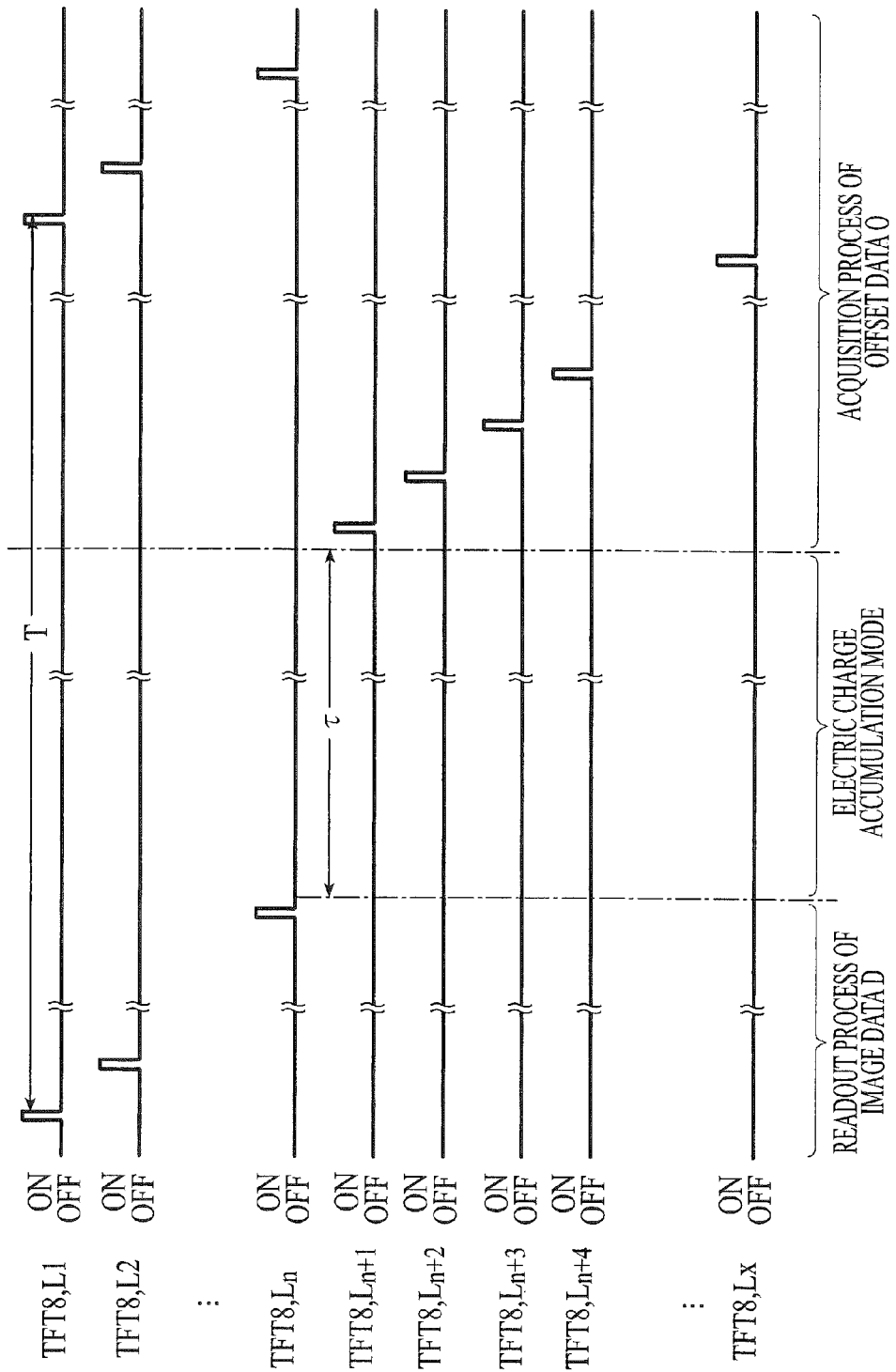
FIG. 34 is a timing chart showing timing for applying the on-state voltage to each scanning line in a case where the reset processor the like of each of the radiation detection elements is not carried out between the readout process of main image data and the acquisition process of the offset data.
Figure 35:
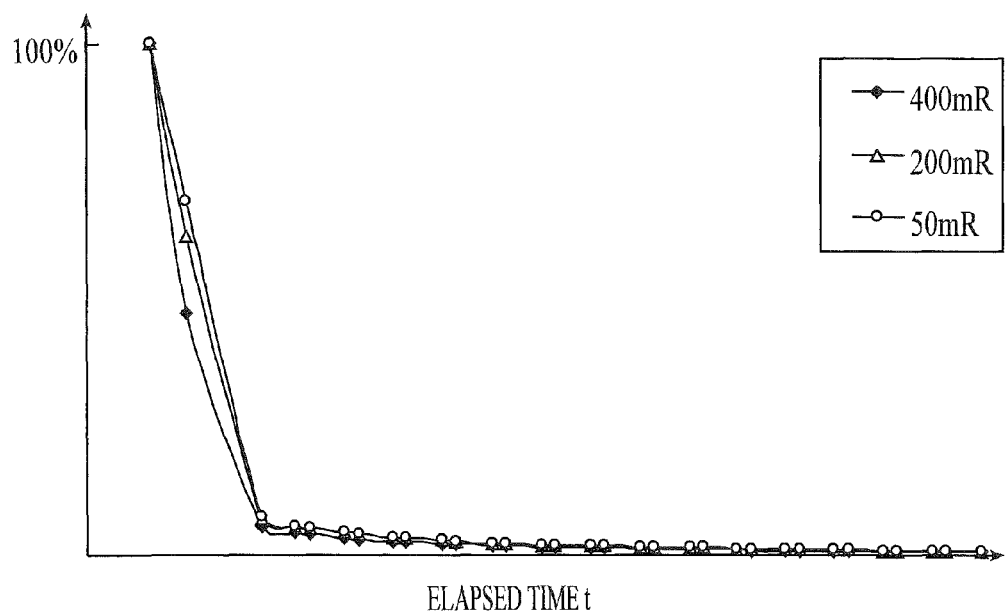
FIG. 35 is a graph showing a result of an experiment in which the same experiment as that of FIG. 26 was conducted for the case of FIG. 34 while the amount of dose of radiation to be emitted was changed variously.

That is, if it is configured that the readout process of the main image data D and the acquisition process of the offset data O are carried out by the radiation image capturing apparatus 1 having a configuration explained in the first embodiment or the like as shown in FIG. 34, similarly to the case of FIG. 33, it is understood that a result shown in, for example, FIG. 35 is obtained when a relative ratio of Olag, portion offset by lags calculated from offset data O acquired by each acquisition process of offset data O which was repeatedly carried out, to Olag_pre, portion offset by lags acquired by acquisition process of offset data O at the time of irradiation with radiation, was plotted to elapsed time t.

Then, in this case, the relative ratio of Olag, portion offset by lags calculated from offset data O acquired by each acquisition process of offset data O which was repeatedly carried out, to Olag_pre does not show almost same attenuation tendency as one shown in FIG. 33, but shows an attenuation tendency that a member related to the relative ratio (that is, a member dependent on the above-mentioned elapsed time t) changes depending also on the dose of radiation.

As shown in FIG. 34, the reason why attenuation tendency of the relative ratio becomes dependent on dose of emitted radiation when it is configured that reset process of each of the radiation detection elements 7 or the readout process of the image data d from each of the radiation detection elements 7 is not carried out between readout process of the main image data D and the acquisition process of the offset data O is assumed as follows.

Readout efficiency of image data attributable to electric charges generated by irradiation with radiation from each of the radiation detection elements 7 in readout process of the main image data D (that is, above-mentioned true image data D*) generally not 100% and true image data D* is left unread at a certain rate.

At this time, if it is configured as shown in FIG. 19 that reset process of each of radiation detection elements 7 or readout process of image data d from each of the radiation detection elements 7 is carried out between readout process of main image data D and acquisition process of offset data O, portion of true image data D* left unread by read out process of main image data D is eliminated from each of the radiation detection elements 7 by reset process or the like.

Therefore, offset data O read out by acquisition process of offset data O to be subsequently held does not include left unread part of true image data D* and offset lag part Olag_pre calculated by subtracting dark image data Od from offset data O according to the above equation (12) does not include left unread part of true image data D*. Thus, Olag_pre has values purely attributable to lags.

Moreover, offset data O acquired by acquisition process of each offset data repeated subsequently also does not include left unread part of true image data D* and therefore offset lag part Olag calculated from these offset data O becomes a value purely attributable to lags.

Thus considered, it is conceivable that the results shown in FIG. 33 does not include left unread part of true image data D* and express that the relation of attenuation tendency between relative ratio of offset lag part Olag_pre attributable purely to lags and Olag and elapsed time t does not depend on dose of emitted radiation.

On the contrary, as shown in FIG. 34, in a case where it is configured that reset process of each of the radiation detection elements 7 or readout process of image data d from each of the radiation detection elements 7 is carried out between readout process of main image data D and acquisition process of offset data O, left unread part of true image data D* which was not read out by readout process of main image data D is included in offset data O read out by acquisition process of offset data O carried out immediately thereafter.

Therefore, left unread part of true image data D* is included in offset lag part Olag_pre calculated by subtracting dark image data Od from offset data O according to the above equation (12) and offset lag part Olag_pre comes to have a value obtained by adding a value purely attributable to lags and left unread part of true image data D*.

Left unread part of true image data D* is, as described above, generally a value obtained by multiplying a predetermined rate to true image data D* generated in each of the radiation detection elements 7 and true image data D* generated in each of the radiation detection elements 7 varies depending on the dose of radiation irradiated to each of the radiation detection elements 7. That is, the larger dose of radiation irradiated to each of the radiation detection elements 7 becomes, the larger true image data D* generated in each of the radiation detection elements 7 becomes.

Therefore, the larger the dose of emitted radiation becomes, the larger left unread part of true image data D* becomes, and the offset lag part Olag_pre becomes larger as the true image data D* becomes larger.

However, on the other hand, left unread part of true image data D* is not included in offset data O acquired by repeatedly carried out acquisition process of each offset data O as described above and offset lag part Olag calculated from these offset data O comes to have a value purely attributable to lags.

Therefore, as shown in FIG. 35, it is assumed that relative ratio of offset lag part Olag acquired by each of repeatedly carried out acquisition process of offset data O to offset lag part Olag_pre becomes smaller as dose of emitted radiation becomes larger and attenuation tendency of relative ratio to elapsed time t depends on dose of emitted radiation.

Due to the above reasons, as in each of the above described embodiments (refer to FIG. 19), if it is configured that reset process of each of the radiation detection elements 7 or readout process of image data d from each of the radiation detection elements 7 is carried out between readout process of main image data D and acquisition process of offset data O, an approximation formula for approximating offset lag part Olag can be divided into a member which depends on dose of emitted radiation and a member which does not depend on the dose of radiation by on elapsed time t, as shown in above equation (14) or equation (9).

Then, because it becomes possible to use an approximation formula having such a simple form, it becomes possible to calculate offset lag part Olag by use of one approximation formula or a simple table such as one shown in FIG. 29 by use of the methods explained in each of the above-described embodiments and to accurately correct main image data D.

Meanwhile, in a case where it is configured that reset process of each of radiation detection elements 7 or readout process of image data d from each of radiation detection elements 7 is not carried out between readout process of main image data D and acquisition process of offset data O as shown in FIG. 34, relative ratio of offset lag part Olag acquired by each of repeatedly carried out acquisition process of offset data O (that is, offset lag part Olag overlapped on main image data D in the subsequent photographing) to first (that is, generated in the previous photographing) offset lag part Olag_pre becomes dependent on dose of emitted radiation.

This is because left unread part of true image data D* is included in offset lag part Olag_pre acquired by acquisition process of offset data O carried out immediately after irradiation with radiation. Then, left unread part of true image data D* can be generally calculated as a value obtained by multiplying a predetermined rate to true image data D* generated in each of radiation detection elements 7.

Determination of predetermined rate is dependent on configuration of the radiation detection element 7 or TFT 8 or a value of the on-state voltage applied to TFT 8 (that is, configuration of the scanning drive unit 15), readout efficiency of data from each of the radiation detection elements 7 by the readout circuit 17, or the like and generally varies depending on the form of the radiation image capturing apparatus 1.

However, when seen by each of the radiation image capturing apparatus 1, the above-mentioned rate does not vary depending on each photographing and generally becomes a consistent value. Therefore, it is assumed that attenuation tendency of relative ratio of offset lag part Olag to Olag_pre to elapsed time t becomes similar tendency for each photographing.

Therefore, when it is configured that reset process of each of the radiation detection elements 7 or the like is not carried out between readout process of main image data D and acquisition process of offset data O, constants y and z are set as functions of dose of radiation by carrying out experiments in which dose of radiation emitted onto the radiation image capturing apparatus 1 is variously changed in advance.

Moreover, a table in which constants y and z and dose of radiation are correlated may be created. In this case, it is configured that when a dose of radiation which does not exist in the table is emitted, for example, constants y and z corresponding to the dose of emitted radiation are calculated on the basis of the relation between constants y and z and dose of radiation in the table, for example by linear interpolation or the like.

Otherwise, it is also possible to configure that an approximation formula expressing relative ratio of offset lag part Olag to Olag_pre is allocated to each dose by conducting experiments in which dose of radiation irradiated to radiation image capturing apparatus 1 is variously changed in advance. In this case, if an approximation formula corresponding to dose of emitted radiation does not exist, for example, relative ratio is calculated by use of an approximation formula for a case where an approximative dose of radiation is emitted and the relative ratio corresponding to the dose of emitted radiation is calculated by, for example by linear interpolation or the like.

It becomes possible to offset lag part Olag generated in the previous photographing is overlapped on main image data D read out in the subsequent photographing by thus calculating relative ratio and multiply the ratio thus obtained to offset lag port Olag_pre acquired by acquisition process of offset data O carried out immediately after irradiation with radiation. Moreover, thanks to this, it becomes possible to accurately correct main image data D.

According to the above configuration, it becomes possible to more accurately provide the effects of the radiation image capturing apparatus 1 or the radiation image capturing system 50 explained in each of the above embodiments.

Fifth Embodiment

In the above-described embodiments, it was assumed that the on-state voltage was sequentially applied to each of the lines $L_1$ to $L_x$ of the scanning lines 5 at the same timing between as applying on-state voltage to a scanning line 5 and applying on-state voltage to a next scanning line 5 in acquisition process of dark image data Od, readout process of main image data D, and acquisition process of offset data O.

Moreover, it was assumed that in readout process of main image data D, application of on-state voltage is started to a scanning line 5 (which corresponds to line $L_{n+1}$ of scanning line 5 in FIG. 18) to which on-state voltage is to be applied following a scanning line 5 (which corresponds to line $L_n$ of scanning line 5 in FIG. 18) to which on-state voltage has been applied at the point where initiation of irradiation with radiation was detected by readout process of image data O before photographing of a radiation image, or immediately before that, and on-state voltage is sequentially applied to each of the scanning lines 5 so that readout process of main image data D is carried out.

Then, if thus configured, effective accumulation time for each of the lines $L_1$ to $L_x$ of the scanning line 5 becomes the same. Therefore it becomes unnecessary to convert and calculate offset data Odark attributable the offset data Od(D) attributable to dark electric charges included main image data D or offset data O included in dark electric charges included offset data O form dark image data Od. Then, there is an advantage that it becomes possible to process that as shown in above equation (6) that offset data Od(D) and Odark are substituted with dark image data Od and computation process can be easily carried out.

However, depending on the radiation image capturing apparatus 1, it was not possible to configure as above due to the problem of hardware or software. Moreover, it is not possible to adopt the above configuration in a case where there is a demand to carry out readout process of main image data D is carried out more quickly or the like.

Figure 36:
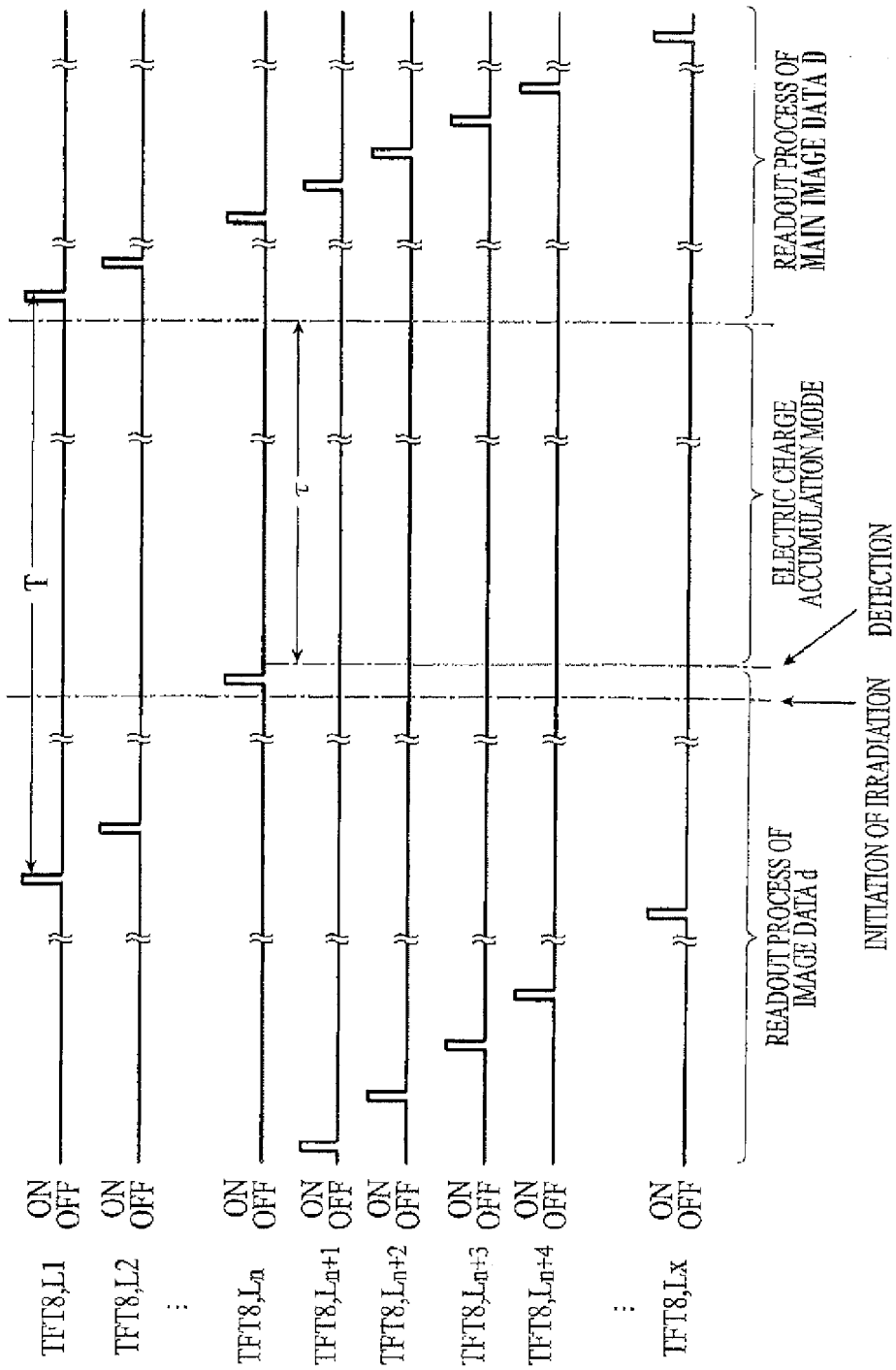
FIG. 36 is a timing chart showing timing for transition from readout process of the image data before photographing of a radiation image to electric charge accumulation mode and for applying the on-state voltage to each scanning line in the readout process of the main image data according to a fifth embodiment.

Therefore, in the fifth embodiment, as shown in FIG. 36, although readout process of image data d before photographing of a radiation image is carried out in a similar manner to the above-described embodiments, application of on-state voltage is started from the first line L1 of scanning line 5 in readout process of main image data D and, in addition to that, on-state voltage is sequentially applied to each of the lines L1 to Lx of the scanning lines 5 at different timing of the readout process of the image data d before photographing.

Figure 37:
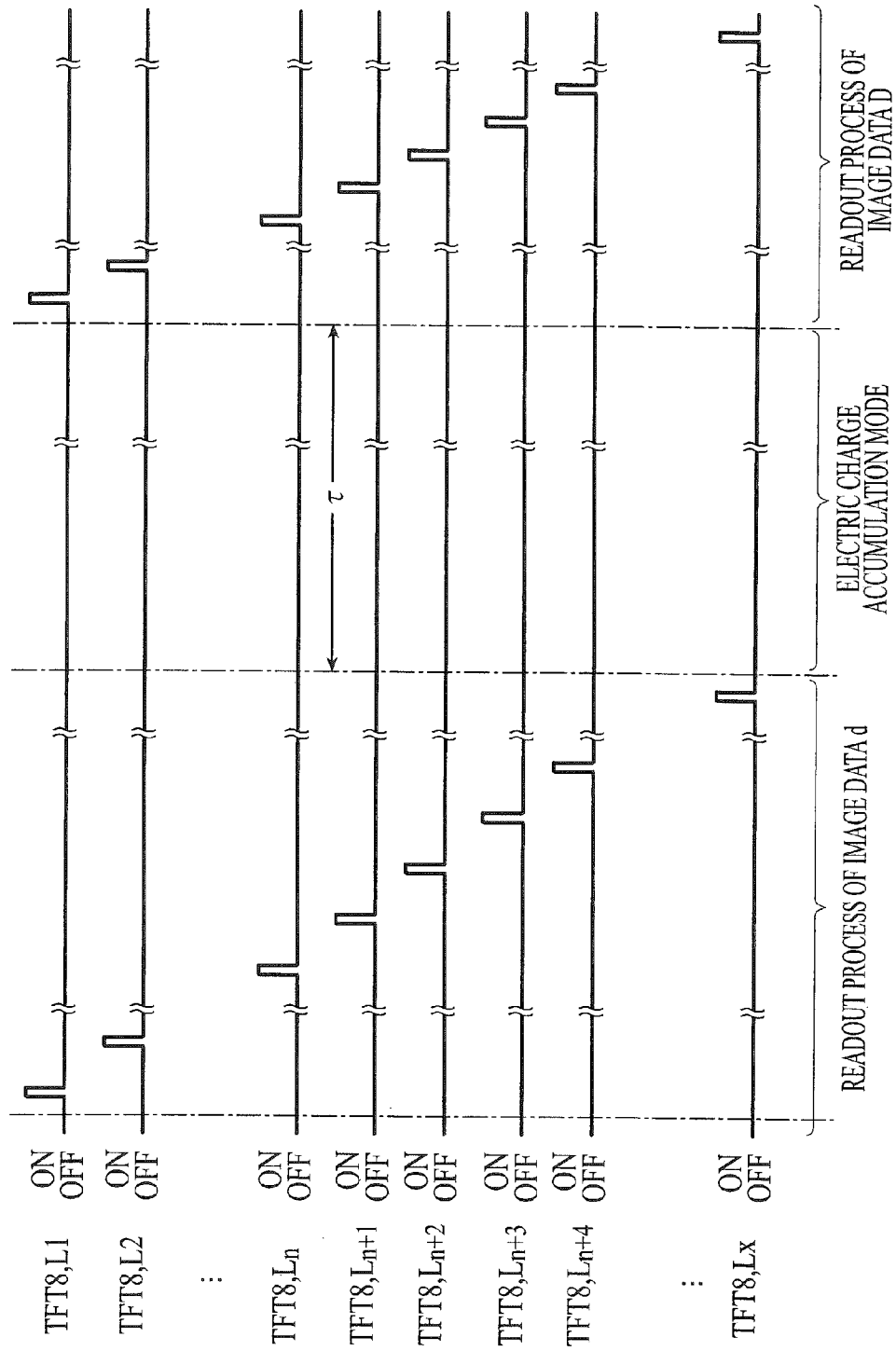
FIG. 37 is a timing chart showing timing for applying the on-state voltage to each scanning line in the acquisition process of the offset data according to the fifth embodiment.

In this case also, after readout process of main image data D is carried out and off-state voltage is applied to each scanning line 5 for a predetermined time T as shown in FIG. 37, or after reset process of each of radiation detection elements 7 is carried out for a predetermined time for a frame, though not shown, and off-state voltage is applied to each of the scanning lines 5 for a predetermine time τ and subsequently on-state voltage is applied to each of the lines $L_1$ to $L_x$ of the scanning lines 5 at the same timing as in the case of main image data D, to carry out acquisition process of the offset data O.

Moreover, in this case, in the present embodiment, as shown in FIG. 36, effective accumulation time T particularly at the time of readout process of the main image data D, that is, time T from application of final on-state voltage to each of the scanning lines 5 in the readout process of image data d before photographing of a radiation image until on-state voltage is applied in the readout process of the main image data D, varies depending on scanning lines 5.

In addition, when focusing on effective accumulation time T for each scanning line 5, the effective accumulation time T is not constant for each photographing of a radiation image, but varies for each photographing of a radiation image for a scanning line 5 to which on-state voltage is applied at the point of time when irradiation with radiation to a radiation image capturing apparatus 1 is detected, and therefore effective accumulation time T for the scanning line 5 varies for each photographing of a radiation image.

Therefore, offset part Od(D) attributable to dark electric charge which is overlapped on main image data D (refer to FIG. 21B) varies for each photographing of a radiation image.

Therefore, as explained in the above-described embodiments (refer to FIG. 20), it becomes possible to configure that acquisition process of dark image data Od is carried out at the time of readout process of image data d before photographing of a radiation image to acquire dark image data Od for each of the radiation detection elements 7, and dark image data Od acquired in effective accumulation time T in acquisition process of dark image data Od is converted by effective accumulation time T at the time of readout process of main image data D for each of the above-mentioned scanning line 5 so that offset part Od(D) attributable to dark electric charges which is to be superimposed on main image data D can be calculated by computation.

Moreover, in a case where the above equation (9) or equation (14) is used to calculate offset lag part Olag or the like included in offset data O, times t and tp applied to each equation have different values for each of scanning lines 5, similarly to the case of each of the above-described embodiment.

However, in this case, when offset lag part Olag or the like is calculated by use of, particularly, the above equation (9), since effective accumulation time T was the same length for each scanning line 5 in the above-described embodiments, the member (1−exp(−aT)) of the equation (9) could be assumed as a constant. However, in the present embodiment, since effective accumulation time T differs for each scanning line 5 as described above, it becomes necessary to calculate effective accumulation time T for each scanning line 5 and substitute the calculated value for the above member to carry out computation.

Figure 38:
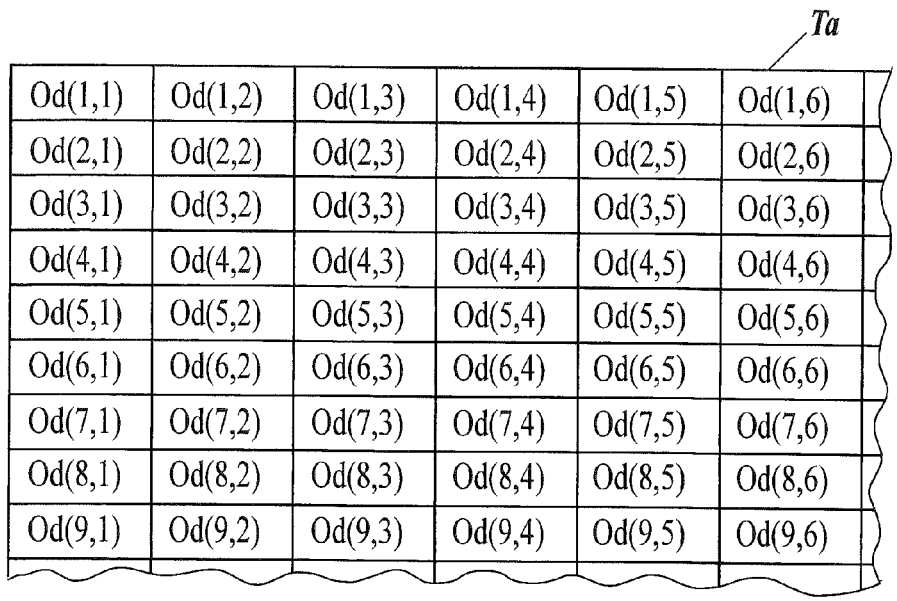
FIG. 38 is a view illustrating a table concerning offset portion attributable to the dark electric charges of each radiation detection element.

Moreover, when the above-described computation process is carried out, it becomes necessary to carry out many computation processes and therefore instead of carrying out the above-described computation process, for example, it is possible to configure that offset part Od (m, n) attributable to dark electric charges for each of the radiation detection elements (m, n) in a case where initiation of radioactive irradiation is detected when on-state voltage is applied to a scanning line 5 is experimentally acquired and a table Ta is created as shown in FIG. 38 and offset part Od (m, n) attributable to dark electric charges for each of the radiation detection elements (m, n) is calculated based on the table Ta.

Figure 39:
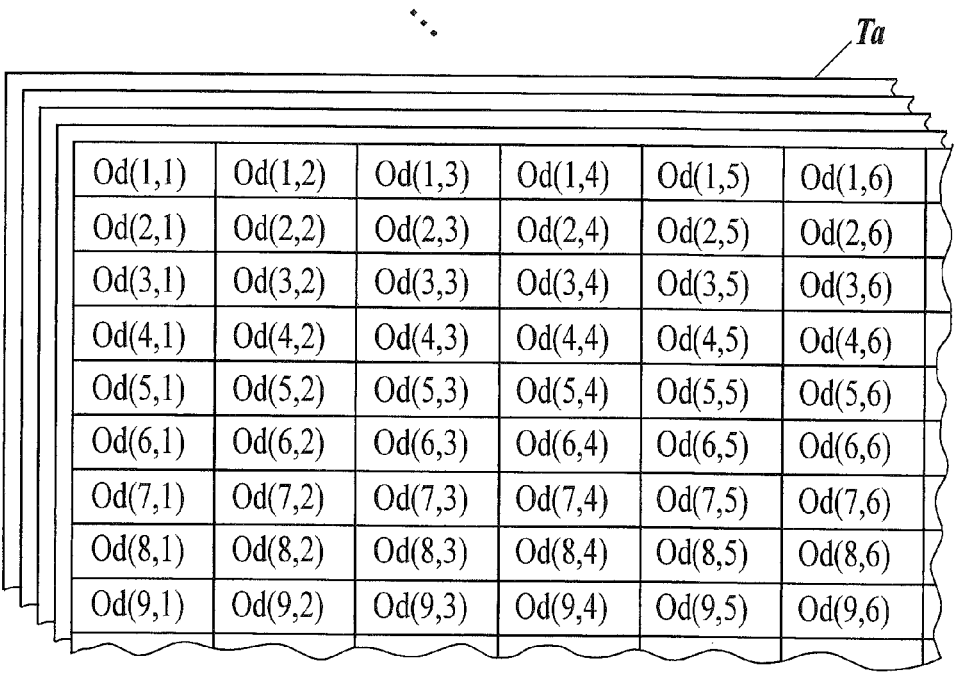
FIG. 39 is a view illustrating a group of tables.
Figure 40:
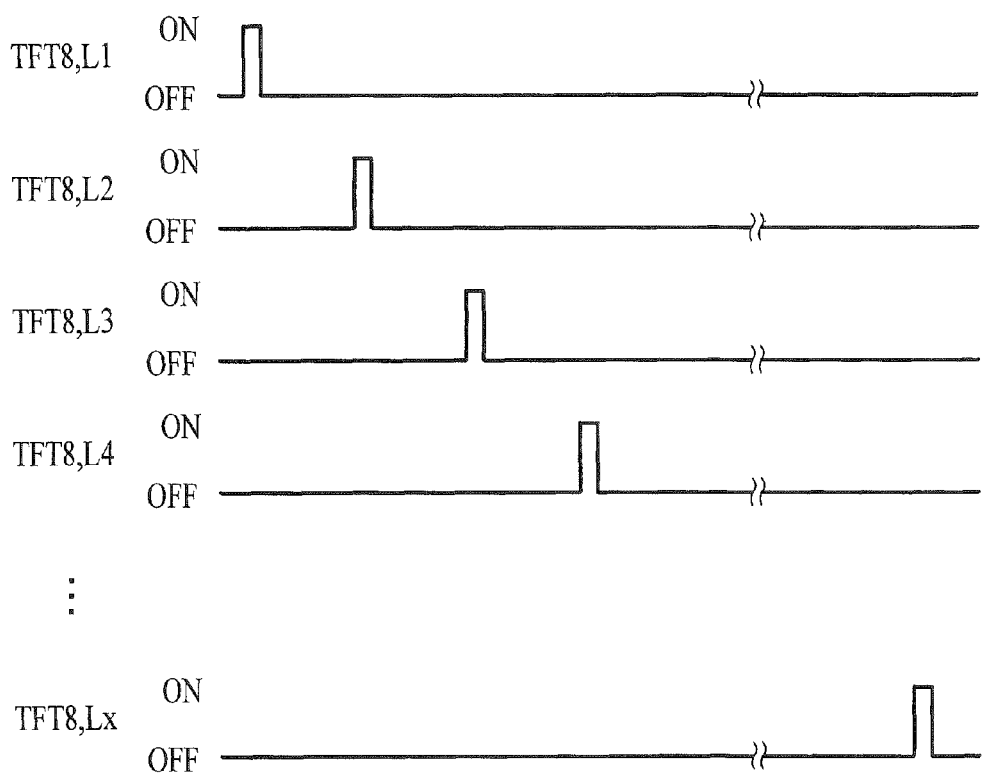
FIG. 40 is a timing chart showing timing for switching between on-state and off-state voltage which is to be applied to each scanning line in the readout process of the image data.

In this case, scanning line 5 to which on-state voltage had been applied at the point of time when initiation of radioactive irradiation to the radiation image capturing apparatus 1 was detected varies for each photographing as described above, table Ta is created for each of the scanning line 5 to which on-state voltage had been applied at the point of time when initiation of radioactive irradiation was detected, that is, lines $L_1$ to $L_x$ of the scanning line 5, as shown in FIG. 39.

Then, it is configured that the control unit 22 or the console 58 determines a table Ta to refer to based on information of scanning line 5 to which on-state voltage had been applied at the point of time when initiation of radioactive irradiation to the radiation image capturing apparatus 1 was detected and on the basis of the table Ta, acquires offset part Od (m, n) attributable to each of the radiation detection elements (m, n). The group of tables Ta is stored in the storage unit 40 of the radiation image capturing apparatus 1 (refer to FIG. 7 or the like) or the storage unit 59 of the console 58 in advance.

Note that as shown in FIG. 37, in a case where the acquisition process of the offset data O is carried out at the same timing as that of the application of the on-state voltage to each scanning lines 5 in the readout process of the main image data D, effective accumulation time in acquisition process of offset data O becomes same duration for each scanning line 5.

Therefore, concerning offset part Odark which is attributable to dark electric charges and is at least superimposed on offset data O (refer to FIG. 21B), it is possible to configure that dark image data Od acquired by acquisition process of dark image data Od which is carried out at the time of readout process of image data d before photographing of a radiation image is used. Moreover, it is also possible to configure that tables for each of the radiation detection elements (m, n) of offset part Odark attributable to dark electric charges which is, similarly to the above, superimposed on offset data O, are created in advance to be referred to.

Thus, it becomes possible to configure that main image data D can be corrected similarly to the cases of the above-described embodiments except that offset part Od(D) attributable to dark electric charges included in main image data D (and offset part Odark in a case where the offset part Odark attributable to dark electric charges included in offset data O is calculated by referring to a table) is calculated by the above-described computation process or by referring to the above-mentioned table Ta.

That is, in a case where the first embodiment is applied to the present embodiment, offset part Odark attributable to dark electric charges included in offset data O is assumed as dark image data Od, or acquired as offset part Odark calculated by referring to a table, and offset part Odark attributable to dark electric charges which is superimposed on offset data O is subtracted from offset data O to calculate offset lag part Olag included in offset data O.

Then, based on offset lag part Olag included in offset data O thus calculated, offset lag part Olag (D) included in main image data D is estimated and offset lag part Olag (D) included in main image data D estimated as above and offset part Od(D) attributable to dark electric charges included in main image data D which was calculated by referring to the above-mentioned table Ta are subtracted from main image data D to calculate genuine image data D*. Thus, it becomes possible to configure that main image data D is corrected.

Moreover, in a case where the second embodiment is applied to the present embodiment, offset part Odark attributable to dark electric charges which is superimposed on offset data O is subtracted in advance by referring to the above-mentioned table Ta and experiments to calculate offset lag part Olag included in offset data O which is included in offset data O are carried out in a repeated manner.

Then, from the result of offset lag part Olag included in offset data O which was thus calculated, an approximation formula for approximating generation rate of a lag per a unit time or an approximation formula for approximation temporal changes of offset lag part Olag itself is set.

Then, based on the above, offset lag part Olag, which was generated in the former photographing and is included in main image data D acquired in latter photographing is estimated and offset part Od(D) attributable to dark electric charges included in main image data D is calculated by referring to the above-mentioned table Ta to subtract the offset lag part Olag generated in the former photographing and offset part Od(D) attributable to dark electric charges so that genuine image data D* is calculated. Thus, it is possible to configure that main image data D acquired in the latter photographing is corrected.

Thus, by applying each of the above-described embodiments to the present embodiment, it becomes possible to accurately eliminate offset lag part Olag generate by the photographing or offset lag part Olag generated by the former photographing, which is included in main image D, from main image data D corrected as above.

Then, it becomes possible to generate a final radiation image based on main image data D from which influence by lags is accurately eliminated, that is, based on genuine image data D*. Therefore, it becomes possible to accurately eliminate the influence by lags from a final radiation image and to improve quality of a final radiation image.

Note that offset lag part Olag generated in the former photographing and is superimposed on main image data D read out in the latter photographing (refer to FIG. 25) becomes smaller as time from the former photographing to the latter photographing becomes longer. Then, if elapsed time from the former photographing reaches a certain duration, contribution by offset lag part Olag generated in the former photographing and is superimposed on main image data D read out in the latter photographing to main image data D read out in the latter photographing becomes small enough to ignore. Then, it is actually not so meaningful to carry out above-described correction process in such a condition.

Therefore, it becomes possible to configure that in a case where latter photographing of a radiation image is carried out after, for example, a predetermined period of time, which was set to be relatively long time in advance, or longer elapsed since radioactive irradiation was detected in the former photographing, correction based on offset lag part Olag generated in the former photographing of a radiation image is not carried out to main image data D read out by photographing of the latter photographing of a radiation image.

According to such a configuration, it becomes possible to avoid process which is substantially unnecessary to be carried out and to reduce process, and at the same time, to more swiftly carry out the above-mentioned preliminary process for calculating genuine image data D* from main image data D or the like.

Note that it is also possible that an approximation formula for approximating offset lag part Olag in each of the above-described embodiments changes depending on the temperature or the like of detecting part P of the radiation image capturing apparatus 1 (refer to FIG. 2, FIG. 3, or the like). That is, for example, there may be a case where constants a and b in the above equation (9), constants y and z in the above equation (14) or the like may change depending on the temperature of detecting part P.

Therefore, in such a case, it becomes possible to configure that constants a and b or constant y and z are acquired as, for example, functions or in the form of a table for each temperature in advance, a temperature sensor is provided to radiation image capturing apparatus 1, for example, or temperature of detecting part P is detected or estimated based on a value of image data d or leaked data $d_{leak}$ read out before photographing of a radiation image or the like to calculate constants a and b or constants y and z which correspond to detected or estimated temperature so that an approximation formula can be set.

INDUSTRIAL APPLICABILITY

The present invention can be applied to a field conducting radiation image photographing (particularly, field of medicine).

REFERENCE SINGS LIST

1 Radiation image capturing apparatus
5 Scanning line
6 Signal line
7, (m, n) Radiation detection elements
8 TFT (switching element)
15 Scanning drive unit
17 Readout circuit
22 Control unit
39 Antenna device 43 Electric current detection unit
50 Radiation image capturing system
58 Console
D Image data (image data as main image)
d Image data
dleak Leaked data
P detecting part
q Electric charge
r Regions
O Offset data
Od Dark image data
Olag Offset lag part
Olag(D) Offset lag part included in image data
τ Predetermined time (time required for electric charge accumulation mode)

The invention claimed is:

1. A radiation image capturing apparatus, comprising:
a detection section comprising:
  a plurality of scanning lines and a plurality of signal lines provided so as to cross with each other, and
  a plurality of radiation detection elements aligned two-dimensionally;
a scanning drive unit that sequentially applies on-state voltage to the plurality of scanning lines to discharge electric charges accumulated in the radiation detection elements to the signal lines;
a readout circuit that converts the electric charges discharged from the radiation detection elements to the signal lines into the image data and reads out the image data; and
a control unit that controls the scanning drive unit and the readout circuit to apply off-state voltage to all of the plurality of scanning lines to shift to an electric charge accumulation mode, and thereafter, sequentially apply on-state voltage to the plurality of scanning lines to read out the image data;
wherein after reading out the image data in a condition where radiation is not irradiated to acquire dark image data, the control unit reads out the image data in a condition where radiation is irradiated to acquire main image data and thereafter reads out the image data in a condition where radiation is not irradiated to acquire offset data;
the radiation image capturing apparatus has a unit that detects initiation of radioactive irradiation;
after acquiring the dark image data before acquiring the main image data, the control unit repeats an operation of sequentially applying the on-state voltage to the plurality of scanning lines, and when the unit which detects initiation of radioactive irradiation detects initiation of radioactive irradiation, the control unit stops the operation of sequentially applying the on-state voltage to the plurality of scanning lines to shift to the electric charge accumulation mode, and
the control unit corrects the main image data or main image data in latter photographing based on information of a scanning line to which on-state voltage was applied at the point of time when initiation of radioactive irradiation was detected by the unit which detects initiation of radioactive irradiation or immediately before the detection of the initiation of radioactive irradiation and an offset lag part calculated by subtracting the dark image data from the offset data.

2. The radiation image capturing apparatus according to claim 1, wherein the control unit causes the scanning drive unit to sequentially apply the on-state voltage to each of the scanning lines in order to carry out reset process of each of the radiation detection elements for causing each of the radiation detection elements to release electric charges and to carry out readout process of leaked data for converting electric charges, which are leaked out to each of the signal lines from each of the radiation detection elements via the switching elements in a condition where the off-state voltage is applied to each of the scanning lines, into the leaked data and for reading out the leaked data;
  the unit which detects initiation of radioactive irradiation detects initiation of radioactive irradiation at a time when the leaked data read out by the readout process of the leaked data exceeds a threshold value, and
  the control unit carries out the readout process of the image data at an appropriate timing before the radiation image capturing operation in a condition where radiation is not irradiated to acquire the image data thus read out as dark image data for each of the radiation detection elements.

3. The radiation image capturing apparatus according to claim 1, wherein the control unit subtracts the dark image data from the main image data, and further subtracts the offset lag part to correct the main image data.

4. The radiation image capturing apparatus according to claim 1, wherein
  in a case where the control unit corrects the main image data in the latter photographing, the control unit subtracts a value, which is obtained by subtracting the offset lag part generated by the former photographing from the offset data acquired by the latter photographing, from a value, which is obtained by subtracting the offset lag part generated by the former photographing from main image data in the latter photographing, in order to correct main image data in the latter photographing.

5. The radiation image capturing apparatus according to claim 1, wherein, when reading out the main image data and when reading out the offset data, the control unit sequentially applies on-state voltage from a scanning line next to a scanning line to which on-state voltage was applied at the point of time when initiation of radioactive irradiation was detected by the unit which detects initiation of radioactive irradiation or immediately before the detection of the initiation of the radioactive irradiation, to sequentially carry out a readout operation.

6. The radiation image capturing apparatus according to claim 1, wherein if a period during which on-state voltage is sequentially applied to each of the scanning lines to read out each of the image data from each of the radiation detection elements or a period for carrying out reset process of each of the radiation detection elements before the radiation image capturing operation is assumed to be one frame,
  in a case where the control unit carries out acquisition process of the dark image data from each of the radiation detection elements before the radiation image capturing operation, the control unit causes the scanning drive unit to apply off-state voltage to each of the scanning lines for the same length of time as that is required for the electric charge accumulation mode between the frame during which acquisition process of the dark image data is carried out and a frame immediately before the frame.

7. A radiation image capturing system, comprising:
a radiation image capturing apparatus comprising:
  a detection section comprising a plurality of scanning lines and a plurality of signal lines provided so as to cross with each other;
  a plurality of radiation detection elements that are two-dimensionally aligned;
  a scanning drive unit that sequentially applies on-state voltage to the plurality of scanning lines and discharges electric charges accumulated in the radiation detection elements to the signal lines;

a readout circuit that converts the electric charges discharged from the radiation detection elements to the signal lines into image data and reads out the image data; and a control unit that controls the scanning drive unit and the readout circuit to apply off-state voltage to all of the plurality of scanning lines to shift to an electric charge accumulation mode, scanning lines to read out the image data;

wherein after reading out the image data in a condition where radiation is not irradiated to acquire dark image data, the control unit reads out the image data in a condition where radiation is irradiated to acquire main image data and thereafter reads out the image data in a condition where radiation is not irradiated to acquire offset data; and a console that acquires the dark image data, the main image data and the offset data from the radiation image capturing apparatus, wherein the radiation image capturing apparatus has a unit that detects initiation of radioactive irradiation;

after acquiring the dark image data before acquiring the main image data, the control unit repeats an operation of sequentially applying the on-state voltage to the plurality of scanning lines, and when the unit which detects initiation of radioactive irradiation detects initiation of radioactive irradiation, the control unit stops the operation of sequentially applying the on-state voltage to the plurality of scanning lines to shift to the electric charge accumulation mode, and the console corrects the main image data or main image data in latter photographing based on information of a scanning line to which on-state voltage was applied at the point of time when initiation of radioactive irradiation was detected by the unit which detects initiation of radioactive irradiation or immediately before the detection of the initiation of radioactive irradiation and an offset lag part calculated by subtracting the dark image data from the offset data.

8. The radiation image capturing system according to claim 7, wherein wherein the control unit causes the scanning drive unit to sequentially apply the on-state voltage to each of the scanning lines in order to carry out reset process of each of the radiation detection elements for causing each of the radiation detection elements to release electric charges and to carry out readout process of leaked data for converting electric charges, which are leaked out to each of the signal lines from each of the radiation detection elements via the switching elements in a condition where off-state voltage is applied to each of the scanning lines, into the leaked data and for reading out the leaked data, the unit which detects initiation of radioactive irradiation detects initiation of radioactive irradiation at a time when the leaked data read out by the readout process of the leaked data exceeds a threshold value, and the control unit carries out the readout process of the image data at an appropriate timing before the radiation image capturing operation in a condition where radiation is not irradiated to acquire the image data thus read out as dark image data for each of the radiation detection elements.

9. The radiation image capturing system according to claim 7, wherein the console subtracts the dark image data from the main image data, and further subtracts the offset lag part to correct the main image data.

10. The radiation image capturing system according to claim 7, wherein in a case where the control unit corrects the main image data in the latter photographing, the console subtracts a value, which is obtained by subtracting the offset lag part generated by the former photographing from the offset data acquired by the latter photographing, from a value, which is obtained by subtracting the offset lag part generated by the former photographing from the main image data in the latter photographing, in order to correct the main image data in the latter photographing.

11. The radiation image capturing system according to claim 7, wherein, when reading out the main image data and when reading out the offset data, the control unit sequentially applies on-state voltage from a scanning line next to a scanning line to which on-state voltage was applied at the point of time when initiation of radioactive irradiation was detected by the unit which detects initiation of the radioactive irradiation, to sequentially carry out a readout operation.

* * * * *